(12) United States Patent
Gordon et al.

(10) Patent No.: US 9,446,406 B2
(45) Date of Patent: Sep. 20, 2016

(54) SAMPLE COLLECTION AND BIOLUMINESCENT ANALYSIS SYSTEM

(71) Applicant: BIOCONTROL SYSTEMS, INC., Bellevue, WA (US)

(72) Inventors: Marc Warren Gordon, Carnation, WA (US); Jon Keith Perrin, Redmond, WA (US); Alexander Michael Diener, Seattle, WA (US); David Oscar Iverson, Seattle, WA (US); Kyle Stuart Johnson, Sammamish, WA (US); Garet Glenn Nenninger, Seattle, WA (US); John Russell Murkowski, Seattle, WA (US); Kristin Marie Will, Seattle, WA (US); Chad Austin Brinckerhoff, Issaquah, WA (US); Phillip T. Feldsine, Mercer Island, WA (US); Tim Allen Kelly, Bellevue, WA (US)

(73) Assignee: BioControl Systems, Inc., Bellevue, WA (US)

( * ) Notice: Subject to any disclaimer, the term of this patent is extended or adjusted under 35 U.S.C. 154(b) by 822 days.

(21) Appl. No.: 13/645,183

(22) Filed: Oct. 4, 2012

(65) Prior Publication Data

US 2014/0004548 A1 Jan. 2, 2014

Related U.S. Application Data

(60) Provisional application No. 61/666,637, filed on Jun. 29, 2012.

(51) Int. Cl.
*G01N 21/94* (2006.01)
*G01N 21/03* (2006.01)
(Continued)

(52) U.S. Cl.
CPC ............. *B01L 3/5029* (2013.01); *G01N 21/01* (2013.01); *G01N 21/763* (2013.01); *B01L 3/5082* (2013.01);
(Continued)

(58) Field of Classification Search
CPC .................. G01N 21/8483; G01N 35/00029; B01L 3/502; B01L 3/5023
USPC .......................................................... 422/404
See application file for complete search history.

(56) References Cited

U.S. PATENT DOCUMENTS 3,359,973 A   12/1967  Hoffman
3,640,267 A   2/1972   Hurtig et al.
(Continued)

FOREIGN PATENT DOCUMENTS

AU   2002357107 A1   6/2003
AU   2003231770 A1   11/2003
(Continued)

OTHER PUBLICATIONS

BioControl® Systems, Inc., "Lightning™ System Guide," 4 pages.
(Continued)

*Primary Examiner* — Neil N Turk
(74) *Attorney, Agent, or Firm* — Seed IP Law Group PLLC

(57) ABSTRACT

Methods and apparatus for evaluating the quality of an environment or process by measuring light emitted from a bioluminescent sample containing ATP, ADP, or alkaline phosphatase. The apparatus comprises a sample collection and analysis system used to collect a sample, mix reagents, react the sample, and collect it in a measurement chamber. The system includes an instrument having a photon detection assembly for use with the sample testing device and one or more probe assemblies that optically cooperate with the instrument. The instrument includes a dark chamber with a reflective interior surface which may be concave or preferably spherical, and a photon detection sensor such as a multi-pixel photon counter sensor. A substantially transparent portion of the probe assembly, and liquid contained therein, focus bioluminescence toward the photon detection sensor.

34 Claims, 37 Drawing Sheets

(51) Int. Cl.
*B01L 3/00* (2006.01)
*G01N 21/76* (2006.01)
*G01N 21/01* (2006.01)

(52) U.S. Cl.
CPC ... *B01L 2300/168* (2013.01); *B01L 2400/0683* (2013.01); *G01N 21/0303* (2013.01); *G01N 21/94* (2013.01); *G01N 2021/0307* (2013.01); *G01N 2201/0221* (2013.01)

(56) References Cited

U.S. PATENT DOCUMENTS

| | | | |
|---|---|---|---|
| 4,039,259 A | 8/1977 | Saito et al. | |
| 4,112,070 A | 9/1978 | Harmening | |
| 4,150,950 A | 4/1979 | Takeguchi et al. | |
| 4,213,703 A | 7/1980 | Haunold et al. | |
| 4,353,868 A | 10/1982 | Joslin et al. | |
| 4,409,988 A | 10/1983 | Greenspan | |
| 4,586,818 A | 5/1986 | Lohr | |
| 4,604,360 A | 8/1986 | Hounsell | |
| 4,653,510 A | 3/1987 | Koll | |
| 4,685,059 A | 8/1987 | Yamamoto | |
| 4,707,450 A | 11/1987 | Nason | |
| 4,730,933 A | 3/1988 | Lohr | |
| 4,752,449 A | 6/1988 | Jackson et al. | |
| 4,755,055 A | 7/1988 | Johnson et al. | |
| 4,770,853 A | 9/1988 | Bernstein | |
| 4,804,845 A * | 2/1989 | Takeuchi | 250/367 |
| 4,813,432 A | 3/1989 | Saint-Amand | |
| 4,978,504 A | 12/1990 | Nason | |
| 5,043,141 A | 8/1991 | Wilson et al. | |
| 5,086,233 A | 2/1992 | Stafford et al. | |
| 5,100,028 A | 3/1992 | Seifert | |
| 5,108,175 A | 4/1992 | Whitlock | |
| 5,139,745 A | 8/1992 | Barr et al. | |
| 5,238,649 A | 8/1993 | Nason | |
| 5,266,266 A | 11/1993 | Nason | |
| 5,316,726 A * | 5/1994 | Babson et al. | 422/65 |
| 5,510,895 A * | 4/1996 | Sahagen | 356/436 |
| 5,558,986 A | 9/1996 | Lundin | |
| 5,624,810 A | 4/1997 | Miller et al. | |
| 5,624,815 A | 4/1997 | Grant et al. | |
| 5,637,874 A | 6/1997 | Honzawa et al. | |
| 5,674,742 A | 10/1997 | Northrup et al. | |
| 5,735,387 A | 4/1998 | Polaniec et al. | |
| 5,783,399 A | 7/1998 | Childs et al. | |
| 5,798,263 A * | 8/1998 | Wood et al. | 435/288.7 |
| 5,827,675 A | 10/1998 | Skiffington et al. | |
| 5,836,692 A | 11/1998 | Pompei | |
| 5,905,029 A | 5/1999 | Andreotti et al. | |
| 5,916,802 A | 6/1999 | Andreotti | |
| 5,917,592 A | 6/1999 | Skiffington | |
| 5,918,259 A | 6/1999 | Squirrell | |
| 5,919,647 A | 7/1999 | Hiramatsu et al. | |
| 5,962,247 A | 10/1999 | Foote et al. | |
| 5,965,453 A | 10/1999 | Skiffington et al. | |
| 5,970,804 A | 10/1999 | Robbat, Jr. | |
| 6,043,047 A | 3/2000 | Foote et al. | |
| 6,055,050 A | 4/2000 | Skiffington | |
| 6,180,395 B1 | 1/2001 | Skiffington et al. | |
| 6,197,254 B1 | 3/2001 | Silver et al. | |
| 6,218,176 B1 | 4/2001 | Berthold et al. | |
| 6,438,279 B1 | 8/2002 | Craighead et al. | |
| 6,653,147 B2 | 11/2003 | DiCesare | |
| 6,924,498 B2 | 8/2005 | Feldsine et al. | |
| 7,030,403 B2 | 4/2006 | Feldsine et al. | |
| 7,399,984 B2 | 7/2008 | Feldsine et al. | |
| 7,544,961 B2 | 6/2009 | Feldsine et al. | |
| 2001/0046687 A1 | 11/2001 | DiCesare | |
| 2002/0009395 A1* | 1/2002 | Hirono et al. | 422/67 |
| 2003/0039384 A1 | 2/2003 | Bacus et al. | |
| 2003/0209653 A1 | 11/2003 | Feldsine et al. | |
| 2004/0030535 A1 | 2/2004 | Johnson et al. | |
| 2011/0091355 A1 | 4/2011 | Noda et al. | |
| 2011/0242535 A1 | 10/2011 | Fröse | |

FOREIGN PATENT DOCUMENTS

| | | |
|---|---|---|
| AU | 2007216739 A1 | 10/2007 |
| CA | 2 469 025 A1 | 6/2003 |
| CA | 2 482 645 A1 | 11/2003 |
| EP | 0 717 840 B1 | 11/1998 |
| EP | 1 028 312 A1 | 8/2000 |
| EP | 0 718 622 B1 | 5/2003 |
| EP | 1 455 177 A2 | 9/2004 |
| EP | 1 455 178 A2 | 9/2004 |
| GB | 2 281 966 A | 3/1995 |
| GB | 2 331 581 A | 5/1999 |
| GB | 2 407 638 A | 5/2005 |
| JP | 62-008040 A | 1/1987 |
| JP | 8-136541 A | 5/1996 |
| JP | 8-285777 A | 11/1996 |
| JP | 9-28372 A | 2/1997 |
| JP | 11-347105 A | 12/1999 |
| JP | 11-514849 A | 12/1999 |
| JP | 2000-225494 A | 8/2000 |
| JP | 2000-510592 A | 8/2000 |
| JP | 2000-356635 A | 12/2000 |
| JP | 2006-502376 A | 1/2006 |
| WO | 80/00188 A1 | 2/1980 |
| WO | 90/04775 A1 | 5/1990 |
| WO | 95/07457 A2 | 3/1995 |
| WO | 95/25948 A1 | 9/1995 |
| WO | 97/23596 A1 | 7/1997 |
| WO | 98/38493 A1 | 9/1998 |
| WO | 99/19709 A1 | 4/1999 |
| WO | 99/31218 A1 | 6/1999 |
| WO | 00/36139 A1 | 6/2000 |
| WO | 00/40748 A1 | 7/2000 |
| WO | 00/42419 A1 | 7/2000 |
| WO | 01/38846 A1 | 5/2001 |
| WO | 01/75439 A2 | 10/2001 |
| WO | 03/050513 A2 | 6/2003 |
| WO | 03/091714 A1 | 11/2003 |
| WO | 2012/079103 A2 | 6/2012 |

OTHER PUBLICATIONS

BioControl® Systems, Inc., Example Spreadsheet, 2000, 4 pages.
BioControl® Systems, Inc., "Lightning®—Installation Guide," 2000, 6 pages.
European Search Report, dated Aug. 9, 2007, for Application No. 04013792.9, 3 pages.
European Search Report, dated Aug. 9, 2007, for Application No. 04013791.1, 3 pages.
Feldsine et al., "Sample Collection and Testing System," filed Dec. 5, 2002, for U.S. Appl. No. 10/314,482, 54 pages.
Gordon et al., "Sample Collection and Bioluminescent Analysis System," filed Jun. 29, 2012, for U.S. Appl. No. 61/666,637, 104 pages.
IDEXX Laboratories, Inc., "Lightning® Index™ Proficiency Program," prior to Feb. 2000, 1 page.
IDEXX Food Safety Net Services, Inc., "Lightning Index™ Reports," prior to Feb. 2000, 1 page.
International Search Report, mailed Aug. 22, 2003, for PCT/US02/39236, 6 pages.
International Search Report and Written Opinion, mailed Jun. 24, 2013, for PCT/US2013/029105, 14 pages.
Kelly et al., "Sample Collection and Testing System," filed Dec. 6, 2001, for U.S. Appl. No. 60/338,844, 54 pages.
Kelly et al., "Sample Collection and Testing System," filed Apr. 24, 2002, for U.S. Appl. No. 60/375,570, 73 pages.
"Leading Portable Monitor," *International Food Hygiene* 10(8), Jan./Feb. 2000, 1 page.
"Lecture on HACCP System for Food Industry in Japan(22): Approval System and Practical Procedure for Manufacturing Process Under Comprehensive Hygienic Control. 9. Practice of Measurement Instruments Effective for Monitoring of Control Standard," *Journal of Antibacterial and Antifungal Agents* 27(9):615-620, 1999.

(56) References Cited

OTHER PUBLICATIONS

*Measurement Technique* 29(6):1-4, 2001, 5 pages.
"Trust to Lightning," *International Food Hygiene* 10(8), Mar. 2000, 1 page.
Written Opinion, mailed Mar. 22, 2004, for PCT/US02/39236, 5 pages.
Supplementary Partial European Search Report, dated for Mar. 9, 2016 for European Application No. 13 81 0675, 5 pages.
Communication pursuant to Rule 164(1) EPC, dated Mar. 17, 2016 for European Application No. 13810675.2-1554 / 2867654, 2 pages.
Office Action, mailed Apr. 29, 2016, for corresponding Mexican Application No. MX/a/2015/000219, 5 pages. (with English Translation).

* cited by examiner

SAMPLE COLLECTION AND BIOLUMINESCENT ANALYSIS SYSTEM

BACKGROUND

1. Field

The disclosure is related to the field of environmental testing; for example, the testing of food, materials, surfaces, and/or equipment, for instance surfaces or equipment with which food comes into contact during preparation or processing.

2. Description of the Related Art

Safety in the food industry is of growing concern. In recent years, approaches to monitoring and controlling contamination and hygiene, have increasing employed HACCP (Hazard Analysis and Critical Control Point) principles. Such approaches are not only directed at controlling the occurrence of pathogenic microorganisms, but are also directed at preventing hazards before these hazards become widespread and expensive problems. HACCP is the science-based system accepted internationally for ensuring food safety. HACCP has been adopted by the FDA and USDA as well as by other countries. HACCP has been endorsed by the National Academy of Sciences, the Codex Alimentarius Commission (an international food standard-setting organization), and the National Advisory Committee on Microbiological Criteria for Foods. Developed over 40 years ago for the space program, HACCP has proven to be effective to ensure that food safety hazards are controlled to prevent unsafe food from reaching the consumer.

In the United States alone, since 1995, HACCP-based systems have been mandated for the following industries by the Federal Government:

Seafood—(21 C.F.R. Parts 123 and 1240 Procedures for the Safe and Sanitary Processing and Importing of Fish and Fishery Products; Final Rule) in December, 1995

Meat and Poultry—(9 C.F.R. Part 304, et al, Pathogen Reduction: Hazard Analysis and Critical Control Point (HACCP) Systems; Final Rule) in July, 1996

Fruit and Vegetable Juice—(21 C.F.R. Part 120: Hazard Analysis and Critical Control Point (HACCP); Procedures for the Safe and Sanitary Processing and Importing of Juice; Final Rule) in January, 2001.

Reliance on HACCP will continue for the foreseeable future.

In order for a food manufacturer or handler to effectively comply with HACCP-based requirements or standards, it is vital that the food manufacturer or handler have an effective system in place to collect, monitor, and analyze relevant HACCP data. The necessity for this can be seen by examining the seven HACCP principles required for compliance:

1. Conduct a hazard analysis.
2. Determine the critical control points (CCP). A CCP is a point, step or procedure in a food process where a number of possible measurement controls can be applied and, as a result, a food safety hazard can be prevented, eliminated, or reduced to acceptable levels.
3. Establish measurement parameters and critical limits for each CCP and identify methods for measuring the CCP. For example, compliance with a cooking CCP may be assessed by the combination of two indicators: time and temperature.
4. Monitor the CCP to ensure ongoing compliance with established critical limits. A monitoring system should not only detect individual deviations, but also analyze data to identify patterns of deviation that could indicate a need to reassess the HACCP plan.
5. Establish corrective actions to be taken when monitoring of important parameters shows that a critical limit has not been met.
6. Maintain accurate records. Effective record keeping is a requirement. HACCP records must be created at the time events occur and include the parameter measurement, date, time and the plant employee making the entry.
7. Verify that the system is working properly initially as well as ongoing. These activities include calibration of the monitoring equipment, direct observations of the monitoring activities and a review of the records.

One essential characteristic of the HACCP system that differentiates it from previous inspection system(s) is that it places responsibility for food safety directly on the food manufacturer or handler. Each food processor or handler must be able to identify CCPs, measure a variety of parametric indicators for each CCP (e.g., time and temperature measurements to verify a cooking process), identify deviations, perform trend analysis of deviations, and document the data to show compliance with the HACCP requirements.

It is not surprising that the growing reach of HACCP-based systems is progressing concurrently with a trend toward methods of testing that are improved by being more rapid, more sensitive and easier to perform. More stringent standards, such as those associated with HACCP-based systems, are expected to motivate such improvements in methods of testing. The reverse is also true in that as test methods improve, standards are likely to become more stringent, since compliance can be more accurately, precisely, and efficiently maintained and verified.

This trend toward improved testing is occurring in a wide variety of industries, including, but not limited to, those industries related to food, pharmaceuticals, cosmetics, and medical areas. In such industries, many techniques are used to monitor levels of environmental quality, including techniques that use microbiological cultures. Microbiological cultures are a most widely conducted test method, but due to their low-test throughput capacity and long incubation time periods, are of limited use. They cannot measure the quality of the environment immediately prior to commencement of an operation. A variety of tests have been developed which detect and in some cases quantify specific pathogens. They can range from high-throughput automated systems to single-sample test devices. These methods require the growth of microorganisms for detection, which consumes considerable time. Monitoring levels of adenosine triphosphate (ATP), adenosine diphosphate (ADP), and alkaline phosphatase (AP), make use of parameters that indirectly correlate to the level or degree of environmental contamination. Still others monitor factors related to risk of the presence and propagation of microorganisms, i.e., temperature, pH, conductivity and protein residues. The latter types of methods are usually real-time in their determinations, offering a distinct advantage for the user in obtaining critical environmental quality information on an immediate basis.

Typically, bioluminescent techniques are used to detect the presence of ATP and AP and similar targets. The protocol involves using a device (e.g. swab) to collect a sample from a surface of interest, and activation of the device to mix reagents together with the sample to produce light proportional to the amount of ATP/AP sampled. The reaction is then read by inserting the device into a photon measuring instrument.

One bioluminescent ATP monitoring system is the LIGHTNING system developed by IDEXX LABORATORIES. The device contains a pre-moistened swab, buffer in a bulb at one end and lyophilized reagent in a foil sealed compartment at the reading end. The swab is removed from the device, used to collect a sample from a test surface, and returned to the tube of the device. The bulb is then bent to break open a snap valve, which releases the buffer into the reading chamber when the bulb is squeezed. The sample-containing swab is then pushed through a foil barrier, the device is shaken and the reaction proceeds between ATP on the swab and the dissolved (in the buffer) reagent. The device is inserted into the reading chamber of the photon measuring instrument and a reading is taken over a ten-second integration period. The intensity of the bioluminescent signal is proportional to ATP on the swab.

Another system is called the CHARM SCIENCES POCKETSWAB PLUS. It is an integrated device used with a LUMINATOR T portable luminometer. The device contains a pre-moistened swab. It is removed from the device base, used to swab a surface, returned to the base, then activated by screwing the top portion relative to the base. This action causes the swab tip to puncture separation barriers allowing separate reagents to migrate to the bottom chamber of the base, mixing and reacting with the sample collected on the swab. Shaking is required to facilitate reagent transfer to the bottom and mixing in the bottom chamber. The activated device is then inserted into a hole in the top of the luminometer and pushed down until it meets a stop. This process displaces a door. The upper portion of the device remains exterior to the instrument, but forms a seal with the reading chamber orifice. A read button in the instrument is then pressed to initiate a signal integration period before a reading is displayed in relative light units (RLU).

Another such system is the BIOTRACE CLEAN-TRACE RAPID CLEANLINESS TEST self-contained device for use with the UNI-LITE XCEL portable luminometer. It also has a pre-moistened swab, which is removed, a sample is collected, and the swab returned. Activation involves forcing the top portion of the device, which contains the sample, down into the base, through membrane barriers. The swab engages a piercing tip, which breaks the membranes and allows the reagents to mix in a manner similar to that of the CHARM device. Shaking is required to transfer all of the solution to the bottom. The BIOTRACE luminometer has a cap, which lifts and swivels out of the way to expose the reading chamber. The sample-containing device is lowered into the chamber and the cap is closed. Full closure of the cap opens a light blocking member to allow signal measurement. Like the CHARM unit, a button begins the read cycle, which ends with the light reading display in RLUs.

MERCK also offers a Another hygiene monitoring system for ATP that is the HY-LITE Monitor by MERCK which employs HY-LITE test swabs, rinse tubes and sampling pens. The swab is moistened in the rinse tube. A surface is swabbed. The swab is returned to the tube and rotated for several seconds to release any collected ATP. The swab is squeezed out and removed. Then the pen is inserted for one second to pick up the sample. The tip of the pen is struck on a hard pad to engage the cuvette. A button is pushed to release the reagents and initiate the reaction in the cuvette. The cuvette is then removed and shaken, it is inserted into the monitor's reading chamber, and a button is pressed to initiate a ten-second light integration period. RLUs are then displayed on the monitor screen.

A similar system has been developed by CELSIS called the SYSTEMSURE portable hygiene monitoring system. The test sequence is similar to that of the MERCK system where the swab is moistened and the surface is swabbed. The reagent is then pipetted into the cuvette. The swab is inserted into the cuvette and rotated for several seconds, then removed. The cuvette is capped and inserted into the luminometer, where the reading is initiated.

There is a need for an improved method and apparatus that is designed to enhance ease of use and to improve measurement accuracy and precision. Many of the current systems incorporate unnecessary actions by the operators that are burdensome with respect to certain steps such as pre-moistening, pipetting, rotating, two-handed screwing, two-handed pushing, striking, shaking, and precise timing, which do not adequately control device activation and contribute to increased reading variances. Many of the current systems are slow in operation and may not be able to produce highly accurate results. Such systems may also consume a relatively large amount of electrical power, thus may not be suitable for convenient mobile use.

The present application describes various methods and apparatus which may address limitations of existing systems.

BRIEF SUMMARY

This application is directed toward various embodiments of a sample collection and analysis system. The system comprises a sample collection and analysis instrument and sample holder or probe which holds disposable test swabs that, when used together, are able to efficiently, accurately, and precisely monitor, quantify, record, and track biological contamination within a process or environment using the bioluminescent properties of biological materials collected via the test swabs. The instrument comprises a photon detection assembly (e.g., multi-pixel photon counter) to measure bioluminescence. The photon detection assembly is communicably coupled to a control system (e.g., logic boards) with a controller (e.g., microprocessor, digital signal processor, application specific integrated circuit, programmable gate array, programmed logic controller), nontransitory computer- or processor-readable storage media (e.g., volatile memory, nonvolatile memory, read only memory, random access memory), and user interface (UI). The UI provides an intuitive, easy to use, operator interface for example via a graphical user interface (GUI). A test swab is used to obtain a known-volume environmental sample and then placed within a probe assembly including one or more reagents that extract the ATP from any cells present in the environmental sample. The detected bioluminescence from the sample indicates biological contamination and provides a qualitative indication of the level of biological contamination present on the test swab. The system provides an integrated, self-contained test device for sample collection and luminescence reading using the photon detection assembly. Various embodiments of methods for employing the embodiments of the instrument and sample holder or probe assembly are also subjects of the present application.

The instrument can operate as a luminometer for taking light readings of samples contained in sample a holder or probe assembly. A unique dark chamber assembly design enhances or increases the detection of illumination emitted by samples, providing for higher accuracy in results. A unique probe design may synergistically cooperate with the design of the dark chamber assembly to further improve optical analysis of samples and accuracy of results. Various security features that prevent or inhibit the use of non-conforming sample holders or probe assemblies with the instrument ensure that the synergistic effect is achieved. The configuration of the sample holder or probe assembly and the manner in which the sample holder or probe assembly is sealed within the dark chamber assembly prevents the photon detection assembly or photo-responsive sensor thereof from being exposed to external photons. This is important for signal stability and to reduce increased background photon counts, which is a primary source of decreased system sensitivity. The design also minimizes other possible sources of thermal and/or electrical noise.

The instrument may include one or more communications ports that allow the instrument to communicate with one or more external devices, for example a network connected computer. Such ports may be wired or wireless ports, and permit the export of analytical data collected by and stored within a non-transitory memory in the instrument. Such ports also allow the import of software and/or firmware updates of the instrument, for example as downloadable files from a Website.

The instrument may provide an intuitive graphical user interface (GUI), facilitating use. The instrument employs a handheld device format, with a relatively low power consumption to allow convenient use in busy environments without constantly needing to be recharged.

The sample holder or probe assembly, in one embodiment, may include a reagent chamber that can be positioned to rupture or otherwise breach and release one or more reagents contained therein into a fluid conduit of the probe assembly. The reagents react with any biological material present in the test swab. The reagents may, for example, be stored in a sealed containment chamber or reservoir that is ruptured or breached by forcing the chamber onto a piercing tip. The reagent solution flows through a sample containing swab tip, causing the sample to be released into the reagent. The reagent then reacts with the sample and emits light proportional to the level of environmental contamination, by, but not limited to, such materials as ATP, ADP or alkaline phosphatase in the sample, and the reagent chosen for the particular application. A distal end portion of the sample holder or probe assembly can be directly inserted into the dark chamber assembly to measure photons emitted from a bioluminescent sample.

DETAILED DESCRIPTION

This application relates to apparatus and methods for monitoring environmental and process quality that can be used to provide critical information in a wide variety of settings. These settings include, but are not limited to, testing in the food, pharmaceutical, cosmetic, and medical industries. These settings may further include environmental conditioning and control equipment for general usage such as, but not limited to, commercial air conditioning equipment and cooling towers. Additional settings include sensitive environments potentially susceptible to malicious or inadvertent contamination with biological materials, such as military installations, hospitals or enclosed high occupancy buildings.

Drawings depicting certain embodiments are provided for purposes of illustration. Also, the embodiments are described in a context including the monitoring of pathogenic contamination by measuring light emission from a bioluminescent reaction. However, as one skilled in the art will appreciate, various aspects may also be applicable in a variety of other settings. Also, as will be appreciated, equivalent modifications can be made without deviating from the scope or spirit of the invention. Not all such possible modifications have been illustrated or described in order to avoid unnecessary detail that would obscure the description of the various embodiments.

FIGS. 1A and 1B, 2A and 2B, 3A and 3B, and 4 depict four sample collection and analysis instruments, each having different ergonomic housings. The ergonomic size, shape, and profile of the housings permit a user to securely hold the sample collection and analysis instrument in a single hand. Each of the sample collection and analysis instruments has a user interface 102.

Figure 1A:
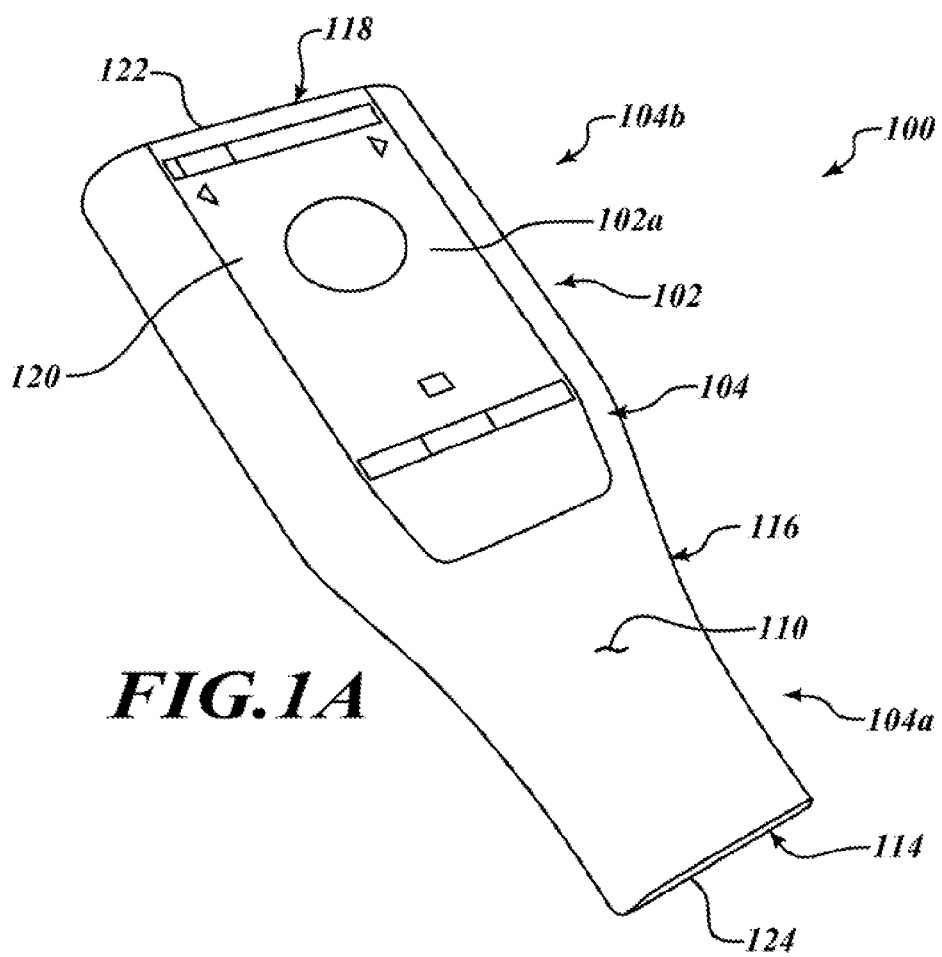
FIGS. 1A and 1B are respectively a perspective view and side plan view of an example sample collection and analysis instrument having an ergonomic size, shape and profile enabling the instrument to be securely held in a single hand according to one illustrated embodiment described herein; along with a portion of a user interface allowing a user to interact with the instrument, for example via a touch-sensitive or touch-responsive input/output device.
Figure 1B:
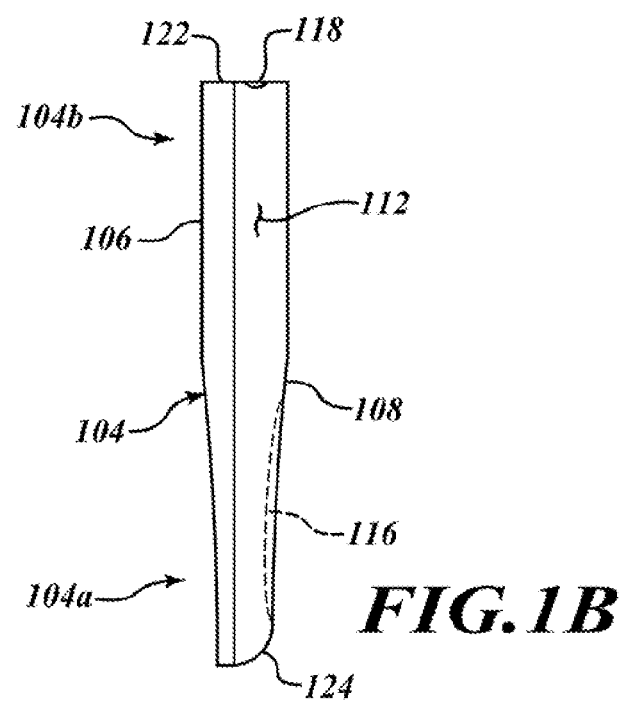

FIGS. 1A and 1B show an example housing 104 with a tapered lower portion 104a sized and dimensioned to be easily held in a single hand and a relative wider upper portion 104b which includes a portion of the user interface 102 in the form of a touch-sensitive or touch-response display 102a. The housing 104 can be a single or multi-piece molded, extruded, or stamped housing, having for example a front portion 106 and a rear portion 108 that are physically coupled using one or more reversible or non-reversible fasteners. One or more plastics, metals, or other similar rigid, impact-resistant materials can be used for all or a portion of the housing 104. A front surface 110 and rear surface 112 of the housing 104 can have one or more textures applied thereto for decorative purposes, or for functional purposes, for example to increase the surface roughness of the system to add slip resistance when the system is held in a single hand. In some instances, the front surface 110 or the rear surface 112 of the housing 104 may have a microbiocidal coating or additive that inhibits biological growth on the system 104. In some instances, the front surface 110 and the rear surface 112 of the housing 104 may be of differing materials or of the same material having differing characteristics. For example, in one embodiment the rear portion 108 of the housing 104 can be a plastic member having a rear surface 112 that is textured to improve slip resistance of the system when it is held by a user. Conversely, the front portion 106 of the housing 104 can be a metal member having a front surface 110 that is smooth to improve appearance and cleanliness of the instrument 100.

The terms "front," "rear," "top," "bottom," and other like terms used herein refer to positions relative to each other and are not intended, nor should be interpreted, to denote a particular absolute direction or spatial orientation. For example, a feature described as being on the "bottom" surface of a device could be on the "top" surface or a "side" surface of the device if the device is rotated or inverted; such rotation or inversion is envisioned to be within the scope of one or more claimed embodiments described herein.

Although only one touch-sensitive or touch-responsive display 102a is shown in FIG. 1A, the user interface 102 may include any number of output devices such as lamps, indicators, screens, displays, gauges, and the like. The user interface 102 can also include any number of input devices such as buttons, knobs, switches, capacitive devices, pulse wheels, potentiometers, touch-screens, and the like. As shown in FIG. 1A, in some instances the user interface 102 can include at least one capacitive or resistive touch-sensitive or touch-responsive display 102a as both an input and output (I/O) device. Such I/O devices advantageously reduce the number or size of penetrations through housing 104, thereby reducing the number of avenues for liquid intrusion into the housing 104. A flexible membrane 120 may be disposed proximate and used to seal all or a portion of the user interface 102 from the external environment. In at least some instances, such as when a touch-sensitive or touch-responsive display 102a is used, a sealed, optically transparent, flexible membrane 120 may be disposed across all or a portion of the touch-sensitive or touch-responsive display 102a. Although shown only on the front portion 106 of the housing 104, in some instances, the user interface 102 may extend to the rear portion 108 of the housing 104. For example, a battery level indicator in the form of multiple illuminated elements may be located on the rear portion of the housing 104.

The housing 104 shown in FIGS. 1A and 1B is a generally rectangular member having one or more rounded lateral edges. The housing 104 is thicker in the upper region 104b occupied by the touch-sensitive or touch-responsive display 102a and tapers both in width and thickness towards the lower region 104a of the housing 104 that is grasped in a user's hands. The transition between the thicker portion 104b of the housing 104 containing the touch-sensitive or touch-responsive display 102a and the thinner portion 104b of the housing 104 is strongly tapered, providing a frontal profile reminiscent of an inverted traditional "milk bottle." A material having a first set of properties including material, color, and surface finish (e.g., a fine textured, white colored, injection molded plastic) forms the front portion 106 at least partially surrounding the touch-sensitive or touch-responsive display 102a to provide a high degree of contrast between the touch-sensitive or touch-responsive display 102a and the front surface 110. A material having a second set of properties including material, color, and surface finish (e.g., a medium textured, grey colored, injection molded plastic) forms the entire rear portion 108. The "top" and the "bottom" of the housing 104 are at substantially 90° with respect to the front surface 110 and the rear surface 112 of the housing 104. In at least some instances, a hinged member (not visible in FIG. 1) may be attached to the rear portion 106 to provide a prop-stand for the instrument 100.

One or more ports, apertures, or openings may be disposed about the housing 104, for example on the housing bottom 124. One or more communications ports 114 may be disposed in, on, or about the housing 104. Such communications ports 114 may be useful in communicably coupling the instrument 100 to an external device such as a personal computer or an external communications network. The communications port(s) 114 can, in some instances, have a proprietary interface configuration or communications protocol such that an adapter is needed to bridge from the communications port(s) 114 to a computer or network connection. The communications port 114 can, in other instances, have one or more industry recognized interface configurations or communications protocols, for example Universal Serial Bus (USB), IEEE 1394 ("FireWire®"), Thunderbolt®, RS-232, or the like. The communications port(s) 114 may be partially or completely sealed or otherwise obstructed with a displaceable member, for example an elastomeric diaphragm or cover, to reduce the likelihood of dust or liquid intrusion into the communications port(s) 114 or the housing 104. In at least some instances, the communications port(s) 114 is used for providing input data to the instrument 100, for example system configuration information, calibration information, operating system updates, system time and date updates, etc. In at least some instances, the communications port(s) 114 may also be useful for obtaining output data from the instrument 100, for example analytical results and corresponding test dates, times, and locations that are stored within an on-board memory in the instrument 100.

One or more battery compartments 116 may be disposed in, on, or about the instrument 100. For example, one or more battery compartments 116 may be disposed on the rear portion 108 of the housing 104. The instrument 100 may use replaceable, standard, chemical battery cells, for example "AAA," "AA," or "C" size batteries. In some instances the system may instead use one or more secondary (i.e., rechargeable) chemical battery cells, for example one or more nickel/cadmium, nickel metal hydride, or lithium ion power cells. Where secondary or rechargeable chemical battery cells are used, the instrument 100 may be equipped with one or more power adapter ports and an internal or external power converter useful for replenishing the charge in the secondary or rechargeable chemical battery cells. Alternatively or additionally, other types of power sources or cells may be employed as on-board power sources, for instance fuel cells or super- or ultra-capacitor cells.

One or more user accessible probe insertion ports or entrances 118 sized and dimensioned to accommodate a passage of a sample holder or probe assembly (not shown in FIGS. 1A and 1B) are disposed on the housing 104, for example on a top 122 of the housing 104. The probe insertion port(s) or entrance(s) 118 may include a cover member (not clearly visible in FIGS. 1A and 1B) that selectively substantially covers the probe insertion port(s) or entrance(s) 118 to prevent light from entering. The probe insertion port(s) or entrance(s) 118 selectively provide access to a dark chamber assembly located internal to the instrument 100 and illustrated and discussed in detail below, for example with reference to FIGS. 6-12.

Figure 2A:
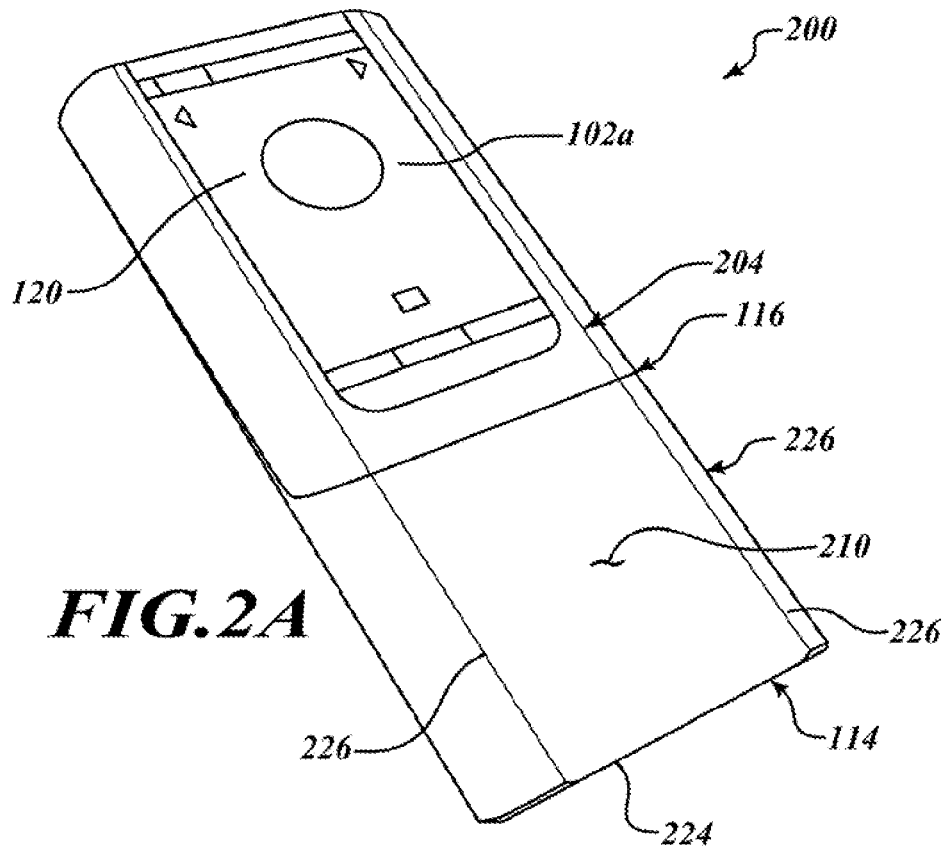
FIGS. 2A and 2B are respectively a perspective view and side plan view of an example sample collection and analysis instrument having an ergonomic size, shape, and profile according to another illustrated embodiment described herein; along with a portion of a user interface allowing a user to interact with the instrument, for example via a touch-sensitive or touch-responsive input/output device.
Figure 2B:
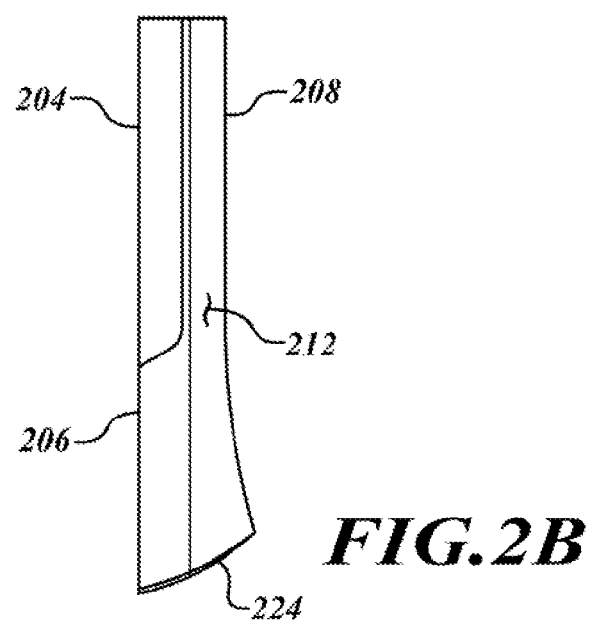

FIGS. 2A and 2B show another example of an instrument 200 having a housing 204. The housing 204 can be a single piece or multi-piece molded, extruded, or stamped housing, having for example a front portion 206 and a rear portion 208. The front portion 206 and the rear portion 208 are physically coupled together using one or more removable or non-removable fasteners that are inserted through the rear portion 208 and are consequently visible only in FIG. 2B. One or more plastics, metals, or other similar rigid, impact-resistant materials can be used for all or a portion of the housing 204. The front surface 210 and the rear surface 212 of the housing 204 can have one or more textures applied thereto for decorative purposes or for functional purposes, for example to increase the surface roughness of the system 200 or add texture to the instrument 200 such that the instrument 200 can be securely held or gripped using only one hand. A coating or additive containing one or more biocides or similar materials useful for inhibiting biological growth may be added to or incorporated into the front surface 210 or the rear surface 212 of the housing 204. In some instances, the front surface 210 and the rear surface 212 of the housing 204 may be of differing materials or of the same material having differing characteristics such as color or texture. For example, in one embodiment the rear portion 208 of the housing 204 can be a plastic member having a rear surface 212 that is textured to facilitate gripping of the instrument 200. Conversely, the front portion 206 of the housing 204 can be a metal member having a front surface 210 that is smooth to improve appearance and cleanliness of the instrument 200.

A flexible membrane 120 may be disposed proximate, and used to seal, all or a portion of a touch-sensitive or touch-responsive display 102a. Although shown only on the front portion 206 of the housing 204, in some instances, the user interface 102 may extend to the rear portion 208 of the housing 204. For example, a battery level indicator in the form of multiple illuminated elements may be located on the rear portion of the housing 204.

The housing 204 shown in FIGS. 2A and 2B is a generally rectangular member having one or more rounded edges. The housing 204 is thicker in the region grasped in a user's hands, and tapers to a thinner cross section in the region occupied by the touch-sensitive or touch-responsive display 102a. The touch-sensitive or touch-responsive display 102a may optionally be disposed within a recess that runs longitudinally (i.e., from top to bottom) along the front portion 206 of the housing 204, creating two substantially parallel ridges 226 on the front surface 210. A material having a first set of properties including material, color, and surface finish (e.g., a fine textured, white colored, injection molded plastic) forms the front portion 206 surrounding the touch-sensitive or touch-responsive display 102a, providing a high degree of contrast between the touch-sensitive or touch-responsive display 102a and the front surface 210. A material having a second set of properties including material, color, and surface finish (e.g., a medium textured, grey colored, injection molded plastic) forms the remaining front portion 206 and the entire rear portion 208. The housing top 222 substantially forms a 90° angle with respect to both the front portion 206 and the rear portion 208. Conversely, the housing bottom 224 defines an arc extending from the front portion 206 to the rear portion 208.

Figure 3A:
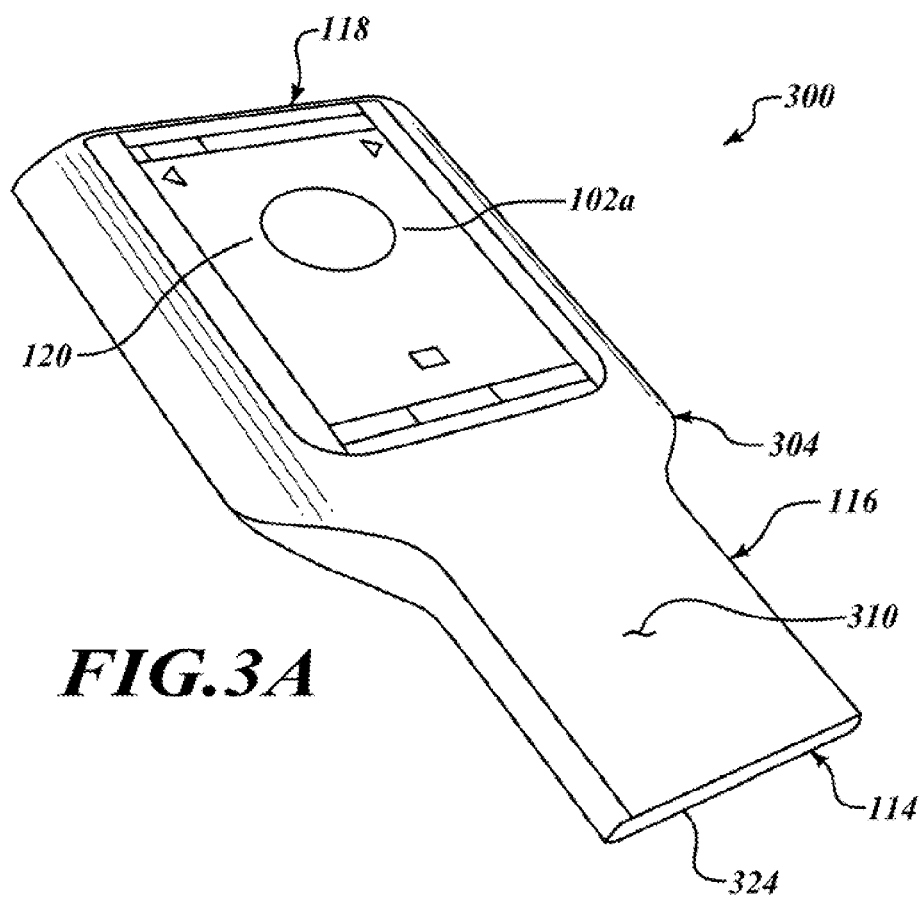
FIGS. 3A and 3B are respectively a perspective view and side plan view of an example sample collection and analysis instrument having an ergonomic size, shape, and profile according to yet another illustrated embodiment described herein; along with a user interface allowing a user to interact with the instrument, for example via a touch-sensitive or touch-responsive screen input/output device.
Figure 3B:
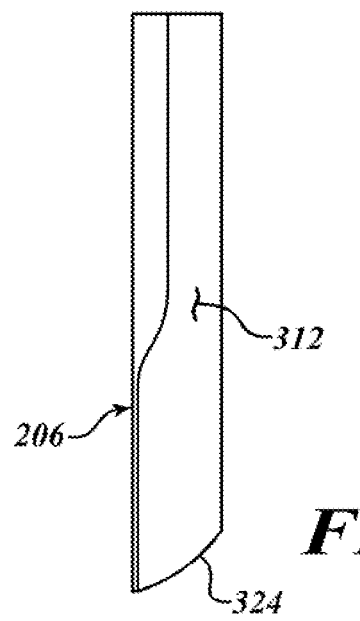

FIGS. 3A and 3B show another example instrument 300 having a housing 304 at least partially surrounding a touch-sensitive or touch-responsive display 102a. The housing 304 can be a single piece or multi-piece molded, extruded, or stamped housing, having for example a front portion 306 and a rear portion 308 that are physically coupled together using one or more reversible or non-reversible fasteners. One or more plastics, metals, or other similar rigid, impact-resistant materials can be used for all or a portion of the housing 304. The front surface 310 and the rear surface 312 of the housing 304 can have one or more textures applied thereto for decorative purposes or for functional purposes, for example to increase the surface roughness of the instrument 300 to add texture such that the instrument 300 may be held or gripped using only a single hand. A coating or additive containing one or more biocides or similar materials useful for inhibiting biological growth may be added to or incorporated into the front surface 310 or the rear surface 312 of the housing 304. In some instances, the front surface 310 and the rear surface 312 of the housing 304 may be of differing materials or of the same material having differing characteristics such as color or texture. For example, in one embodiment the rear portion 308 of the housing 304 can be a plastic member having a rear surface 312 that is textured to improve slip resistance of the instrument 300 when held by a user. Conversely, the front portion 306 of the housing 304 can be a metal member having a front surface 310 that is smooth to improve appearance and cleanliness of the instrument 300.

A flexible membrane 120 may be disposed proximate and used to seal all or a portion of a touch-sensitive or touch-responsive display 102a. Although shown only on the front portion 306 of the housing 304, in some instances, a portion of the user interface 102 may extend to the rear portion 308 of the housing 304. For example, a battery level indicator in the form of multiple illuminated elements may be located on the rear portion of the housing 304.

The housing 304 shown in FIGS. 3A and 3B is a generally rectangular member having one or more rounded edges. The housing 304 is thicker in the region of the housing occupied by the touch-sensitive or touch-responsive display 102a and tapers in width towards the region of the housing 304 for grasping in a user's hand. The transition between the thicker portion of the housing 304 containing the touch-sensitive or touch-responsive display 102a and the narrower portion of the housing 304 is sharply tapered, again providing a frontal profile reminiscent of a traditional "milk bottle." A material having a first set of properties including material, color, and surface finish (e.g., a fine textured, white colored, injection molded plastic) forms the front portion 306, providing a high degree of contrast between the touch-sensitive or touch-responsive display 102a and the front surface 310. A material having a second set of properties including material, color, and surface finish (e.g., a medium textured, grey colored, injection molded plastic) forms the rear portion 308. The housing top 322 forms substantially a 90° angle with respect to both the front portion 306 and the rear portion 308. Conversely, the housing bottom 324 defines an arc extending from the front portion 306 to the rear portion 308.

Figure 4:
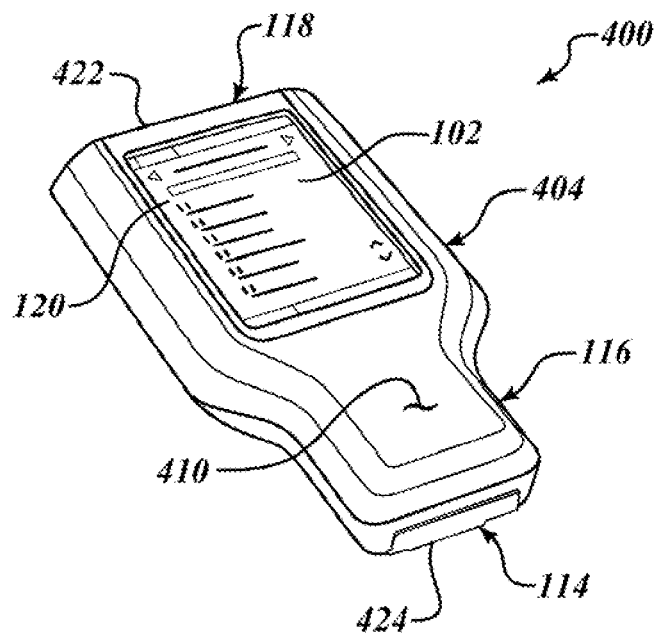
FIG. 4 is a perspective view of an example sample collection and analysis instrument having an ergonomic size, shape, and profile according to still another illustrated embodiment described herein; along with a user interface allowing a user to interact with the system controller, for example via a touch-sensitive or touch-responsive input/output device.

FIG. 4 shows yet another example instrument 400 having a housing 404 which at least partially surrounds a touch-sensitive or touch-responsive display 102a. The housing 404 can be a single piece or multi-piece molded, extruded, or stamped housing, having a front portion 406 and a rear portion 408 that are physically coupled together using one or more fasteners. One or more plastics, metals, or other similar rigid, impact-resistant materials can be used for all or a portion of the housing 404. The front surface 410 and the rear surface 412 of the housing 404 can have one or more textures applied thereto for decorative purposes or for functional purposes, for example to increase the surface roughness of the system 400 to facilitate gripping the instrument 400 using only one hand. A coating or additive containing one or more biocides or similar materials useful for inhibiting biological growth may be added to or incorporated into the front surface 410 or the rear surface 412 of the housing 404. In some instances, the front surface 410 and the rear surface 412 of the housing 404 may be of differing materials or of the same material having differing characteristics such as color or texture. For example, the rear portion 408 of the housing 404 can be a plastic member having a rear surface 412 that is textured to improve slip resistance of the system when held by a user. Conversely, the front portion 406 of the housing 404 can be a metal member having a front surface 410 that is smooth to improve appearance and cleanliness of the instrument 400.

A flexible membrane 120 may be disposed proximate and used to seal all or a portion of the touch-sensitive or touch-responsive display 102a. Although shown only on the front portion 406 of the housing 404, in some instances, a portion of the user interface 102 may extend to the rear portion 408 of the housing 404. For example, a battery level indicator in the form of multiple illuminated elements may be located on the rear portion of the housing 404.

The housing 404 shown in FIG. 4 is a generally rectangular member having one or more rounded edges. The housing 404 is of generally uniform thickness and tapers in width towards the region of the housing 404 configured to be grasped in a user's hand. The transition between the thicker portion of the housing 404 containing the user interface 102 and the narrower portion of the housing 404 is sharply tapered, again providing a frontal profile reminiscent of a traditional "milk bottle." A material having a first set of properties including material, color, and surface finish (e.g., a fine textured, white colored, injection molded plastic) forms the front portion 406, providing a high degree of contrast between the touch-sensitive or touch-responsive display 102a and the front surface 410. A material having a second set of properties including material, color, and surface finish (e.g., a medium textured, grey colored, injection molded plastic) forms the rear portion 408. The housing top 422 forms substantially a 90° angle with respect to both the front portion 406 and the rear portion 408. The housing bottom 424 is chamfered front and rear and forms substantially a 90° angle with respect to both the front portion 406 and the rear portion 408.

Figure 5:
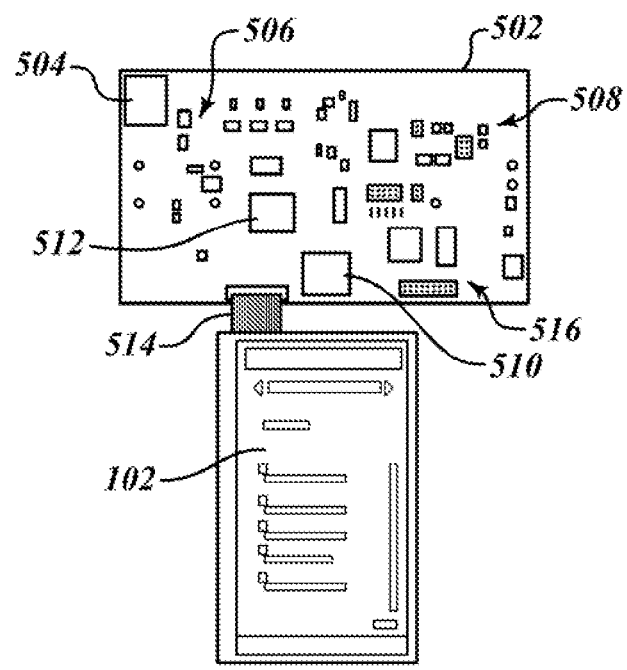
FIG. 5 is a perspective view of an example user interface and logic board assembly of a sample collection and analysis instrument; the user interface may include one or more input systems, such as a touch-sensitive or touch-responsive display, allowing a user to interact with a system controller, to store and retrieve data from a system memory, and to communicate with one or more external devices, according to an illustrated embodiment described herein.

FIG. 5 shows a touch-sensitive or touch-responsive display 102a communicably coupled to a logic board 502. Although pictured as a single printed circuit board in FIG. 5, the logic board 502 can include components spread across any number of communicably coupled separate logic boards. For example, the logic board 502 may include various components (e.g., electrical or electronic components, connectors) and associated conductive paths or traces. The logic board 502 may be partially or completely disposed within the housing 104, 204, 304, 404. The sample collection and analysis system may include at least one processor 504, non-transitory storage media 506, one or more power converters 508, an input/output controller 510, a graphical processing unit 512, and a network interface 516. A photon detector assembly (not shown in FIG. 5) is positioned relative to a dark chamber of a dark chamber assembly (not shown in FIG. 5), for instance partially disposed therein is used for measuring, detecting or otherwise sensing bioluminescence of samples. The photon detector assembly is communicably coupled to the logic board 502 and may, in some instances, also be physically coupled to the logic board 502.

The one or more processors 504 can include one or more devices capable of executing machine executable instructions providing sample testing and analysis functionality to the sample collection and testing instrument 100, 200, 300, 400. In some instances, the one or more processors 504 can include multifunction devices capable of providing input/output, logic, communications, and graphical output, for example a System on a Chip (SoC) or Application Specific Integrated Circuit (ASIC) device. In other instances, the one or more processors 504 may include a plurality of discrete devices, each capable of providing one or more functions such as I/O, logic, communications, and the like. The one or more processors can include one or more single core or multi-core microprocessors, for example an AMD® K8, K10, Bulldozer, or Bobcat series processors; a Qualcomm® Snapdragon series processor; an NVIDIA® Tegra® series processor; or an Intel® x86, Pentium®, or Atom® series processors. The one or more processors 504 may also include one or more programmable gate arrays (PGA); one or more digital signal processors (DSP); one or more reduced instruction set computers (RISC); one or more programmable logic circuits (PLCs), and the like. The use of one or more mobile or low power consumption processors 504 may advantageously increase the battery life of the system. The one or more processors 504 may include a limited amount of non-transitory storage in the form of basic input/output system (BIOS) memory, cache, or other read-only memory containing components such as an operating system and machine executable instructions that when executed by the one or more processors 504 provides sample collection and testing functionality to the system.

The one or more processors 504 can include, or be communicatively coupled to, one or more oscillators and one or more real time clocks (RTC) useful in tracking, organizing and time stamping events such as calibration activities, service or maintenance activities, data collection activities, data logging activities, data transfer activities, communications activities, and the like. The one or more processors 504 can be communicably coupled to the non-transitory storage media 506, the one or more power converters 508, the one or more communications ports 510, and the photon detection assembly using one or more serial or parallel data buses.

The non-transitory storage media 506 can include one or more volatile and/or nonvolatile computer- or processor-readable devices (e.g., memory, spinning media, solid-state media) able to store data. Such devices may include random access memory (RAM) 506a and read only memory (ROM) 506b within the sample collection and testing instrument 100, 200, 300, 400. Such devices may also include one or more removable storage devices 506c such as one or more secure digital ("SD") interfaces able to accommodate the insertion of an SD compliant memory device. In some instances, all or a portion of the data contained in the non-transitory memory within the sample collection and testing instrument 100, 200, 300, 400 can be transferred to a removable storage device communicably coupled to the system.

The non-transitory storage media 506 can include one or more types of magnetic, electroresistive, molecular, or optical storage media including, but not limited to one or more hard disk drives ("HDD"), electrostatic storage media such as solid state drives ("SSD"), electrically erasable programmable read only memory ("EEPROM") and similar current and future storage devices. In addition to storing operating system and machine executable instructions, the non-transitory storage media 506 may also be useful for storing analytical results, test sequences, test points, date and time data, and similar data related thereto. Such data retention can form at least a portion of a hazard analysis critical control point (HACCP) program, for example in a food or pharmaceutical production or preparation facility. The non-transitory storage media 506 can have any storage capacity or physical configuration. In one instance, the total storage capacity may be 1 gigabyte (1 GB) spread across four parallel addressable 256 megabyte (256 MB) board mounted storage devices. Other devices such as single inline memory modules (SIMM), dual inline memory module (DIMM) packages, and other packages and capacities may also be used to provide a degree of system customizability. The total storage capacity of the sample collection and testing instrument 100, 200, 300, 400 can range from about 128 MB to about 512 GB; from about 128 MB to about 512 GB; from about 128 MB to about 256 GB; from about 128 MB to about 128 GB; or from about 128 MB to about 10 GB.

The one or more power converters 508 can include any number of systems or devices suitable for altering or adjusting the voltage, current, or waveform of a power supplied to the sample collection and testing instrument 100, 200, 300, 400 to a different voltage, current, or waveform useful in powering the sample collection and testing system. For example, the one or more power converters 508 may convert 120V, 60 Hz alternating current to 3V direct current used by the processor 504 and photodetector. In some instances, all or a portion of the one or more power converters 508 are disposed within the housing 104, 204, 304, 404, while in other instances all or a portion may be disposed external to the housing, for example in the form of a plug mounted transformer/converter (e.g., a "wall wart" type power supply). In at least some instances, all or a portion of the power provided by the one or more power converters 508 are used to increase the charge on the power storage cells (e.g., rechargeable batteries or the like) in the sample collection and testing instrument 100, 200, 300, 400. The one or more power converters 508 can supply one or more output wave-forms, for example direct current, square wave, sawtooth wave, or any other useful form of power supply. The one or more power converters 508 can supply one or more output voltages, for example 1.5V, 3.0V, 5.0V, 9.0V, or 12V.

The one or more power converters 508 may also include one or more protective devices, for example one or more replaceable or non-replaceable fuses or similar overcurrent protection devices. The one or more power converters 508 may include one or more filtering or regulating devices or systems to reduce the possibility of over/under voltage conditions within the sample collection and testing instrument 100, 200, 300, 400.

Analog and digital data is imported to and exported from the sample collection and analysis system using an I/O controller 510 communicably coupled to the at least one processor 504 and the non-transitory storage media 506 via the bus 524. In addition to receiving input from a touch-sensitive or touch-responsive display 102a, one or more additional input devices may be communicably coupled to the I/O controller 510. In at least some instances, the I/O controller 510 can be communicably coupled to one or more industry recognized serial interfaces, for example a universal serial bus (USB), mini-USB, micro-USB, IEEE 1394, Intel® Thunderbolt®, or any similar current or future serial interface. In at least some instances, the I/O controller can be communicably coupled to one or more wireless interfaces, for example a Bluetooth® wireless interface, a near field communication (NFC) wireless interface, a ZigBee® wireless interface, or any similar current or future wireless interface. In at least some instances, the I/O controller can be communicably coupled to one or more parallel interfaces. In at least some instances, the I/O controller can be communicably coupled to one or more proprietary interfaces having a unique or proprietary connector or pinout configuration.

In at least some instances, the I/O controller 510 can include one or more analytical device ports for connecting one or more external analytical sensors 526 to the sample collection and analysis instrument 100, 200, 300, 400. External analytical devices coupleable to the sample collection and analysis system include, but are not limited to temperature probes, pH probes, dissolved oxygen probes, conductivity probes, and the like. Additional analytical measurements may be collected based, for example, on the facility HACCP plan. The collection of multiple signals from multiple devices using a single system advantageously provides the ability to generate complete HACCP documentation, including biological contamination data and other physical data correlated to each identified critical control point and stored as a logical group within non-transitory storage media 506. Such data can be periodically exported to one or more external devices to provide HACCP documentation. When an external probe is communicably coupled to the system, the touch-sensitive or touch-responsive display 102a can display data relevant to the measurements provided by the external probe. For example, an external pH probe may cause the touch-sensitive or touch-responsive display 102a to display contemporaneously or in a sequential manner the pH sensed using the pH probe and the level of biological contamination detected using the internal photon detection assembly.

The I/O controller 510 may also be used to support additional input or output devices that are physically or logically separate from the user interface 102. In at least some instances, one or more buttons, switches, knobs, dials, or similar tactile input devices may be communicably coupled to the I/O controller 510 instead of, or in addition to, the touch-sensitive or touch-responsive display 102a. Such devices may include, a full or partial keypad (0-9, #, *), function buttons, or a full or partial keyboard (QWERTY, etc.) may be disposed on the system.

In at least some instances, the I/O controller 510 can facilitate the exchange of data between the sample collection and analysis instrument 100, 200, 300, 400 and one or more external devices. For example, the I/O controller 510 may be used to synchronize or otherwise link the sample collection and testing instrument 100, 200, 300, 400 to an external device using a proprietary or USB interface for the purposes of exporting analytical data logged within the non-transitory storage medium 506. Such data export capabilities may advantageously assist in maintaining a cohesive HACCP database on an external device or an external network which provides management or regulatory agency access to the analytical data. In other instances, the I/O controller 510 may be used to synchronize or otherwise link the sample collection and testing instrument 100, 200, 300, 400 to an external device using a USB interface for the purposes of obtaining software updates, firmware updates, operating system updates, data security updates, and the like. In at least some instances, all or a portion of the software, firmware or operating system updates may be downloaded via one or more networks, such as the Internet or World Wide Web, via one or more applications stores or portals.

The graphical processing unit 512 is shown communicably coupled to the touch-sensitive or touch-responsive display 102a via one or more ribbon cables 514 or the like. In some instances, a graphics processing unit 512 may be partially or completely integrated into the at least one processor 504. Although only one touch-sensitive or touch-responsive display 102a is shown coupled to the sample collection and analysis instrument 100, 200, 300, 400, any number of touch-sensitive or touch-responsive display 102a or other user interface elements or devices may be used to provide various outputs to, or collect various inputs from, the user. In at least some instances, the touch-sensitive or touch-responsive display 102a can present output and collect input using a graphical user interface (GUI) that presents and collects at least a portion of the data in the form of images or user selectable icons.

The touch-sensitive or touch-responsive display 102a can include any current or future monochrome or color device having an appropriate physical (e.g., thin) form factor and capable of displaying data such as a liquid crystal display (LCD), a light emitting diode (LED) display, a gas plasma display, an organic LED display, an eInk® display, and the like. One or more other lights, indicators, clear or colored incandescent lamps, clear or colored LEDs, or the like may also be use to indicate power status, charging status, battery level status, communications status, data links, peripheral device status, and the like. One or more different types of user input devices may be used, for example the user may primarily interact with the one or more processors 504 via a touch-sensitive or touch-responsive display 102a, while battery level and communications status are communicated using one or more LEDs. In some instances, the user interface 102 can include a touch-sensitive or touch-responsive display 102a from which the at least one processor 504 receives input via the I/O controller 510.

The network interface 516 may also be communicably coupled to the sample collection and analysis instrument 100, 200, 300, 400. The network interface may include one or more wireless network transceivers or interfaces 516a (e.g., IEEE 802.11 "WiFi," or the like), one or more wired network transceivers or interfaces 516b (e.g., Ethernet or similar), or combinations thereof. In at least some instances, the sample collection and analysis instrument 100, 200, 300, 400 may synchronize or exchange encrypted or unencrypted data with one or more external devices via the network interface 516, for example over a secure or unsecured wireless network connection between the sample collection and analysis instrument 100, 200, 300, 400 and the external device. In some instances, the network interface 516 may include an illuminator (not shown), for example, a laser or a light emitting diode (LED) such as an infrared LED to optically transmit information. Optical data transmission requires line-of-sight between the transmitter and receiver, which may be considered a disadvantage, but may be considered advantageous where security is a concern or where location determination is desirable.

The sample collection and analysis instrument 100, 200, 300, 400 may optionally include a global positioning system (GPS) receiver 522 to receive GPS positioning information from one or more GPS satellites. Such GPS data may be advantageously associated with the location or point of collection of a specific sample. Such data can be associated with analytical results stored within the non-transitory storage medium 506 and can be used to verify the location, time, and date that a particular sample was obtained or a particular analysis performed. As part of an integrated HACCP program, such GPS positional data may advantageously provide additional evidence that samples collected under the auspices of an HACCP program are taken at the correct times and in the correct locations.

The sample collection and testing instrument 100, 200, 300, 400 may be equipped with one or more lighting systems, for example a backlight system, to illuminate the user interface 102 and permit system operation in low ambient light conditions. To permit sample collection in low ambient light conditions, the sample collection and testing instrument 100, 200, 300, 400 may be equipped with an exterior lighting system, for example an LED flashlight or the like.

Figure 6:
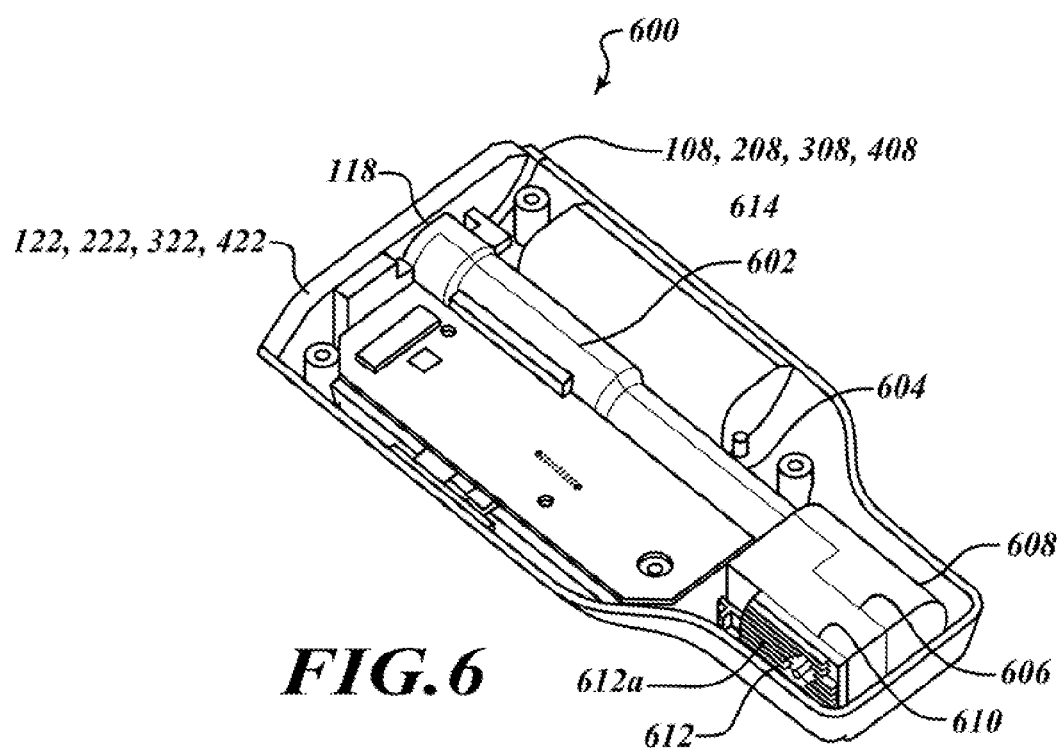
FIG. 6 is a partial sectional view of an example sample collection and analysis instrument that shows a dark chamber assembly including a passage to receive a sample holder or probe assembly, and which terminates at a dark chamber that is physically and optically coupled to a photon detection assembly used for measuring and quantifying the bioluminescence produced by a sample in the dark chamber, according to an illustrated embodiment described herein.

FIG. 6 shows an example sample collection and testing instrument 600 with the front portion of the housing 106, 206, 306, 406 removed to expose at least a portion of the logic board 502 and the dark chamber assembly 602.

The dark chamber assembly 602 includes a sample insertion tube 604 which defines or forms a passage, a dark chamber 606 having an at least partially concave inner surface 608 at a distal end of the sample insertion tube 604 and passage, a photon detection assembly 610, and optionally a heat dissipation assembly 612. A sample holder such as a probe assembly (not shown in FIG. 6) containing a biological sample and one or more reagents is inserted into the passage of the dark chamber assembly 600. The combination of the instrument 100, 200, 300 and 400 and the sample holder or probe assembly comprises a sample collection and testing system. The sample holder or probe assembly typically removably receives swabs, used for sampling surfaces and other objects or materials.

After insertion, a distal portion of the probe assembly which contains a sample or specimen is positioned within the dark chamber 606. Bioluminescence from the sample is reflected and/or focused by the inner surface of the dark chamber toward the photon detection assembly 610, which detects, measurers or otherwise senses one or more characteristics of the bioluminescence, for instance a total level or amount or intensity of light. The photon detection assembly 610 may advantageously employ a multi-pixel photon counter (MPPC, e.g., array of avalanche photodiodes). The photon detection assembly 610 is cooled via the heat dissipation assembly 612 which transports heat away from the photon detection assembly 610 and dissipates the heat.

The sample insertion tube 604 is defined by a generally cylindrical structure having a probe insertion port or entrance 118 disposed proximate the top 122, 222, 322, 422 of the sample collection and testing instrument 100, 200, 300, 400, respectively. The dark chamber 606 is located at the distal end of the sample insertion tube 604, opposite the probe insertion port or entrance 118. The sample collection tube 604 includes a probe insertion port or entrance 118 located at a first end proximate an exterior surface of the housing to accommodate the insertion of a sample holder or probe assembly therein. The sample holder or probe assembly is inserted through the probe insertion port or entrance 118 into the passage. A distal portion of the sample holder or probe assembly, which is optically transparent to at least some wavelengths of interest and which contains at least some of the sample for bioluminescent analysis, is positioned within the dark chamber 606, in a field of view of the photon detector (e.g., MPPC) of the photon detection assembly 610.

The dark chamber assembly 602 can be formed from injection molded, cast, formed, or extruded thermoplastic parts. In some instances, all or a portion of the dark chamber assembly 602 may include a cast or formed metallic structure. Various rings, guides, and stays (not visible in FIG. 6) may be positioned internally, for example within the passage of the dark chamber assembly 602, to accurately, reliably, and reproducibly position the sample holder or probe assembly therein. Some or all of the rings, guides, or stays may limit the type, number, or physical configuration of the sample holders or probe assemblies that can be receive into the passage of the dark chamber assembly 602. For example, some or all or the rings, guides, or stays within the dark chamber assembly 602 may have profiles specifically fitted to allow the passage of particular sample holders or probe assemblies having an appropriate size, dimension, or reagent content, while blocking entrance or passage of other, non-authentic sample holders or probe assemblies.

The passage of the sample insertion tube 604 terminates in the dark chamber 606. The dark chamber provides a volume that is shield from external sources of light, and which has a reflective inner surface to reflect bioluminescence, increasing the number of photons detectable by a photon detector of the photon detection assembly 610.

A photon detection assembly 610 is disposed proximate and may, in some instances, form at least a portion of one of the walls or other surfaces that form or define the dark chamber 606. Within the dark chamber 606, photons emitted from a bioluminescent sample in the probe assembly may be reflected to increase the accuracy of measurement or detection. The level of biological contamination present in the sample is directly or indirectly indicated by the quantity or number of photons detected by the photon detector of the photon detection assembly 610. The photons striking the photon detector should therefore be attributable to only the bioluminescent sample. Stray photons not attributable to the bioluminescent sample, for example photons attributable to external or ambient lighting or heat, will adversely affect the performance of the photon detector assembly 610. Such stray photons may be reduced or even prevented from entering the dark chamber 606 by providing a lightproof dark chamber 606 and by using the sample holder or probe assembly and/or cover to optically seal the dark chamber 606.

While the dark chamber 606 can have any shape or form, certain shapes that enhance reflection toward the photon detector 610 are strongly preferred. Preferably, an interior of the dark chamber 606 will have a physical form capable of reflecting or otherwise directing at least a portion of the photons generated by the bioluminescent sample towards the photon detector assembly 610. Such reflection can be accomplished using one or more concave inner surfaces 608 either integrally formed or added to an interior space of the dark chamber 606. In at least some instances, the concave inner surface(s) 608 can be generally cylindrical, for example as shown in FIG. 6. It is particular advantageous where the inner surface(s) 608 within the dark chamber 606 are substantially spherical or hemispherical, other than where there are openings in the dark chamber 606. In some instances, the reflective inner surface(s) 608 may reflect only a portion of the electromagnetic spectrum, for example electromagnetic radiation between 500 nanometers (nm) and 600 nm.

Figure 13A:
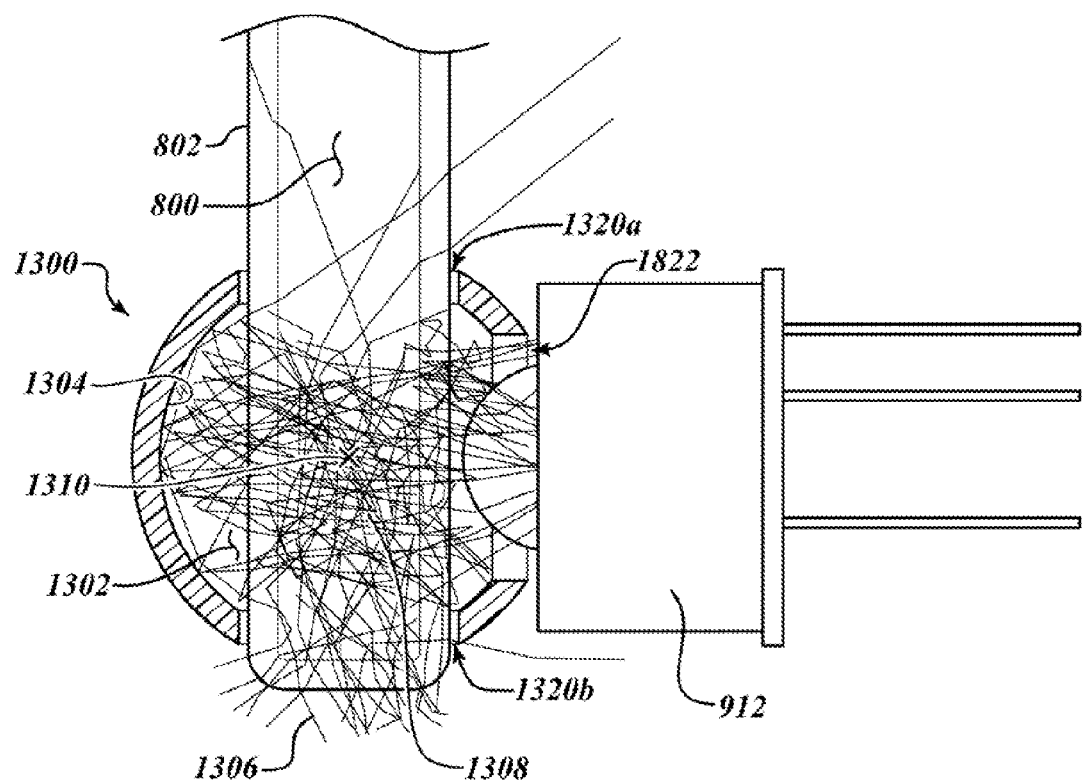
FIG. 13A is a side elevational view of an example probe assembly positioned within a spherical dark chamber and a multi-pixel photon counter, according to an illustrated embodiment described herein.
Figure 13B:
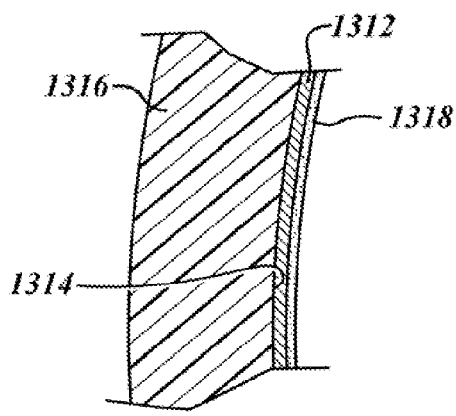
FIG. 13B is a partial sectional view of a portion of the spherical dark chamber, showing a molded plastic base, a reflective coating, layer or material on a concave spherical portion thereof, and an oxide coating, layer or material on the reflective coating, according to an illustrated embodiment described herein.

The dark chamber 606 may be formed as two distinct molded plastic pieces. As best illustrated in FIG. 13B, in some implementations, a reflective coating, layer or material 1312 may be disposed on at least a portion of a surface 1314 of the molded plastic pieces 1316 that will form the dark chamber 606. For example, a reflective metallic coating, layer or material 1312 may be applied to the interior or inner concave surfaces 1314 of the parts 1316 that will form the dark chamber 606. The reflective metallic coating, layer or material 1312 may include some form of the chemical element silver (Ag), or may include some other optically reflective metallic element. The reflective metallic coating, layer or material 1312 may be deposed onto the inner surface 1314, for instance via a thermal disposition or vapor disposition. Alternatively, the reflective coating, layer or material 1312 may be applied in some other manner. For instance, a reflective coating, layer or material 1312 may be applied to the concave surfaces 1314 of the molded plastic pieces 1316 via plating such as electroplating. Less preferably, a reflective coating, layer or material 1312 may be applied to the concave surfaces 1314 of the molded plastic pieces 1316 as a foil or leaf. The reflective metallic coating, layer or material 1312 may be polished after application, or may be applied in a manner that produces a high degree of reflection without the need for polishing. A protective layer, coating or material may be formed of deposited on or overlying the reflective coating, layer or material 1312. For example, a protective oxide dielectric coating 1318 may be formed, for example using techniques commonly employed to form passivation layers in silicon fabrication processes. The oxide 1318 may provide environmental protection to the underlying reflective coating, layer or material 1312. The oxide 1318 may additionally or alternatively serve as a filter, ensuring reflection of certain defined wavelengths or ranges of wavelengths, while reducing or eliminating the reflection of other wavelengths or ranges of wavelengths. Thus, wavelengths which are not of interest may be advantageously suppressed. The type of oxide, and the thickness of the oxide 1318, may be controlled to achieve the desired filtering.

Less preferable to a metallic layer, a highly reflective white coating may be employed, for example via a coating comprising a form of titanium dioxide. Also less preferable to a metallic layer, a barium compound layer may be employed, however such may be difficult to adhere securely to the concave surfaces of the molded plastic pieces.

The photon detection assembly 610 is physically and operably coupled to the interior of dark chamber 606 such that a photon detector is positioned to detect photons in or emanating from the dark chamber 606. A spherical reflective inner surface 608 of the dark chamber 606 advantageously reflects the photons, and focuses the photons on the photon detector. As explained in detail below, certain aspects of the sample holder or probe assembly, particularly in conjunction with the geometry of a spherical reflective inner surface 608 and overall positioning and orientation of the photon detection assembly with respect to the dark chamber 606, synergistically focuses the photons to achieve highly accurate detection or results.

In some cases, the photon detection assembly 610 may form at least a portion of the inner surface 608 of the dark chamber 606. In operation, photons emitted by the bioluminescent sample strike or fall incident upon one or more photon detectors (e.g., MPPC) of the photon detection assembly 610. The photons falling incident on the photon detector(s) create an electrical signal which can be filtered, amplified, and transmitted to the one or more processors 504. A characteristic (e.g., voltage, current, duty cycle) of the electrical signal provided by the photon detection assembly 610 is related to the number of photons emitted by the bioluminescent sample. The number of photons emitted by the bioluminescent sample is, in turn, proportionate to the amount of biological material present in the sample. The electrical signal generated by the photon detection assembly 610 therefore provides an indication of not only the presence but also the relative quantity of biological material present in the bioluminescent sample. In at least some instances, the photon detection assembly 610 may be particularly sensitive to heat which adversely compromises affects the accuracy, reliability, and reproducibility of the electrical signals provided by the photon detection assembly 610. In at least some instances, a heat dissipation assembly 612 may be thermally conductively coupled to the photon detection assembly 610 to remove heat away therefrom, and dissipate at least a portion of such heat for example via fins 612a or some other heat dissipation structure.

The heat dissipation assembly 612 can include one or more active or passive structures, devices, or systems that are thermally conductively coupled to the photon detection assembly 610. In some instances, the heat dissipation assembly 612 can include a single or multi-piece, active or passive, extended surface heat transfer device (e.g., an extended surface, finned heat transfer device) that is thermally coupled to the photon detection assembly 610 as shown in FIG. 6. In some instances, the heat dissipation assembly 612 can include one or more heat pipes or similar structures using a phase change heat transfer fluid to conduct heat generally away from the photon detection 610 for dissipation elsewhere within the housing 104, 204, 304, and 404 or from the housing 104, 204, 304, 404 into the ambient environment. In other instances, the heat dissipation assembly 612 may include an active cooler, for example a fan passing air across an extended surface heat sink thermally conductively coupled to the photon detection assembly 610, or a Peltier cooler thermally conductively coupled to the photon detection assembly 610.

Figure 7:
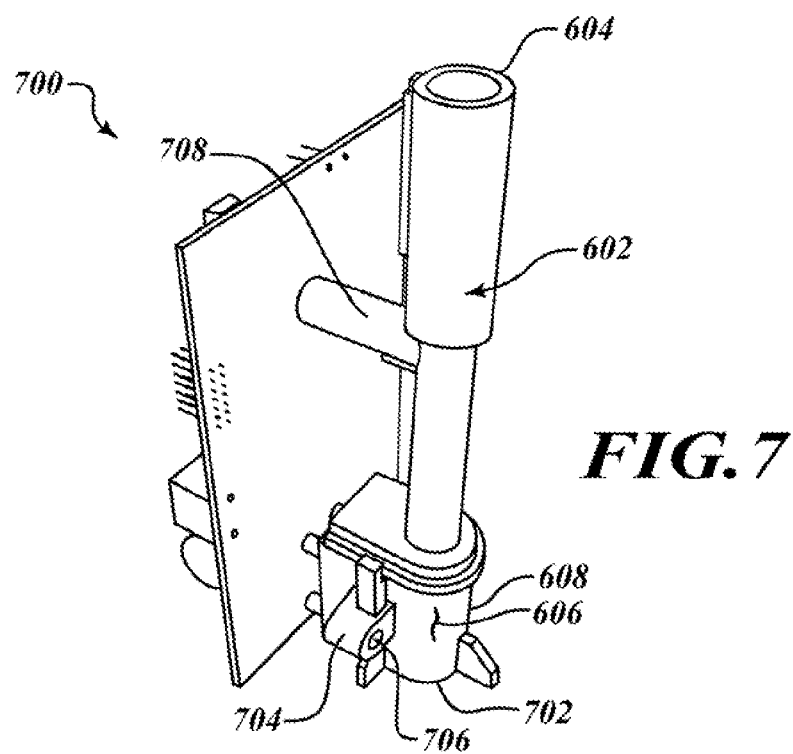
FIG. 7 is a perspective view of an example dark chamber assembly including a passage to receive a sample holder or probe assembly, and which terminates in a dark chamber that is physically and optically coupled to a photon detection assembly used for measuring and quantifying the photons emitted by the bioluminescence of a sample in the dark chamber, according to an illustrated embodiment described herein.

FIG. 7 shows a portion of an example sample collection and testing instrument 700, according to one illustrated embodiment. In particular, FIG. 7 shows the dark chamber assembly 602 including a sample insertion tube 604, and a photon detection assembly 610 both of which are physically and communicably coupled to the logic board 502. As shown in FIG. 7, in some instances the dark chamber 702 may be a multi-piece assembly that is physically coupled to the photon detection assembly 704 using one or more fasteners 706, for example one or more threaded fasteners such as the screws shown in FIG. 7. In other instances the dark chamber 702 may be attached to the photon detection assembly 704 via thermal bonding or via one or more chemical adhesives. One or sealing members or gaskets may be disposed between the dark chamber 702 and the photon detection assembly 704 to provide a light-tight joint that reduces the number of stray photons entering the interior of the dark chamber 702.

In at least some instances, the dark chamber assembly 602 can be physically coupled to the logic board 502, for example using structural supports 708 such as posts and one or more fasteners 706, for example one or more threaded fasteners such as the screws shown in FIG. 7. In other instances, the dark chamber 602 can be physically coupled to the logic board 502 using non-reversible connectors, for example a plurality of structural supports 708 that are thermally or adhesively bonded to the logic board 502 or riveted thereto, thereby rigidly affixing the dark chamber 602 to the logic board 502.

Figure 8A:
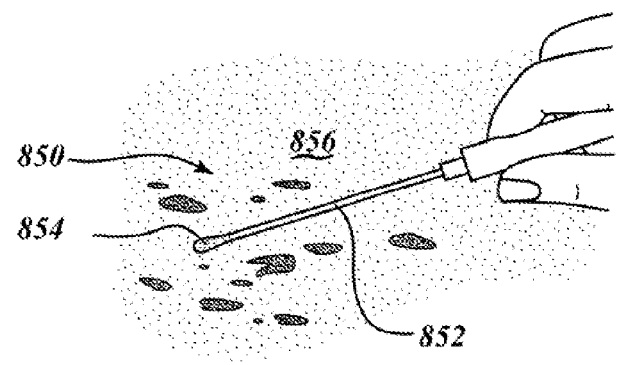
FIG. 8A is an isometric view of a swab being used to collect a sample or specimen from a surface via swiping of the surface with the swab, according to one illustrated embodiment.

FIG. 8A shows an example test swab 850 in use in collecting samples or specimens, according to one illustrated embodiment.

The test swab 850 includes at least a shaft member 852 having a swab tip 854 made of liquid permeable or absorbing material, such as cotton, Dacron, poly-foam or porous liquid permeable plastic sampling surfaces, disposed at one end. The swab tip 854 may be pre-moistened to aid in sample collection. In some instances, the swab tip 854 can be selected, sized, shaped, or configured to retain a known liquid sample volume, for example 0.1 milliliters (ml); 0.5 ml; 1.0 ml; 2.0 ml; 3.0 ml; or 5.0 ml. The liquid permeable material permits a reagent solution used with a probe assembly 800 (FIG. 8B), to flow through or along the shaft member 852 to the swab tip 854 and react with any biological matter present thereon. The reagent solution may leach biological matter from the swab tip 854.

The test swab 850 may be used to retrieve a sample or specimen from a surface or object of interest 856. For example, a user may swipe or otherwise contact a surface or object of interest 856 with a portion (e.g., swab tip 854) of the test swab 850. The surface or object of interest 856 may take any of a large variety of forms. For example, the surface or object of interest 856 may be a surface on which food preparation or manufacturing occurs or with which food is prepared or manufactured. The surface of interest 856 may be part of an object used during food preparation or manufacturing, for instance a bowl, baking sheets, pot, cauldron, pan, spoon, ladle, spatula, or mixer blades. The surface of interest 856 may be a piece of equipment or part of a piece of equipment used for food preparation or manufacturing, or for just about any other activity in which hygiene is important.

After collecting the sample or specimen, the test swab 850 in placed into the sample holder or probe assembly 800 (FIG. 8B), which in turn is inserted into the passage of the dark chamber assembly 602 of the instrument 100, 200, 300, 400.

Figure 8B:
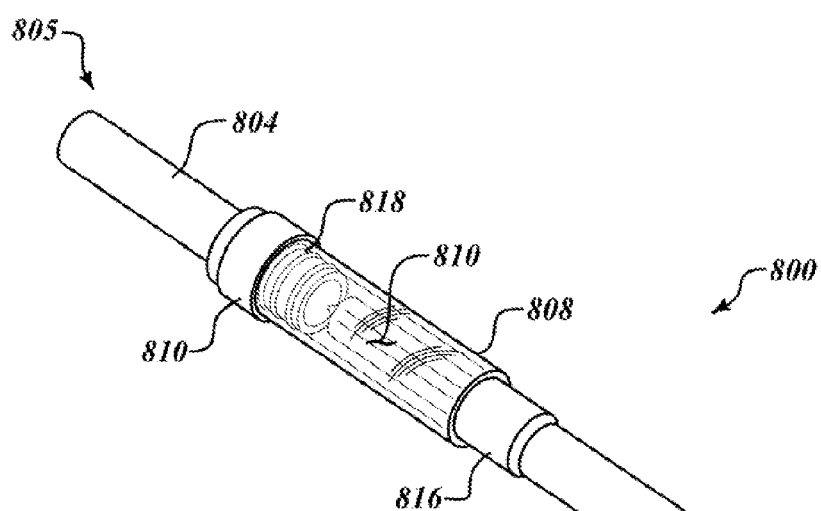
FIG. 8B is a sectional view of an example sample holder in the form of a probe assembly which forms part of a sample collection and analysis system along with the instrument, the sample holder or probe assembly having a conduit that is used to hold a test swab containing a sample for analysis an optically transparent chamber at a distal end portion which allows detection of photons emitted by a bioluminescent sample by the photon detection assembly, and one or more reagent chambers containing one or more reagents useful in causing one or more biological materials that may be present in the liquid sample to bioluminescence, according to an illustrated embodiment described herein.
Figure 8C:
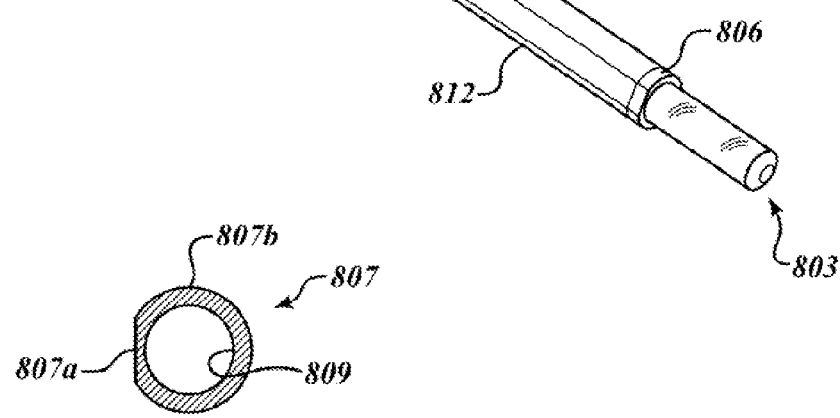
FIG. 8C is a cross-sectional diagram of a portion of the sample holder or probe assembly, illustrating a non-circular cross-sectional profile of an outer surface and a circular cross-sectional profile of an inner surface that forms a conduit in which a swab is receivable, according to one illustrated embodiment.
Figure 8D:
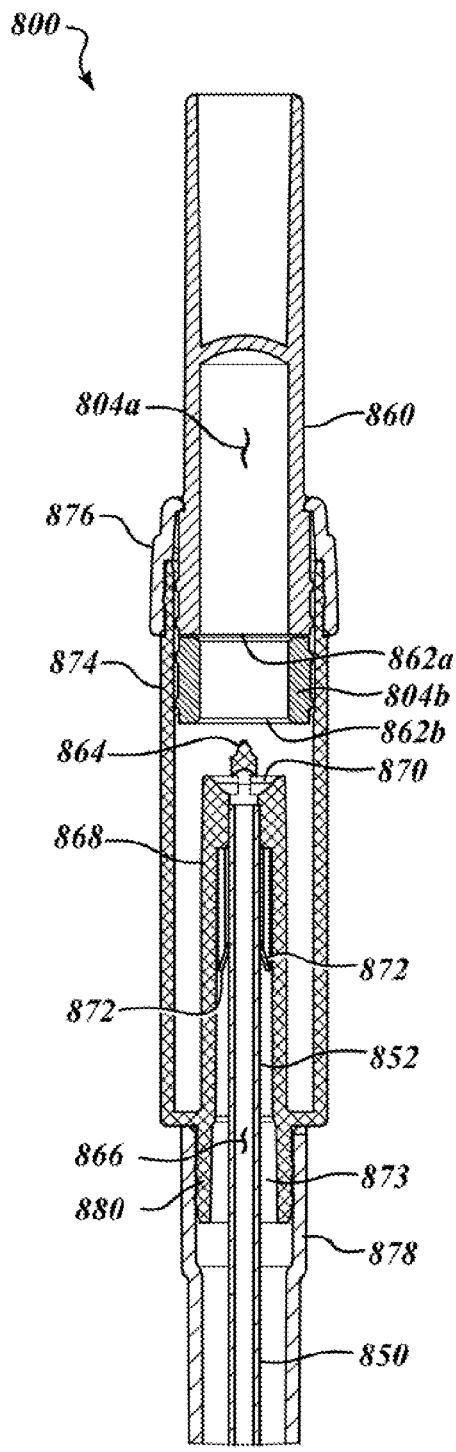
FIG. 8D is a cross-sectional diagram of a portion of the sample holder or probe assembly with a plunger thereof in a disengaged position or condition, prior to breaching any reservoirs or chambers, according to one illustrated embodiment.
Figure 8E:
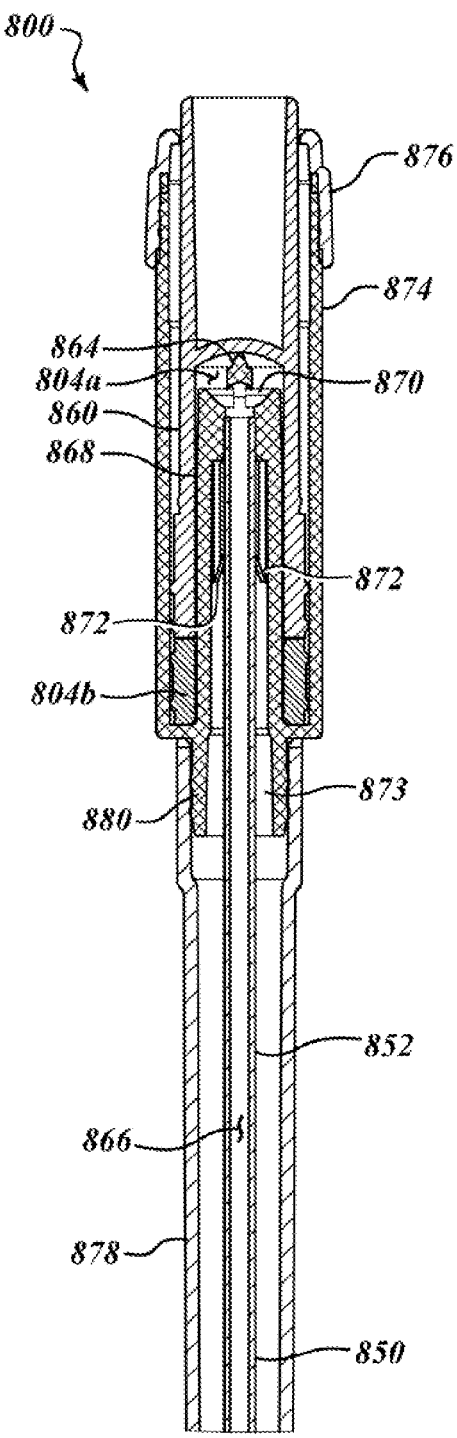
FIG. 8E is a cross-sectional diagram of a portion of the sample holder or probe assembly with a plunger thereof in an engaged position or condition, breaching reservoirs or chambers to release the contents thereof, according to one illustrated embodiment.

FIG. 8B shows an example test holder or probe assembly 800 that holds an example test swab 850 (FIG. 8B), according to one illustrated embodiment. FIG. 8D shows a portion of the sample holder or probe assembly 800 containing a test swab 850 and with a plunger 860 of the sample holder or probe 800 assembly in a disengaged position or condition, prior to breaching any reservoirs or chambers, according to one illustrated embodiment. FIG. 8E shows the portion of the sample holder or probe assembly 800 containing the test swab 850 and with the plunger 860 in an engaged position or condition, breaching reservoirs or chambers to release the contents thereof, according to one illustrated embodiment.

The test holder or probe assembly 800 synergistically combines and cooperates with the structure of the instrument 100, 200, 300, 400 to form a sample collection and testing system with high sensitivity and accuracy.

The probe assembly 800 is an elongated hollow member having an optically transparent chamber 802 (FIG. 8B) disposed at a distal end 803 of the probe assembly 800 and one or more reagent chambers 804a, 804b (collectively 804) disposed between the distal end 803 and a proximate end 805 of the probe assembly 800 which is spaced across a length of the probe assembly 800 from the distal end 803. A hollow first cylindrical member 806 and a hollow second cylindrical member 808 are interposed between the optically transparent chamber 802 and the reagent chamber(s) 804. A conduit or passage 810 extends through at least the first cylindrical member 806, the second cylindrical member 808, and terminates in the optically transparent chamber 802. The conduit or passage 810 fluidly couples the optically transparent chamber 802 to the reagent chamber(s) 804.

As best illustrated in FIGS. 8D and E, a first reagent chamber 804a may be a "wet" chamber storing a liquid solution, and a second reagent chamber 804b may be a "dry" chamber storing a solid or particulate or powder. Either the solution and/or the solid may be a reagent. Typically, the solid will may be the reagent, and the liquid solution is used to dissolve the solid reagent on contact therewith. Each of the reagent chambers 804a, 804b may be sealed by a respective frangible membrane 862a, 862b (illustrated in FIG. 8D, collectively 862), respectively. The plunger 860 may be advanced downward from the position illustrated in FIG. 8D to reach the position illustrated in FIG. 8E. In advancing to the position illustrated in FIG. 8E, a penetration structure 864 breaches (e.g., penetrates, ruptures) the frangible membranes 862, releasing the contents of the reagent chambers 804.

The liquid and solid may mix, activating the reagent. The resulting solution may enter a channel 866 in the shaft member 852 of the test swab 850 to the swab tip 854 (FIG. 8A). The shaft member 852 may be retained by a swab retaining portion 868 which may include a port 870 to provide fluid communication into the channel. The swab retaining portion 868 may include biasing members (e.g., leaf springs) 872 to resiliently engage the shaft member 852 when received in an aperture 873 of the swab retaining portion 868.

The plunger 860 may be selectively removably attachable to a main body portion 874 via a collar 876 or other coupler. The collar 876 may include a thread that threadly engages a complementary thread carried on the main body portion 874. One or more seals may be formed between the plunger 860 and the main body portion 874 to prevent leakage of solution and/or ingress of light. Seals may include various O-ring type seals (e.g., rubber, latex, polymer), or may be achieve by a close, interference fit between portions of the plunger 860 and an inner surface of the main body portion 874.

The main body portion 874 may be coupled to a tube portion 878. In particular, the main body portion 874 may have a reduced diameter or necked portion 880 that secures to the tube portion 878. The tube portion 878 may be secured to the reduced diameter or necked portion 880 via an interference fit, threads, or some other physical coupler.

In at least some instances, a portion of the shaft member 852 (e.g., portion spaced away from the swab tip 854) may contain an edge, point, or similar penetration structure useful in penetrating or rupturing a metal, foil, plastic, glass or similar membrane that seals the reagent chamber 804.

The test swab 850, including the shaft member 852 and the swab tip 854, can be sized to fit entirely within the conduit 810 extending through the first cylindrical member 806 and the second cylindrical member 808. In some implementations, the test swab 850 is received such that the swab tip 854 resides at least partially in the optically transparent chamber 802. In other implementations, the test swab 850 is received such that the swab tip 854 does not reside in the optically transparent chamber 802. Such implementations rely on reagent solution leaching sufficient amounts or material from the swab tip 854 and into the optically transparent chamber 802.

The optically transparent chamber 802 is a hollow chamber that is formed from a material having optically transparent properties at least at with respect to wavelengths of emitted bioluminescence be the sample and/or reagent. For example, optically transparent chamber 802 may be transparent (i.e., substantially pass) electromagnetic radiation having wavelengths of from about 370 nm to about 750 nm; from about 450 nm to about 650 nm; or from about 500 nm to about 600 nm. The optically transparent chamber 802 can, in some instances, be a thermoplastic material such as clear polycarbonate or the like. For example, the sample holder or probe assembly 800 may be formed via a two-shot injection molding process, one shot being for instance a clear polycarbonate and the other shot being for instance an opaque acrylonitrile butadiene styrene (ABS) plastic. In other instances the optically transparent chamber 802 can be a glass, for example borosilicate glass or the like. The interior of at least the optically transparent chamber 802 is preferably sterile, containing no biological material which would adversely impact the accuracy of test results.

After mixing with one or more reagents (e.g., luciferase), one or more biological compounds, including but not limited to adenosine triphosphate (ATP) will bioluminescence and emit photons. The photons emitted by the bioluminescence will either fall incident upon the photon detector of the photon detector assembly 610 or will be reflected by within the dark chamber 606 and eventually striking the photon detector of the photon detector assembly 610. In this manner the photons striking the photon detector of the photon detection assembly 610 provide an indication of the presence and relative quantity of biological matter present on the swab tip 854, without significant loss in the dark chamber and without significant interference from stray photons or thermal noise.

The reagent chamber(s) 804 contains one or more reagents which when mixed with the sample on the swab tip 854, reacts and causes at least a portion of the biological material present in the test swab to bioluminescence. In some instances, the reagent chamber 804 may contain more than one reagent, or different reagents may be contained in separate reagent chambers(s). For example, the reagent chamber 804 may contain a solid reagent and a liquid reagent which combine when an enclosure containing the reagents in the reagent chamber 804 is ruptured by the pointed tip of the shaft member 852. In some instances, the bioluminescence may be caused by the reaction of adenosine triphosphate with one or more enzymes such as luciferase, according to the following reaction:

$$ATP+D\text{-}Luciferin+O_2 \rightarrow Oxyluciferin+AMP+PPi+CO_2+Light\ (560\ nm)$$

The reagents within the reagent chamber 804 flow through or around the test swab and into the swab tip 854. The swab tip 854 may be positioned in the optically transparent chamber 802 with the reagent solution. Alternatively, the reagent solution with leached sample or specimen collects in the optically transparent chamber 802. In at least some implementations, the reagents may be sealed or retained in the reagent chamber 804 using a glass or plastic ampoule or the like. In other implementations the reagents may be sealed or retained in the reagent chamber 804 using a foil or plastic sealed container that is punctured or otherwise ruptured by the shaft member 852. In some implementations, a portion of the test swab 850 itself may contain all or a portion of one or more reagents. At times, the reagent chamber 804 can be physically attached to the shaft member 852. In some implementations, the shaft member 852 is driven into the reagent chamber 804 when the chamber is attached to the probe assembly 800 by the user.

In one implementation, the reagent chamber 804 is attached to the shaft member 852 of the test swab 850. After collecting a sample on the swab tip 854, the test swab is inserted into the conduit 810 in the probe assembly 800. Male threads 818 on an exterior portion of the reagent chamber 804 engage female threads on the interior surface of the second cylindrical member 808. As the reagent chamber 804 is driven into the second cylindrical member 808 using the threads 818, the shaft member 852 penetrates an ampoule containing the reagents, releasing the reagents into the conduit 810.

In another implementation, the test swab 850 is separate from the reagent chamber 804. After collecting a sample on the swab tip 854, the test swab is inserted into conduit 810 in the probe assembly 800. One or more flexible rings are disposed about the perimeter of the reagent chamber 804. The one or more flexible rings provide a liquid tight seal between the reagent chamber 804 and the interior surface of the second cylindrical member 808. As the user press fits the reagent chamber 804 into the second cylindrical member 808, the shaft member 852 penetrates an ampoule containing the reagents, releasing the reagents into the conduit 810.

The first cylindrical member 806 is bonded, threaded, joined, or otherwise physically and fluidly attached to the optically transparent chamber 802. The conduit 810 extends the length of the first cylindrical member 806, providing a central fluid passage therethrough. The size, shape, and configuration of the conduit 810 accommodate the passage of the test swab 850, including the shaft member 852 and the swab tip 854. In some implementations, the first cylindrical member 806 can be an opaque material such as one or more thermoplastics (e.g., ABS plastic), to minimize the transmission of photons via the probe assembly 800 into the dark chamber 606. Although not shown in FIG. 8A, in some instances one or more unique or identifying marks can be disposed on the exterior surface of the first cylindrical member 806, for example one or more printed, embossed or debossed logos, one or more printed, embossed or debossed trademarked logos, or one or more printed, embossed or debossed machine readable bar codes, matrix codes, or the like.

The first cylindrical member 806 may have a uniform or a non-uniform cross sectional profile or perimeter. In one example as illustrated in FIG. 8C, a first portion 812 of the first cylindrical member 806 can have a D-shaped perimeter or outer surface cross-sectional profile 807, having a flat portion 807a and an arcuate portion 807b. While the first portion 812 may have a non-circular cross-sectional profile 807, the first portion 812 may also have an inner surface circular cross-sectional profile 809, as illustrated in FIG. 8C. The inner surface circular cross-sectional profile 809 forms part of the conduit, is sized and dimensioned to receive a swab therein. The first portion 812 may, for example, transition to a second portion 814 having a substantially similar diameter circular perimeter or cross-sectional profile. The second portion 814 may, for example, transition to a third portion 816, having a larger diameter circular perimeter or cross-sectional profile than the second portion 814, for instance as illustrated in FIG. 8B.

The first cylindrical member 806 may be physically coupled to or integrally formed with the second cylindrical member 808.

The second cylindrical member 808 is interposed between the first cylindrical member 806 and the reagent chamber 804. One or more fastening devices 818, for example threads, flexible friction collars, or similar devices, may be disposed on the reagent chamber 804, the interior surface of the second cylindrical member 808, or any combination thereof. In some instances, the fastening devices 818 can include one or more threads to threadedly couple the reagent chamber 804 to the second cylindrical member 808. In other instances, the fastening devices 818 can include one or more flexible friction collars to frictionally couple the reagent chamber 804 to the second cylindrical member 808.

The second cylindrical member 808 may be a transparent or translucent material that advantageously permits visual observation of the flow of reagents within the conduit 810. The second cylindrical member 808 can have the same or a different diameter or cross section than the first cylindrical member 806. For example, the second cylindrical member 808 can have a larger diameter than the third portion 816 of the first cylindrical member 806 as shown in FIG. 8.

Figure 9:
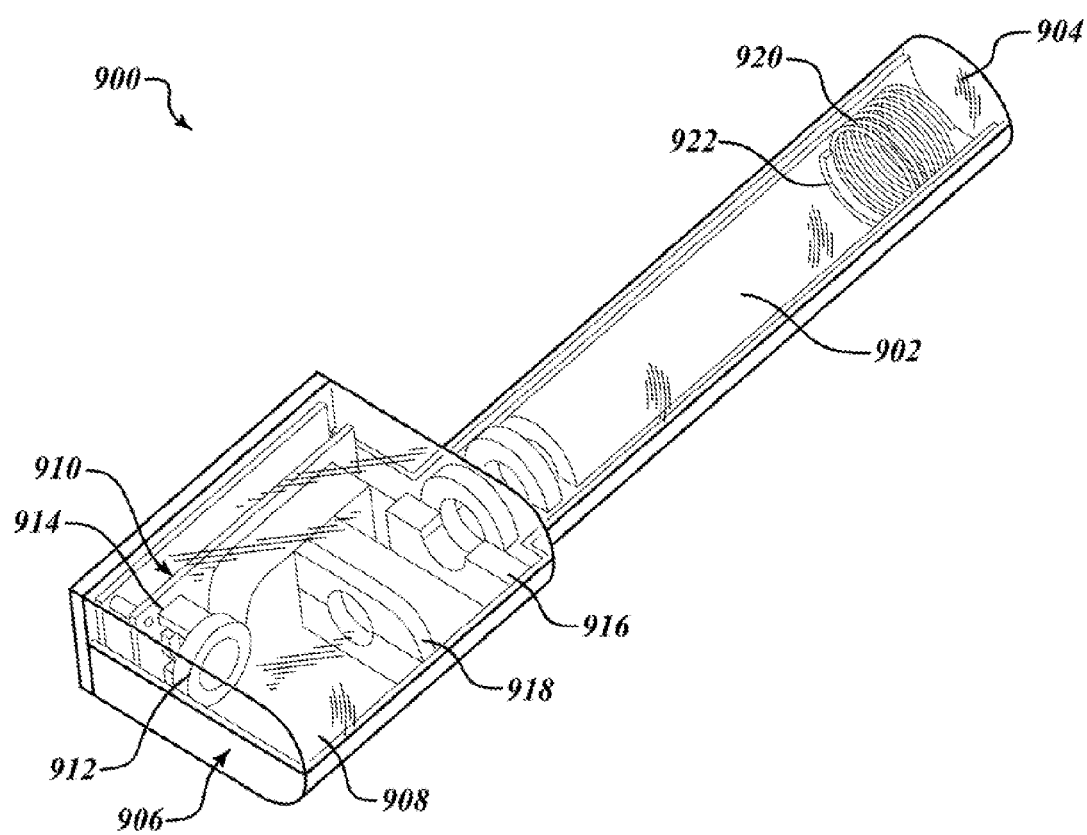
FIG. 9 is a partially sectioned perspective view of an example dark chamber assembly and photon detection assembly, the dark chamber assembly including an intermediate tube, a spring, and a dark chamber, according to an illustrated embodiment described herein.

FIG. 9 shows an example dark chamber assembly 900, according to one illustrated embodiment. The dark chamber assembly 900 includes a generally cylindrical intermediate section 902 having an aperture 904 at a first end that is sized, shaped, and configured to accommodate the insertion of a probe assembly 800. A substantially rectangular dark chamber 906 is disposed at the distal end of the intermediate section 902.

At least a portion of the dark chamber 906 can be radiused to form a curved or spherical surface defining a concave surface 908 within the dark chamber 906. The curved or spherical surface will have a center point 1310 (FIG. 13A). The substantially rectangular dark chamber 906 can have a larger cross-sectional area than the generally circular intermediate section 902.

In at least some instances, the concave or spherical surface 908 is positioned at least partially in opposition to a photon detection assembly 910. One or more reflective surfaces or coatings may be disposed on at least a portion of the concave surface 908 such that photons striking the curved surface 908 are reflected towards the photon detection assembly 910. The reflection of photons emitted by a bioluminescent material placed in the dark chamber 906 towards the photon detection assembly 910 can increase the overall accuracy or responsiveness of the photon detection assembly 910.

The photon detection assembly 910 includes at least one photodiode that is communicatively coupled to a transmitter 914. Preferably, the photon detection assembly 910 includes an array of avalanche diodes, in the form of a multi-pixel photon counter sensor 912. Photons emitted by bioluminescent material placed in the optically transparent chamber 802 enter the dark chamber 906 and fall incident upon the photodiode(s) 912. Photons incident upon the photodiode(s) 912 provide an indication that biological matter (e.g., adenosine triphosphate) is present in the optically transparent chamber 802. The number and intensity of the photons incident upon the photodiode(s) 912 provide an indication of the relative quantity of biological matter present in the optically transparent chamber 802.

Although the photodiode(s) 912 provides a signal output related to the number and intensity of incident photons, the signal is of sufficiently low level and quality to preclude direct transmission to the logic board 502. In some instances, the signal provided by the photon detection assembly 910 is introduced to a communicably coupled transmitter 914. The transmitter 914 can filter or amplify the electrical signal received from the photon detection assembly 910 to provide a signal output having sufficient strength and quality for communication to the logic board 502. In at least some instances, the signal output from the transmitter 914 can be provided to the at least one processor 504 on the logic board 502.

Obtaining an accurate, reliable, consistent, and reproducible signal from the photon detection assembly 910 is dependent upon multiple factors. Consistent and proper positioning of each bioluminescent sample within the dark chamber 906 can reduce variability attributable to the alignment or lack of alignment between the bioluminescent sample, the photon detection assembly 910, and the curved or spherical surface 908. This is particular so where the transparent portion of the probe assembly 800 and liquid retained therein form or serve as an optical lens, for instance a cylindrical lens. The transparent portion 802 of the probe assembly 800 may advantageously be spaced from the photon detector 912 of the photon detection assembly 910 by a distance that at least approximately matches a focal length of the optical lens formed by the transparent portion 802 of the probe assembly 800 and liquid retained therein. Such may enhance detection of emitted photons. Reducing or eliminating stray or incident photons from entering the dark chamber 906 can reduce the noise in and improve the consistency of the signal provided by the photon detection assembly 910.

To assist in properly positioning the optically clear chamber 802 within the dark chamber 906 and to reduce the entry of stray photons into the dark chamber, one or more intermediate stays 916 may be positioned within the intermediate section 902 of the dark chamber assembly 900. The intermediate stays 916 maintain proper lateral placement of the probe assembly 800 within the dark chamber assembly 900 by coaxially aligning the probe assembly 800 and the dark chamber assembly 900. The intermediate stays 916 may, in some instances, position the optically clear or substantially transparent chamber 802 containing the bioluminescent sample at or near the focal point of the concave or spherical surface 908.

In some instances, an aperture through which the probe assembly 800 is passed may penetrate some or all of the intermediate stays 916 within the intermediate section 902. In some instances, the intermediate stays 916 may share a common aperture size, shape, configuration, or position. In other instances, all or a portion of the intermediate stays 916 may have a different aperture size, shape, configuration, or position. The size, shape, configuration, or position of the aperture in each of the intermediate stays 916 may depend in whole or in part on the size, shape, configuration, or position of the exterior perimeter of the probe assembly 800 at the point where the probe assembly 800 passes through the aperture. The intermediate stays 916 may be evenly or unevenly distributed within the intermediate section 902. In at least one instance shown in FIG. 9, two intermediate stays 916 may be positioned within the intermediate section 902 in locations that are closer to the dark chamber 906 than the aperture 904.

In at least some instances, the apertures in each of the intermediate stays 916 limit the orientation or position of the probe assembly 800 within the dark chamber assembly 900. For example, the apertures in each of the intermediate stays 916 may be D-shaped and the exterior or outer surface of the first portion 812 of the first cylindrical portion of the 806 probe assembly 800 may have a complimentary D-shape cross-sectional profile. In such a situation, the probe assembly 800 can only be inserted into the dark chamber assembly 900 when the D-shaped portions of the probe assembly 800 and the aperture align. In addition to positioning the probe assembly 800 within the dark chamber assembly 900, maintaining a close tolerance between the intermediate stays 916 and the external perimeter of the probe assembly 800 advantageously reduces the intrusion of stray photons into the dark chamber 906. While the exterior or outer surface of the first portion 812 of the first cylindrical portion of the 806 probe assembly 800 may have the complimentary D-shaped cross-sectional profile, an inner surface may have a circular cross-sectional profile.

In at least some instances one or more dark chamber stays 918 may be disposed within the dark chamber 906. The dark chamber stays 918 locate the optically transparent chamber 802 of the probe assembly 800 laterally within the dark chamber 906. In at least some instances, the dark chamber stays 918 can position the optically transparent chamber 802 within the dark chamber 906 at or near the focal point of the curved or spherical surface 908. In addition to laterally positioning the probe assembly 800, maintaining a close tolerance between the aperture in the dark chamber stays 918 and the external perimeter of the probe assembly 800 may advantageously further reduce or limit the intrusion of stray photons into the dark chamber 806.

A spring 920 or similar tension member may be disposed within the intermediate portion 902 of the dark chamber assembly 900. The spring 920 can be retained at a desired position within the intermediate portion 902 using, for example, a collar 922 disposed at least partially about the interior surface of the intermediate portion 902. The spring 920 is useful in positioning the probe assembly 800 along the axial centerline of the dark chamber assembly 900. Such axial positioning can accurately and consistently position the optically transparent chamber 802 at a desired axial location within the dark chamber 906. Such positioning permits substantially uniform photon measurement conditions on a sample-by-sample basis by reducing any variability associated with positioning the optically transparent chamber 802 within the dark chamber 906. For example, compressing the spring 920 against the collar 922 using the probe assembly 800 can axially position the probe assembly proximate the photodiode 912 in the dark chamber 906.

In some instances, the larger diameter third portion 816 of the first cylindrical member 806 can physically engage the spring 920 inside the intermediate portion 902 of the dark chamber assembly 900. For example, the larger diameter portion 816 of the first cylindrical member 816 can rest upon the top of the spring 920. In some instances, the increased diameter of the second cylindrical member 808 can physically engage the spring 920 inside the intermediate portion 902 of the dark chamber assembly 900. For example, the second cylindrical member 808 can rest upon the top of the spring 920.

Figure 10:
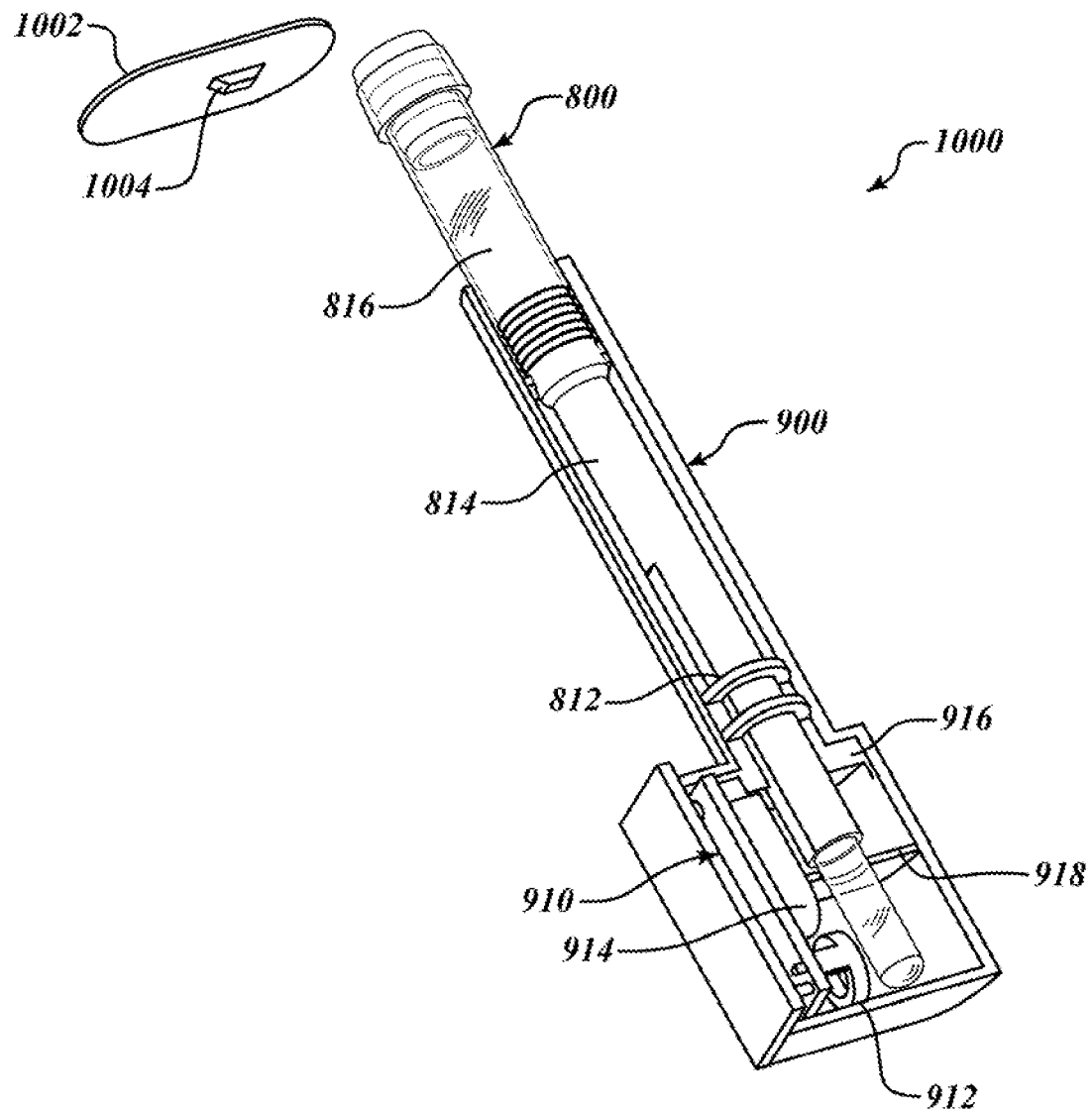
FIG. 10 is a sectional perspective view of a photon detection assembly, an example dark chamber assembly, a sample holder or probe assembly, and a cover of a cover assembly, the sample holder or probe assembly at least partially inserted in a passage of the dark chamber assembly; the cover which in use closes an opening or entrance of the passage of the dark chamber assembly and applies a force sufficient to compress a spring to properly position the sample holder or probe assembly with a transparent distal portion thereof located in the dark chamber, according to an illustrated embodiment described herein.

FIG. 10 shows a system 1000 showing an example probe assembly 800 inserted in an example dark chamber assembly 900 of an instrument. Visible in system 1000 is the relationship between the dark chamber 906, the optically transparent chamber 802 and the photodiode(s) (e.g., MPPC) 912. Specifically, as shown in FIG. 10, photons emitted by the bioluminescent sample and exiting the optically transparent chamber 802 either directly impinge upon the photodiode(s) 912 or are reflected from the concave surface 908 of the dark chamber 906 and are reflected back towards the photodiode(s) 912. As previously noted, the transparent portion of the probe assembly 800 and liquid contained therein may serve or function as a lens, focusing the bioluminescence toward the photodiode(s) 912 and realizing an advantageous synergistic effect. This may be true whether the bioluminescence travels directly toward the photodiodes(s) 912 without reflection or reflects from the reflective inner surface of the dark chamber 906. The transmitter 914 in the photon detection assembly 910 generates and transmits a signal that is related to the quantity or intensity of the photons striking the photodiode(s) 912.

In operation, the optically transparent chamber 802 can be disposed proximate the photodiode(s) 912 partially or completely within the dark chamber 906. Placement of the optically transparent chamber 802 within the dark chamber 906 and proximate the photodiode(s) 912 permits the accurate and reliable collection of photons emitted by the bioluminescent sample contained within the optically transparent chamber 802. The concave surface 908 can assist in the collection of photons emitted by the bioluminescent sample within the optically transparent chamber 802 by reflecting a portion of the emitted photons back towards the photodiode(s) 912. The provision of a reflective surface on at least a portion of the concave surface 908 can further enhance the efficiency, accuracy, and reliability of the photodiode(s) 912 in collecting the photons emitted by the bioluminescent sample in the optically transparent chamber 802, as can the focusing achieved by the optically transparent chamber 802 and liquid contained therein.

Providing accurate, reliable, and reproducible results is dependent at least in part on proper lateral placement of the bioluminescent sample contained in the optically clear portion 802 of the probe assembly 800 within the dark chamber 906. One or more features, for example the one or more intermediate stays 916 may be positioned within the dark chamber assembly 900 to effect proper lateral placement of the probe assembly 800 and to limit the entry of external stray photons into the dark chamber 906. In some instances, one or more dark chamber stays or braces 918 may also be disposed within the dark chamber 906. Such dark chamber stays or braces 918 may position the optically transparent chamber 802 within the dark chamber 906. For example, one or more dark chamber stays or braces 918 may position the optically transparent chamber 802 at the focal point of the curved surface 908.

Upon insertion into the dark chamber assembly 900, the probe assembly 800 compresses the spring 920. The spring 920 can assist in maintaining the optically transparent chamber 802 in a proper axial alignment with the photodiode 912 in the dark chamber 906. In at least some instances, the first cylindrical section 806 can compress the spring 920. In other instances, the second cylindrical section 808 can compress the spring 920.

A cover assembly 1002 can be pivotably, slideably, threadedly or similarly displaceably attached to the system 100, 200, 300, 400. In at least some instances, the cover assembly 1002 can be operably coupled to the housing top 122, 222, 322, 422. The cover assembly 1002 can have one or more latches or similar mechanical or electromechanical devices to maintain the cover assembly 1002 in one or more desired positions, for example an open position exposing at least a portion of the dark chamber assembly 900, or a closed position covering at least a portion of the dark chamber assembly 900.

The cover assembly 1002 may, in some instances, be used either alone or in conjunction with one or more other systems or devices to secure the probe assembly 800 within the dark chamber assembly 900. When in the closed position, the cover assembly 1002 may advantageously assist in limiting the entry of stray photons of light from the ambient environment to the dark chamber assembly 900. In some instances, the cover assembly 1002 can include a hinged door that rotates about one or more hinges after the probe assembly 800 is placed into the dark chamber assembly 900. In other instances, the cover assembly 1002 can include a slideable door that is displaceably positionable along one or more channels after the probe assembly 800 is placed into the dark chamber assembly 900.

The cover assembly 1002 can maintain the spring 920 in compression while the probe assembly 800 is disposed within the dark chamber assembly 900. In some instances, the cover assembly 1002 can have one or more projections 1004. The one or more projections 1004 can be useful, for example, in exerting additional pressure on the probe assembly 800, thereby assisting in proper positioning of the probe assembly 800 in the dark chamber assembly 900. In other instances the one or more projections 1004 can displace the reagent chamber 804 onto the test swab 850, rupturing one or more reagent ampoules located in or frangible membranes located across the reagent chamber 804. In some instances, the compression of the spring 920 can provide an indication to the system 100, 200, 300, 400 that a probe assembly 800 has been inserted and the photon detection assembly 910 should be energized. In other instances, placing the cover assembly 1002 in a closed position can provide an indication to the system 100, 200, 300, 400 that a probe assembly 800 has been inserted into the dark chamber assembly 900.

In at least some instances, opening the cover assembly 1002 can assist in the removal of the probe assembly 800 from the dark chamber assembly 900 by releasing the compressive force on the spring 920. Upon release of compression the spring 920 can return to an uncompressed position, providing an upward force on the probe assembly 800 that tends to "lift" the probe assembly from the dark chamber assembly 900.

Figure 11:
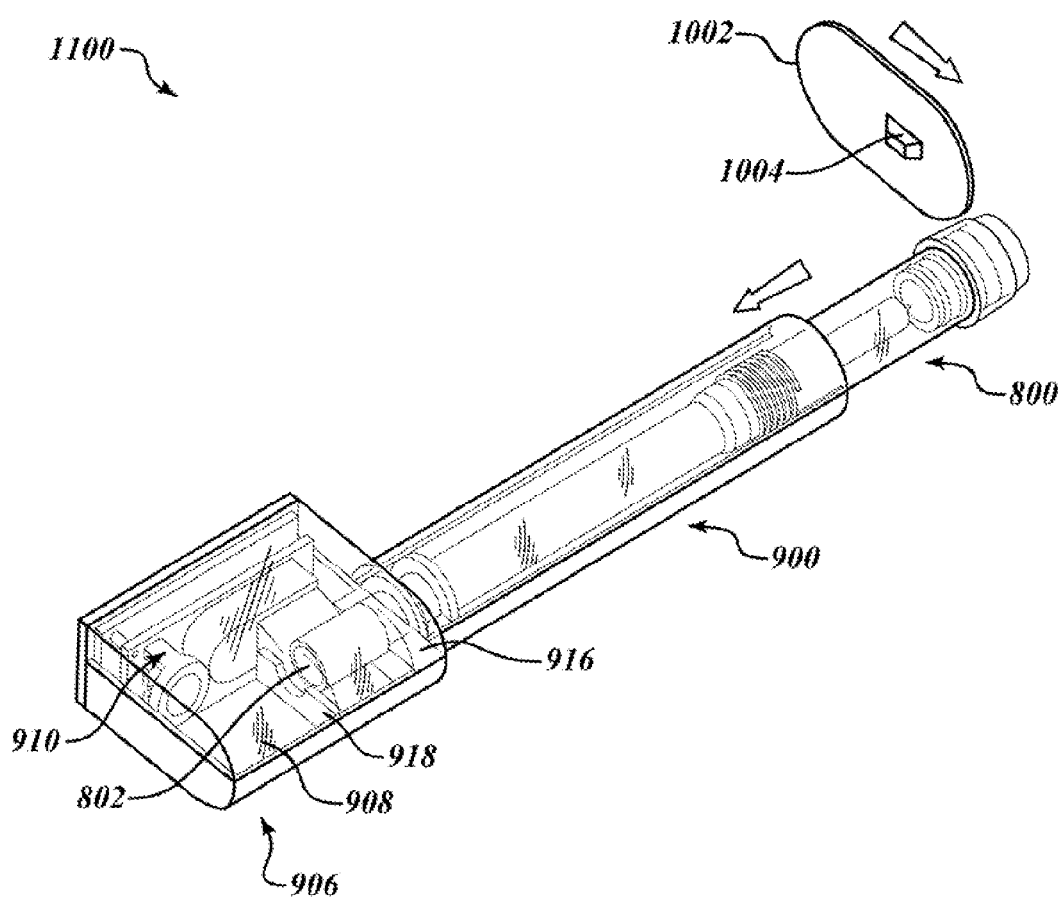
FIG. 11 is another sectional perspective view of the photon detection assembly, the example dark chamber assembly, the specimen holder or probe assembly, and cover of FIG. 10, which better illustrates one or more intermediate and dark chamber stays that position the sample holder or probe assembly laterally and axially within the passage of the dark chamber assembly, according to an illustrated embodiment described herein.

FIG. 11 shows a portion of a system 1000 including an example probe assembly 800 inserted into an example dark chamber assembly 900. The intermediate stays 916 within the dark chamber assembly 900 maintain the probe assembly 800 in a more or less coaxially centered position within the intermediate section 902 and in the dark chamber 906. The optically transparent chamber 802 is maintained substantially at the focus of the concave or spherical surface 908 by the dark chamber stays 918. The compression of the spring 920 against the collar 922 inside of the intermediate section 902 longitudinally positions the optically transparent chamber 802 within the dark chamber 906. Spring 920 is maintained in compression by the cover assembly 1002 and the projection 1004, both of which prevent the upward displacement of the probe assembly 800 within the dark chamber assembly 900.

Proper positioning of the probe assembly 800 within the dark chamber assembly 900 advantageously permits substantially all of the photons emitted by the bioluminescence of the biological sample in the optically transparent chamber 802 to fall incident upon the photon detection assembly 910, and ensure the advantageously synergistic effect of the optically transparent chamber 802 and liquid contained therein. In such a manner, the photon detection assembly 910 is able to provide an accurate, reliable and reproducible signal that is related to the number and intensity of the incident photons. The relatively tight fit between the intermediate stays 918 and the first cylindrical member 906 and the dark chamber stays 818 and the optically transparent chamber 902 reduce the likelihood of external photons entering the dark chamber and affecting the accuracy of the photon detection assembly 810.

In at least some instances, one or more identifiers may be disposed in whole or in part on the first cylindrical member 806. These identifiers may variously include one or more embossed, debossed or printed designs, embossed, debossed or printed trademarks, embossed, debossed or printed trade names, embossed, debossed or printed bar machine-readable symbols (e.g., one-dimensional or barcode symbols, two-dimensional or matrix or area code symbols), or combinations thereof. Although not shown in FIG. 11, in at least some instances, a reader (e.g., a photodiode array) or similar device may be disposed proximate the probe assembly 800 to "read" or otherwise convert one or more identifiers on the probe assembly 800 to one or more electronic signals. Such electronic signals can be compared to reference signals stored within the non-transitory storage medium 506 and are useful, for example, in detecting the type of probe assembly 800 used, detecting the type and quantity of reagent in the reagent chamber 804, detecting the compatibility of the probe assembly 800 with the photon detection assembly 910, detecting whether the probe assembly 800 complies with manufacturer or distributor requirements, detecting whether the probe assembly 800 is genuine, and the like. Such may be critical to ensuring that the probe assembly 800 correctly aligns with the optics (e.g., reflective spherical inner surface, lenses, filters) and/or photodiode(s) 912.

Figure 12:
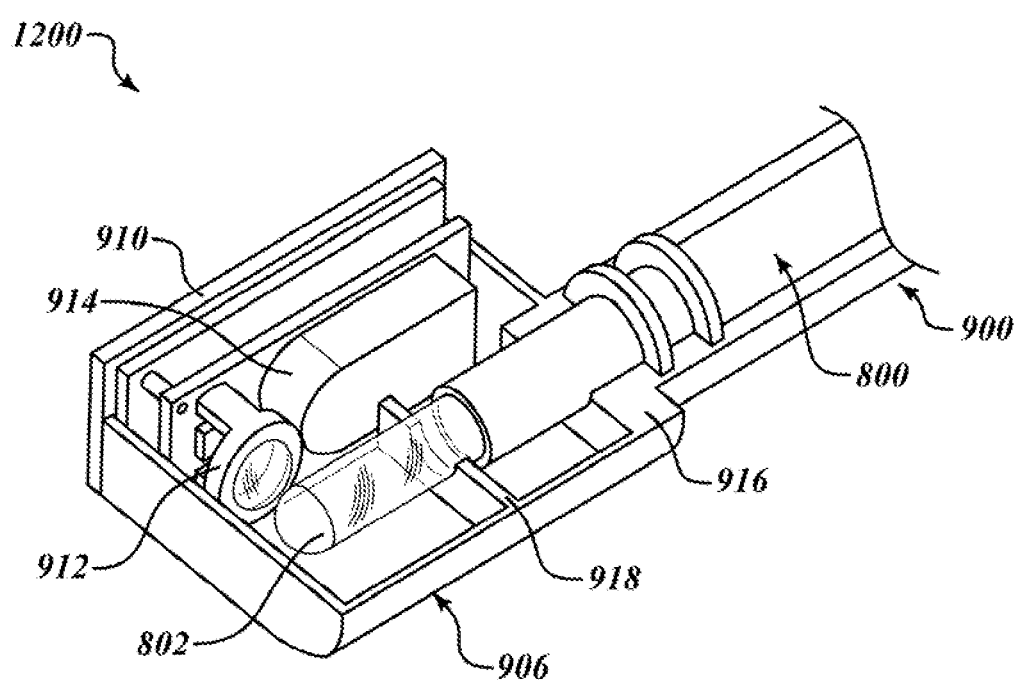
FIG. 12 is an enlarged perspective view of the photon detection assembly, lower portion of the example dark chamber assembly, and lower portion of the specimen holder or probe assembly of FIGS. 10 and 11, better illustrating an optically transparent portion of the sample holder or probe assembly positioned proximate the photon detection assembly, as well as a spatial relationship between the dark chamber assembly, the distal end of the sample holder or probe assembly and the photon detection assembly, according to an illustrated embodiment described herein.

FIG. 12 shows the probe assembly 800 positioned within the dark chamber 906. The physical relationship and proximity between the optically transparent chamber 802, the photodiode(s) 912 and the dark chamber 906 is apparent in FIG. 12. The swab tip 854 contains the biological sample and may in some instances be positioned within the optically transparent chamber 802. Reagent from the reagent chamber 804 at the opposite end of the test swab assembly 800 flows along the shaft member 852 and mixes with the biological sample on the swab tip 854. The reagent causes one or more compounds present in the biological sample to bioluminesce. As a consequence of the bioluminescence of the sample, photons of light are emitted from the optically transparent portion 802. The emitted photons fall incident upon the photodiode(s) (e.g., MPPC) 912, causing the photodiode(s) 912 to transmit a signal proportionate to the number and intensity of the incident photons to the transmitter 914. In turn, the transmitter 914 filters and amplifies the signal to generate and transmit a signal proportionate to the quantity or intensity of photons incident upon the photodiode(s) 912 to one or more external devices such as the at least one processor 504.

FIG. 13A shows a spherical dark chamber 1300 having a hemispherical curved reflective inner surface 1304 that forms an interior 1302. Photons 1306 generated by the bioluminescent sample 1308 in the optically transparent chamber 802 are shown as scattered lines exiting the optically transparent chamber 802 and reflecting off the reflective inner surface 1304 of the wall(s) of the spherical dark chamber 1300.

The spherical dark chamber 1300 includes one or more sample holder or probe assembly receiver openings 1320a, 1320b (collectively 1320) sized to receive an optically transparent chamber portion 802 of a sample holder or probe assembly 800. As illustrated, the spherical dark chamber 1300 includes two such receiver openings 1320a, 1320b, opposed to one another diametrically opposed to one another across a diameter or centerpoint 1310 of the reflective inner surface 1304 of the spherical dark chamber 1300. In other implementations, the spherical dark chamber 1300 may include a single receiver opening 1320a, to position a distal tip 803 of the optically transparent chamber portion 802 of the sample holder or probe assembly 800 within the cavity or interior 1302 during use.

Notably, the receiver openings 1820a, 1820b or opening 1820a are or is arranged to position the optically transparent portion 802 to pass through the centerpoint 1310 of the reflective inner surface 1304 of the spherical dark chamber 1300 to direct and/or focus illumination toward a detector opening 1822 and associated photodiode(s) 912. Such may not only direct illumination at or on the photodiode(s) 912, but may advantageously employ the as well as fluid contained therein as a cylindrical lens to focus illumination at or on the photodiode(s) 912. As illustrated in FIG. 13A, a portion of the photodiodes 912 or associated detector assembly may protrude into the interior 1302 of the spherical dark chamber 1300 via the detector opening 1822. In other implementations, the photodiodes 912 or associated detector assembly may be completely located externally from the interior 1302, the detector opening 1822 allowing transmission of illumination through to the opening 1822 photodiodes 912 or associated detector assembly. Such may pass through a window or lens at the detector opening 1822.

Photodiode(s) (e.g., MPPC) 912 is shown positioned proximate the spherical dark chamber 1302. Photons exiting the interior 1302 of the dark chamber 1300 strike the photodiode(s) 912. Although various example dark chambers (e.g., cylindrical, spherical) have been described above, a dark chamber having any geometry with the ability to reflect at least a portion of the photons 1306 emitted by a bioluminescent sample 1308 to the photodiode 912 may be substituted. For example, one or more parabolic surfaces, one or more faceted surfaces, or one or more segmented surfaces may be used to form all or a portion of the dark chamber 1302. Spherical inner surfaces are particularly desirable.

The various embodiments described above combine the ability to accurately, precisely, and efficiently measure the bioluminescence of a sample collected from a surface in a facility subject to HACCP requirements. The bioluminescence of the sample is measured using the photon detection assembly 910, and data associated with the sample (e.g., date, time, location, test results, etc.) are stored within the non-transitory storage media 506 for later communication to one or more external devices or networks. The advantages of such a system are apparent, particularly within the food industry where HACCP-based standards are prevalent and the use of bioluminescence as a means for assessing biological contamination of surfaces is accepted and very relevant. In order to comply with HACCP guidelines, a food processor or food manufacturer must be able to identify the critical control points ("CCPs") within their processes. CCPs are points, steps, or procedures where some form of control can be applied and a food safety hazard can be reduced or eliminated. The processor or manufacturer may need to measure a variety of parametric indicators for each CCP (e.g., time and temperature measurements to verify a cooking process), identify deviations from statistically acceptable ranges, perform trend analysis of such deviations, and document the data to show corrective actions taken in compliance with the HACCP guidelines. The ability of the system 100, 200, 300, 400 to increase the accuracy, reliability, and reproducibility of not just bioluminescence measurements but the attendant record keeping associated with the data collection is therefore highly desirable.

One way of increasing the accuracy, reliability and reproducibility is by providing the sample collection and analysis system with the ability to identify a probe assembly 800 inserted into the dark chamber assembly 900. Providing a machine readable identifier on the probe assembly 800 permits the sample collection and analysis system to verify or authenticate the probe assembly 800. Verification or authentication of the probe assembly 800 can provide a degree of assurance that the probe assembly 800 is both physically and chemically compatible with the sample collection and analysis system. Physical compatibility is important, for example to ensure a tight fit of the probe assembly 800 in the intermediate stays 916 to limit the intrusion of stray photons into the dark chamber 906. Chemical compatibility is important, for example to ensure that the wavelengths of the photons emitted by the bioluminescent sample fall within the range of sensitivity of the photodiode(s) 912 of the photon detection assembly 910. By providing the user with assurances that the probe assembly 800 is both physically and chemically compatible with the sample collection and analysis system, user confidence is increased and the overall quality of the HACCP program is improved. Such identification can provide the user with an assurance of quality, that the probe assembly 800 used with the sample collection and analysis system is approved for use by the system manufacturer or distributor, and that the probe assembly 800 is not counterfeit or otherwise inferior to products supplied by the manufacturer or distributor.

In response to the detection of an authorized probe assembly 800 that is physically and chemically compatible with the sample collection and analysis system, the system can enter a normal operating mode, reading the bioluminescence of the sample 1308 contained within the probe assembly 800. Test results can be reported via the user interface 102 and stored along with any associated location, time, and date data within the non-transitory storage medium 506. In response to the detection of an unauthorized probe assembly 900, for example a probe assembly that is counterfeit or physically or chemically incompatible with the sample collection and analysis system, the system can display an indicator on the user interface 102 indicating the probe assembly 900 is incompatible with the system, and can inhibit the bioluminescence reading of the sample contained within the probe assembly 900. Such a system can also be used to dissuade nefarious use of the sample collection and analysis system, for example by using the same probe assembly 800 for a number of different HACCP test points.

Figure 14A:
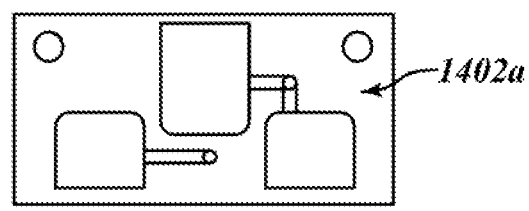
FIG. 14A is a top plan view of an example electronic scanning device useful in verifying and authenticating electronically encoded probe assemblies, according to an illustrated embodiment described herein.
Figure 14B:
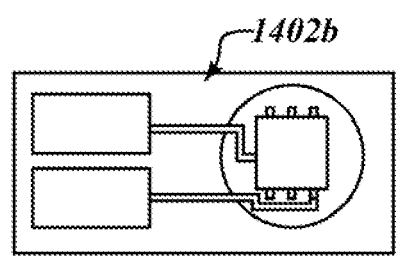
FIG. 14B is a top plan view of an example electronic scanning device useful in verifying and authenticating electronically encoded probe assemblies, according to another illustrated embodiment described herein.

The system 100, 200, 300, 400 may identify the identity, physical construction, or chemical makeup of the probe assembly 800 using one or more methods, including the optical scanning of identifying marks on the probe assembly 800 or the radio frequency scanning of identifying electronic devices in the probe assembly 800. FIGS. 14A and 14B shows several circuit boards, each containing an example electronic scanning device 1402a, 1402b useful in scanning and identifying one or more electronic identifiers carried by the probe assembly 800. In some instances, such electronic scanning devices 1402 may generate one or more radio frequency (RF) interrogation signals to interrogate a radio frequency identification (RFID) tag or similar electronic transponder that is attached to or embedded within the probe assembly 800. Data returned to the electronic scanning device 1402 in the form of an electronic or RFID response signal may include items such as an authentication code, physical dimensions of the probe assembly 800, and the reagents present in the probe assembly 800. In other instances, the electronic scanning devices 1402 may transmit one or more data streams or codes to an electronic tag embedded within the probe assembly 800 and monitor the response from the electronic tag to verify or authenticate the probe assembly 800 to the system. Since the probe assembly 800 is visible electronically to the electronic scanning device 1402, the scanner may be flexibly positioned within the housing 104, 204, 304, 404, for example in a location that is proximate but not necessarily integrated with the dark chamber assembly 900.

Figure 15A:
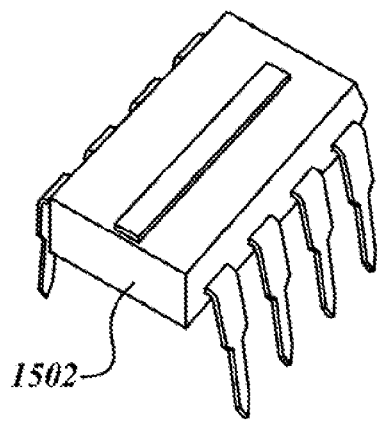
FIG. 15A is a perspective view of an example optical scanning device useful in verifying and authenticating optically encoded probe assemblies, for example probe assemblies bearing one or more authentifiers, according to an illustrated embodiment described herein.
Figure 15B:
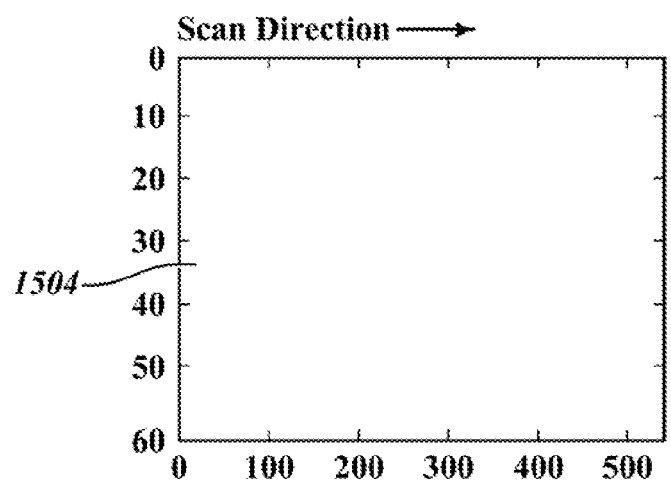
FIG. 15B is a top plan view of an authentifier trade name or trademark, carried on a sample holder or probe assembly, according to an illustrated embodiment described herein.

FIG. 15A shows one example of an optical scanning device 1502 capable of reading an authentifier 1504 illustrated in FIG. 15B. The authentifier 1504 may be carried on a surface of the probe assembly 800. In at least some instances, the authentifier may be debossed, embossed, printed or otherwise inscribed or applied to or on the flat of the D-shaped first portion 812 of the probe assembly 800.

The optical scanning device 1502 can include a photodiode array configured to read electromagnetic radiation reflected from a debossed, embossed, printed or otherwise inscribed or applied authentifier 1504 (e.g., trademark, trade name, logo) carried by the surface of the probe assembly 800 as the authentifier 1504 passes proximate the optical scanning device 1502. In at least some instances, the electromagnetic radiation used to illuminate the authentifier 1504 may be integral with or disposed proximate the optical scanning device 1502 to illuminate the authentifier 1504 on the probe assembly 800. In at least some instances, the accuracy or resolution of the optical scanning device 1502 may be enhanced or otherwise increased by placing one or more self-focusing lenses (e.g., SELFOC® lenses by GoFoton® Group) between the optical scanning device 1502 and the authentifier 1504.

The optical scanning device 1502 converts the authentifier 1504 into an electronic signal by reading the electromagnetic radiation reflected by the authentifier 1504. The electronic signal provided by the optical scanning device 1502 can be compared to one or more reference signals to determine whether a substantial similarity exists between the electronic signal supplied by the optical scanning device 1502 and at least one of the reference signals. In such a manner, the optical scanning device 1502 is able to electronically "read" and "identify" an authentifier carried by the probe assembly 800.

The use of an optical scanning device 1502 requires at least a partial line of sight between the optical scanning device 1502 and the authentifier 1504. As a consequence, the optical scanning device 1502 may be disposed at least partially within a port or similar aperture that is formed in the dark chamber assembly 900. In some instances the optical scanning device 1502 may be disposed external to the dark chamber assembly 900, for example the optical scanning device 1502 may be disposed external to the aperture 904 defining the entrance to the dark chamber assembly 900 and proximate the probe insertion port 118.

In at least one instance, the optical scanning device 1502 may be positioned in an aperture on the dark chamber assembly 900 such that the first portion 812 of the first cylindrical member carrying the authentifier 1504 passes before the optical scanning device 1502 as the probe assembly 800 is inserted into the dark chamber assembly 900. In other instances, the optical scanning device 1502 may be positioned in an aperture on the dark chamber assembly 900 such that the authentifier 1504 is opposite the optical scanning device 1502 when the probe assembly 800 is positioned within the dark chamber assembly 900, for example after the cover assembly 1002 is placed in a "closed" position.

Figure 16:
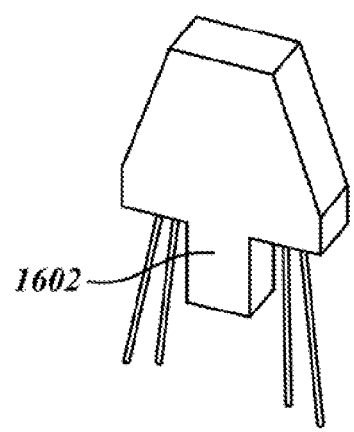
FIG. 16 is a perspective view of an example infrared scanning device useful in verifying and authenticating infrared encoded probe assemblies, for example probe assemblies bearing one or more infrared sensitive designs, machine readable codes, or trademarked logos, according to an illustrated embodiment described herein.

FIG. 16 shows an example infrared scanning device 1602 capable of reading an authentifier printed in an infrared responsive media on the surface of the probe assembly 800. The infrared scanning device 1602 can include one or more infrared emitters and one or more detectors that are able to illuminate a printed authentifier on the probe assembly 800 with electromagnetic radiation in the infrared spectrum. A portion of the infrared light is reflected back to the detector, which converts the infrared light reflected by the printed authentifier on the probe assembly 800 to an electronic signal. The printed authentifier on the surface of the probe assembly 800 may include, but is not limited to, a trade name, a trademark, a barcode, a matrix or area code, or the like.

The signal provided by the infrared scanning device 1602 carries data indicative of the printed authentifier on the probe assembly 800. The signals returned from substantially similar printed authentifiers should, themselves, be substantially similar. One or more reference signal profiles stored, for example in the non-transitory storage media 506, may therefore be used to verify or authenticate the signal read by the infrared scanning device 1602 from the printed authentifier on the probe assembly 800. In some instances, the at least one processor 504 can compare the signal provided by the infrared scanning device 1602 with one or more stored reference signal profiles to determine whether the signal supplied by the infrared scanning device 1602 substantially matches one or more stored reference signal profiles. The presence of a reference signal profile match can authenticate the probe assembly 800.

The use of an infrared scanning device 1602 requires at least a partial line of sight between the infrared scanning device 1602 and the printed authentifier on the probe assembly 800. As a consequence, the infrared scanning device 1602 may be disposed at least partially within a port or similar aperture that is formed in the dark chamber assembly 900. In some instances the infrared scanning device 1602 may be disposed external to the dark chamber assembly 900, for example the infrared scanning device 1602 may be disposed external to the aperture 904 defining the entrance to the dark chamber assembly 900 and proximate the probe insertion port 118.

In at least one instance, the infrared scanning device 1602 may be positioned in an aperture on the dark chamber assembly 900 such that the first portion 812 of the first cylindrical member carrying the printed authentifier passes before and is infrared illuminated by the infrared scanning device 1602 as the probe assembly 800 is inserted into the dark chamber assembly 900. In other instances, the infrared scanning device 1602 may be positioned in an aperture on the dark chamber assembly 900 such that the printed authentifier on the probe assembly 800 is opposite the infrared scanning device 1602 when the probe assembly 800 is positioned within the dark chamber assembly 900, for example after the cover assembly 1002 is placed in a "closed" position.

The use of electronic signals provided by electronic scanning devices 1402, optical scanning devices 1502, infrared scanning devices 1602, or combinations thereof, to identify and authenticate a probe assembly 800 by comparison to one or more reference signals, advantageously permits periodic updates and refreshes of a reference signal library containing the one or more reference signals that is stored in the non-transitory storage media 506. Such updates and refreshes of the reference signal library can be delivered electronically, for example over the Internet by synchronizing the sample collection and analysis system with an Internet-connected external device. Such updates and refreshes of the reference signal library can be delivered as software, for example on a removable, non-transitory, storage media (e.g., secure digital cards, flash drives, and the like) that are communicably coupleable to the sample collection and analysis system.

Further, the use of electronic signals to verify or authenticate the probe assembly 800 can also improve traceability and accountability in an HACCP program by permitting the association of a particular probe assembly 800 with a particular test result. Electronic signals may also be used for other purposes, for example a reagent expiration date may be encoded on a probe assembly 800 containing an integral reagent chamber. Such uses can increase confidence in the results obtained and assist in ensuring the veracity of the HACCP records generated using the sample collection and analysis system.

Figure 17:
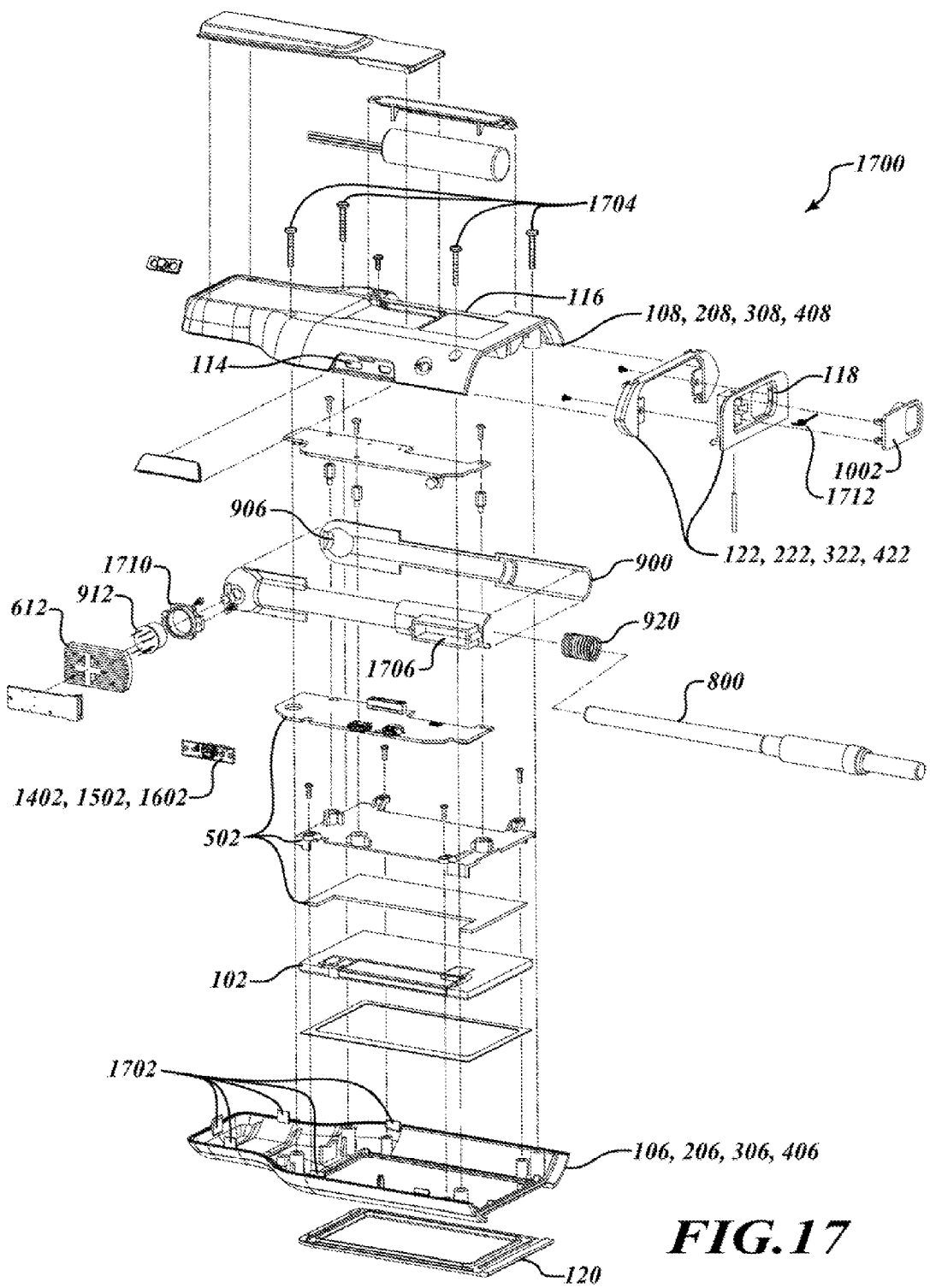
FIG. 17 is an exploded view of an example sample collection and analysis system including an ergonomically shaped and sized instrument and a sample holder or probe assembly, according to one illustrated embodiment described herein.

FIG. 17 shows an example sample collection and analysis system 1700. Visible in FIG. 17 are the physical and spatial arrangements of the various parts, components, systems, and devices described in detail above. For example the front portion of the housing 106, 206, 306, 406 and the rear portion of the housing 108, 208, 308, 408 are shown separated, making visible various alignment tabs 1702 and threaded fasteners 1704 useful in physically aligning and coupling the front portion to the rear portion to form the housing 104, 204, 304, 404. Also visible in FIG. 17 is a two-piece dark chamber assembly 900. An aperture 1706 accommodating a scanning device (e.g., an electronic 1402, optical 1502, or infrared 1602 scanning device) is visible on the intermediate section 902 of the dark chamber assembly. The dark chamber assembly 900 shown in FIG. 17 includes an example spherical dark chamber 906. A multi-piece logic board 502 is depicted in FIG. 17. At least one of the logic boards 502 can include one or more communications interfaces 1708 that physically align with the one or more communications ports 114 that in the housing depicted in FIG. 17 are located on the rear portion 108, 208, 308, 408.

The heat sink 612 depicted in FIG. 17 includes two thermally conductive members. The first thermally conductive member is an extended surface, i.e., a finned heat transfer device that passively, convectively, transfers heat to the ambient environment about the first thermally conductive member. The second thermally conductive member is a thermally conductive toroidal member that is disposed about the photodiode(s) (e.g., MPPC) 912 and thermally conductively coupled to the finned first thermally conductive member. Heat generated by the photodiodes 912 is transferred by conduction and convection to the toroidal second member and then transferred via conduction to the first thermally conductive member. These elements constitute at least a portion of a thermal management subsystem, which may include passive (e.g., fins, pins) and/or active (e.g., fans, electric coolers) heat transfer elements or components.

A two-piece housing top 122, 222, 322, 422 is depicted in FIG. 17. Visible on the housing top is the probe insertion port 118. The cover assembly 1002 includes a hinged door and a torsion spring 1712 to maintain the hinged door in an open position when the hinged door is pivoted away from the probe insertion port 118. Maintaining the hinged door in an open position can assist in the passage of the probe assembly 800 into the dark chamber assembly 900.

Figure 18:
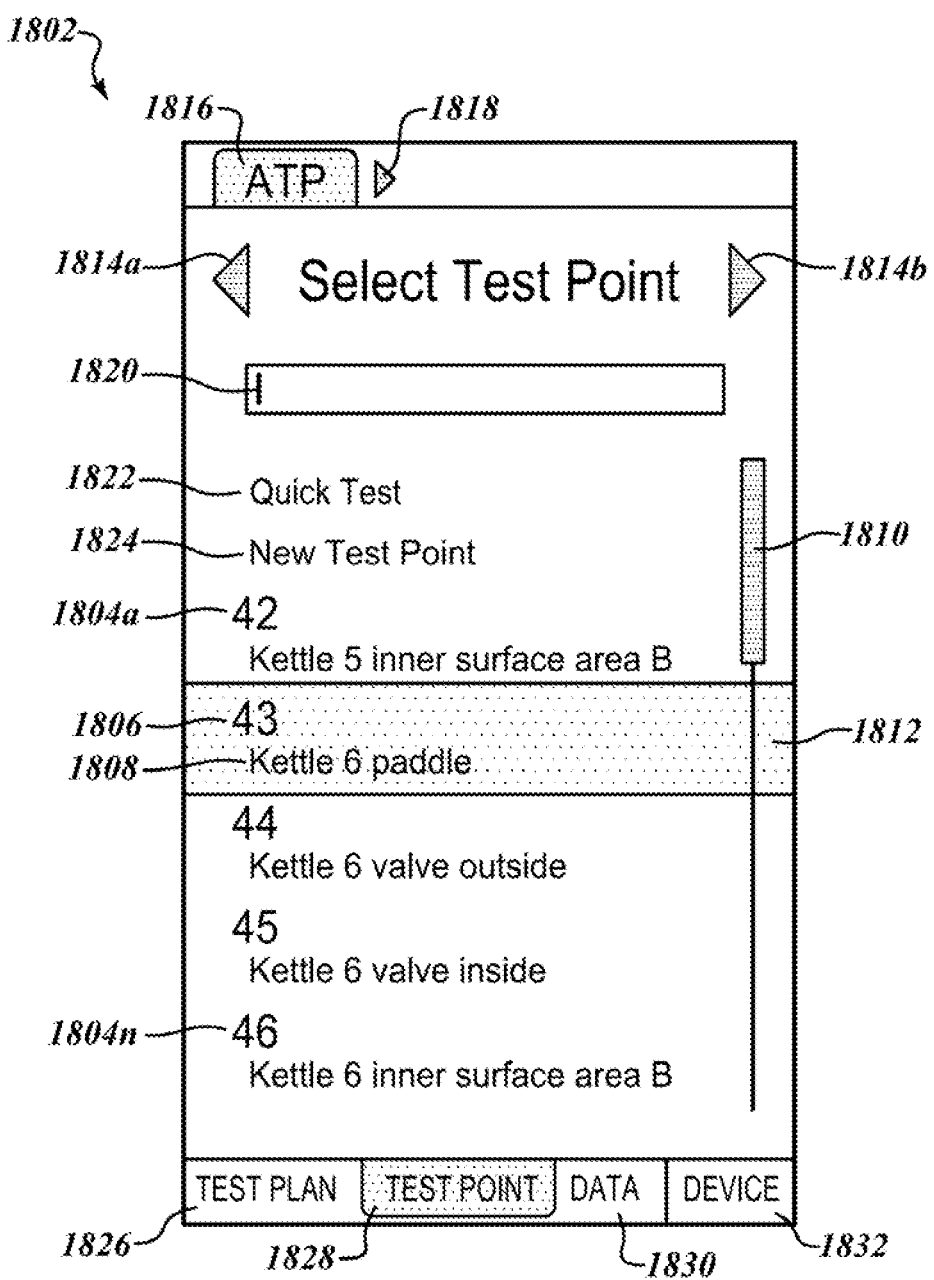
FIG. 18 is a screen print of a select test point via scrolling screen of a graphical user interface according to one illustrated embodiment, which may be presented via a processor on a display, for instance a touch-sensitive or touch-responsive display, of a portable monitoring instrument such as those described above.

FIG. 18 shows a select test point via scrolling screen 1802 of a graphical user interface according to one illustrated embodiment, which may be presented via a processor on a display, for instance a touch screen display, of a portable monitoring instrument such as those described above.

The select test point via scrolling screen 1802 displays for selection by an end user a number of test point identifiers 1804*a*-1804*n* (two called out, collectively 1804) for respective test points. The test points and associated test point identifiers may be defined by the end user, company, or some other entity. As illustrated, the test point identifiers 1804 may be presented as a list. The test point identifiers 1804 may take the form of a test point number 1806 (one called out) and/or a test point human recognizable name or description 1808 (one called out). Selection and dragging of a user selectable scroll icon 1810 allows a user to scroll through the list of test point identifiers 1804 in a current page or window, allowing identification and selection of a desired one of the test point identifiers 1804 (e.g., test point number 1806, test point name or description 1808). The currently identified test point identifier 1804 is visually distinguished, for example via highlighting 1812. A user input, for example a single tap or double tap, selects the identified test point identifier 1804.

Selection of one of a pair of user selectable page icons 1814*a*, 1814*b* (collectively 1814) causes presentation of additional pages or windows of test point identifiers 1804. The pages or widows may include test point identifiers 1804 for a same process or for different processes, which may or may not be related to one or another. The test point identifiers 1804 may be logically grouped on different pages or windows, for example test identifiers 1804 may be grouped corresponding to a respective location, system, subsystem or portion of a process, collectively referred to as zones. For instance, a food manufacturing process may be logically divided or segmented into various processes, for example preparing raw ingredients, mixing ingredients, cooking, cooling, quality assurance, and packaging, each identified as a respective zone. Each segment or zone may be associated with respective equipment, work surfaces and/or personnel, and each assigned a respective page or window with one or more test points. Thus, various pieces of equipment associated with mixing may be assigned various test points and associated test point identifiers 1804 for a given zone grouped on a common page or windows. Selecting a left facing arrow head 1814*a* may bring up a set of test point identifiers 1804 associated with a first zone that, for example, occur earlier in the food preparation of manufacturing process, while selecting a right facing arrow head 1814*b* may bring up a set of test point identifiers 1804 associated with a second zone that occur later in the food preparation or manufacturing process. Earlier steps or operations may be assigned lower or smaller test point numbers 1806, while later steps or operations assigned higher or larger test point numbers 1806. Test point numbers may reflect the zones with which the associated test points are grouped. For example, zones may be identified by digits to the left of a decimal point and/or digits to the right of the decimal point. One or more test points may be associated with a respective one of the zones. Various groups of sets and subsets may be identified using places in a multi-digit test point identifier number.

The select test point via scrolling screen 1802 includes a test type indicator 1816 that indicates a type of test being performed. For example, as illustrated, an ATP indication is displayed indicating that an ATP test is to be performed. Selection of a user selectable test selection icon 1818 allows the user to select other tests, for example, pH, temperature, pressure, dissolved gases, conductivity, reduction potential, and/or specific ions.

The select test point via scrolling screen 1802 may include a test point entry box 1820, selection of which causes display of a virtual keypad or virtual keyboard (not shown). The user may then key in a test identifier 1804, and select an enter key to select the desired test point.

The select test point via scrolling screen 1802 may include a quick test user selectable icon 1822, selection of which executes a quick test.

The select test point via scrolling screen 1802 may include a new test point user selectable icon 1824. User selection of the new test point user selectable icon 1824 may cause presentation of a new test point creation window. Such allows the end user to create new test points and associated test point identifiers 1806, 1808.

The select test point via scrolling screen 1802 may include a navigation bar with a number of user selectable icons to allow navigation to various modes and associated pages or windows. For example, the navigation bar may include a test plan user selectable icon 1826, a test point user selectable icon 1828, a data user selectable icon 1830 and a device user selectable icon 1832. The currently selected mode or page or window may be visually distinguished, for example via highlighting as illustrated.

Figure 19:
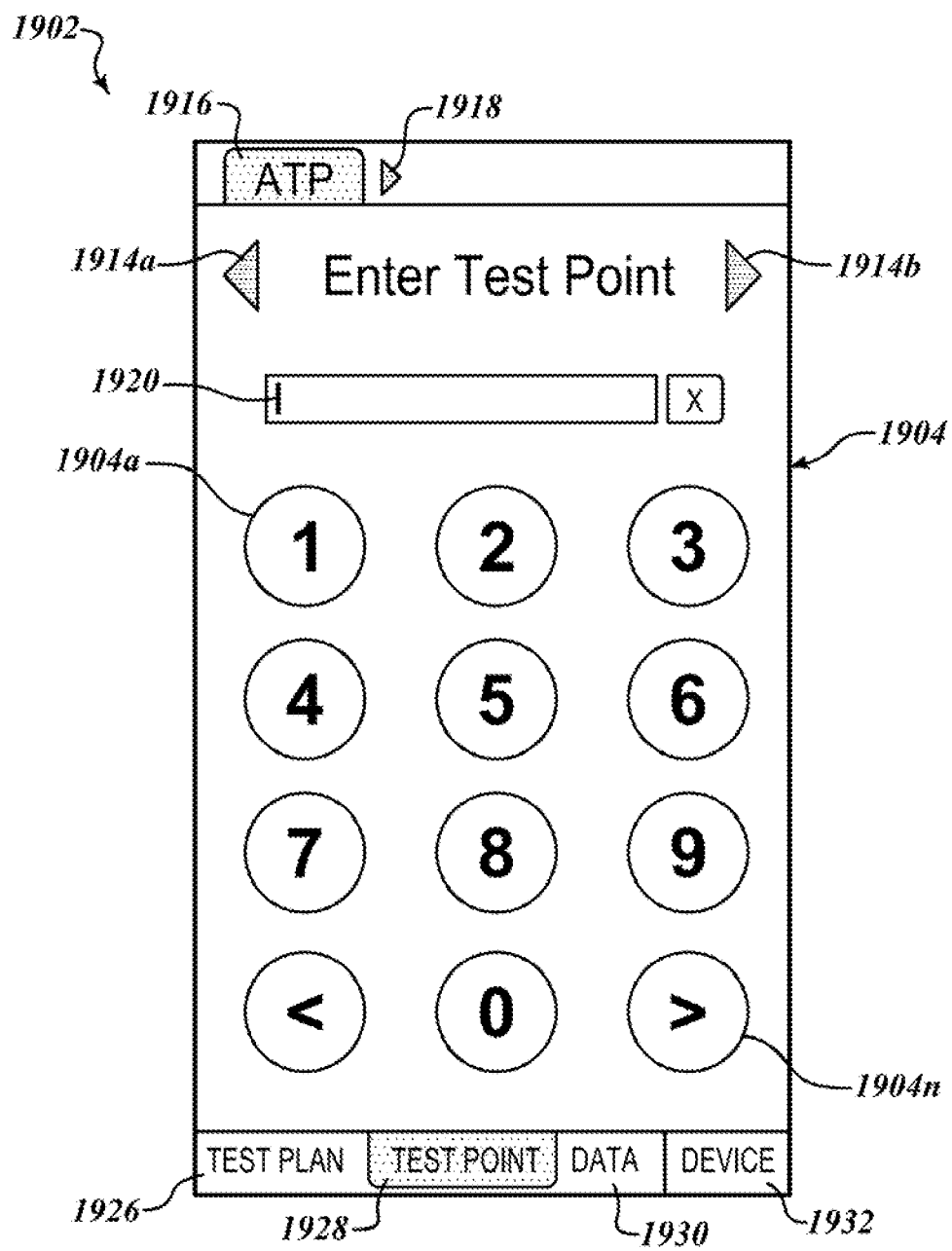
FIG. 19 is a screen print of a select test point via entry screen of a graphical user interface according to one illustrated embodiment, which may be presented via a processor on a display, for instance a touch-sensitive or touch-responsive display, of a portable monitoring instrument such as those described above.

FIG. 19 shows a select test point via entry screen 1902 of a graphical user interface according to one illustrated embodiment, which may be presented via a processor on a display, for instance a touch screen display, of a portable monitoring instrument such as those described above. The select test point via entry screen 1902 has a number of constructs or elements that are identical or similar to those of the select test point via scrolling screen 1802. Similar or identical constructs or elements (e.g., user selectable icons, menus, indicators, scroll bars and controls) are identified using the same reference numbers as set out above, and discussion of those elements is not repeated in the interest of brevity. Only significant differences are discussed below.

The select test point via entry screen 1902 includes a virtual keypad 1904 which allows the user to enter a test point identifier 1804 into the test point entry box 1820. The user simply touches the user selectable virtual keys 1904a-1904n (twelve shown, only two called out) as desired to enter a test point identifier 1804. As illustrated, the virtual keypad 1904 includes virtual keys 1904a-1904n corresponding to the digits 0-9 and left and right paging arrows, allowing entry of a test point number 1806 (FIG. 18) or scrolling to different pages. Alternatively, the virtual keypad 1904 may display alpha or other characters and may include a greater number or smaller number of virtual keys. The virtual keypad 1904 may be context sensitive, for example displaying different alphanumeric or other characters based on context. Optionally, selection of user selectable page icons 1814 or left and right arrow virtual keys may cause presentation of different virtual keypads.

Figure 20:
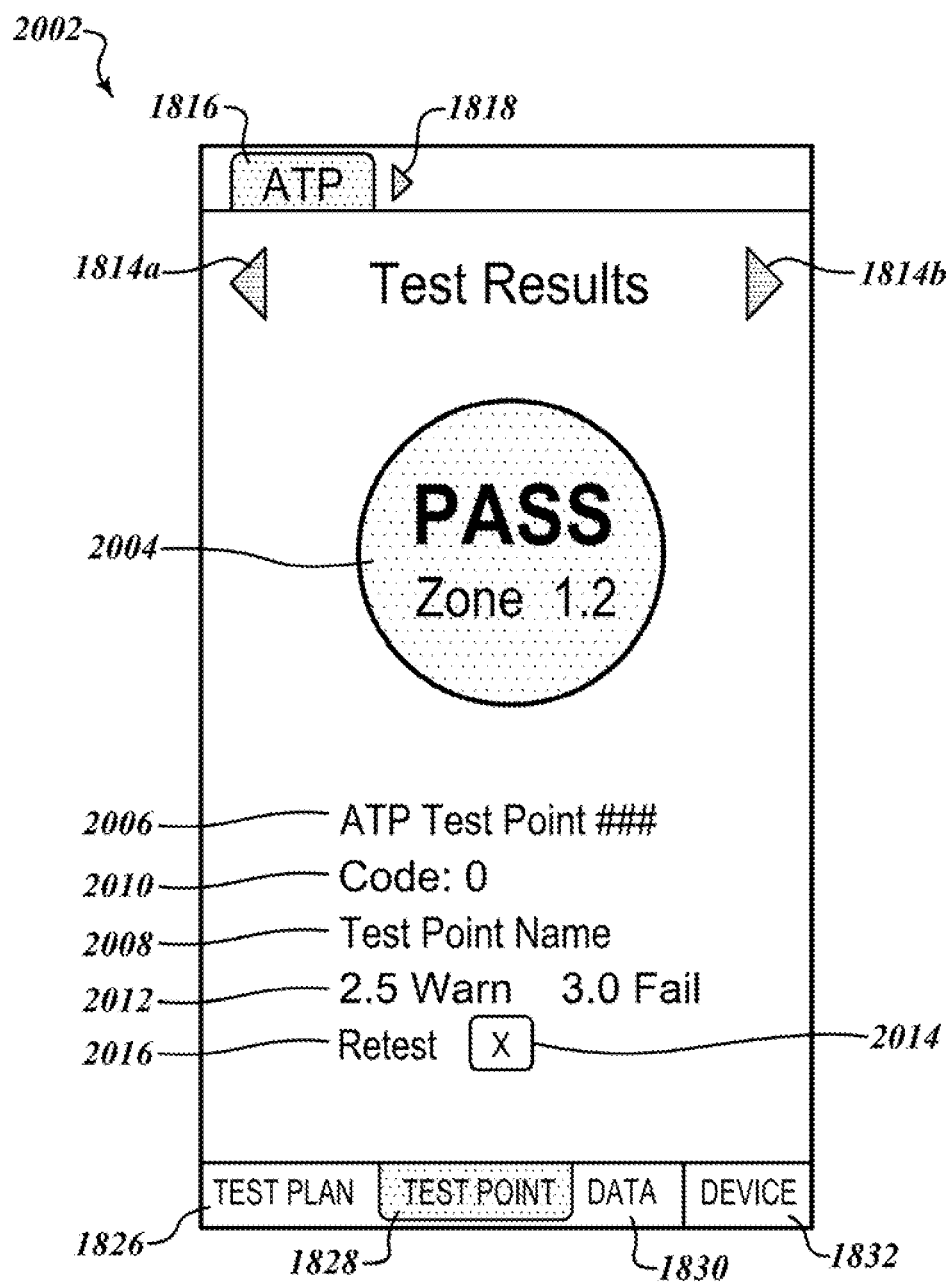
FIG. 20 is a screen print of a test results screen of a user interface displaying a passing result for a test zone according to one illustrated embodiment, which may be presented via a processor on a display, for instance a touch-sensitive or touch-responsive display, of a portable monitoring instrument such as those described above.

FIG. 20 shows a test results screen 2002 of a graphical user interface displaying a passing result for a test zone according to one illustrated embodiment, which may be presented via a processor on a display, for instance a touch screen display, of a portable monitoring instrument such as those described above. The test results screen 2002 has a number of constructs or elements (e.g., user selectable icons, menus, indicators, scroll bars and controls) that are identical or similar to those of the select test point via scrolling screen 1802 (FIG. 18). Similar or identical elements are identified using the same reference numbers as set out above, and discussion of those elements is not repeated in the interest of brevity. Only significant differences are discussed below.

The test results screen 2002 displays results for a test. The results include an easy to recognize visual indication 2004 of the results, in this case a large circle with the description "PASS" and an identification of a zone with which the particular test point is associated. The results of the tests are further emphasized by color, for example using the color green to indicate a passing result.

The test results screen 2002 may also include a set of test results details. These may include an indication of the test point number 2006, test point name 2008, a value of a code 2010, values of thresholds (e.g., warning threshold 2012, fail threshold 2014), and an indication 2016 whether retesting should be performed.

Figure 21:
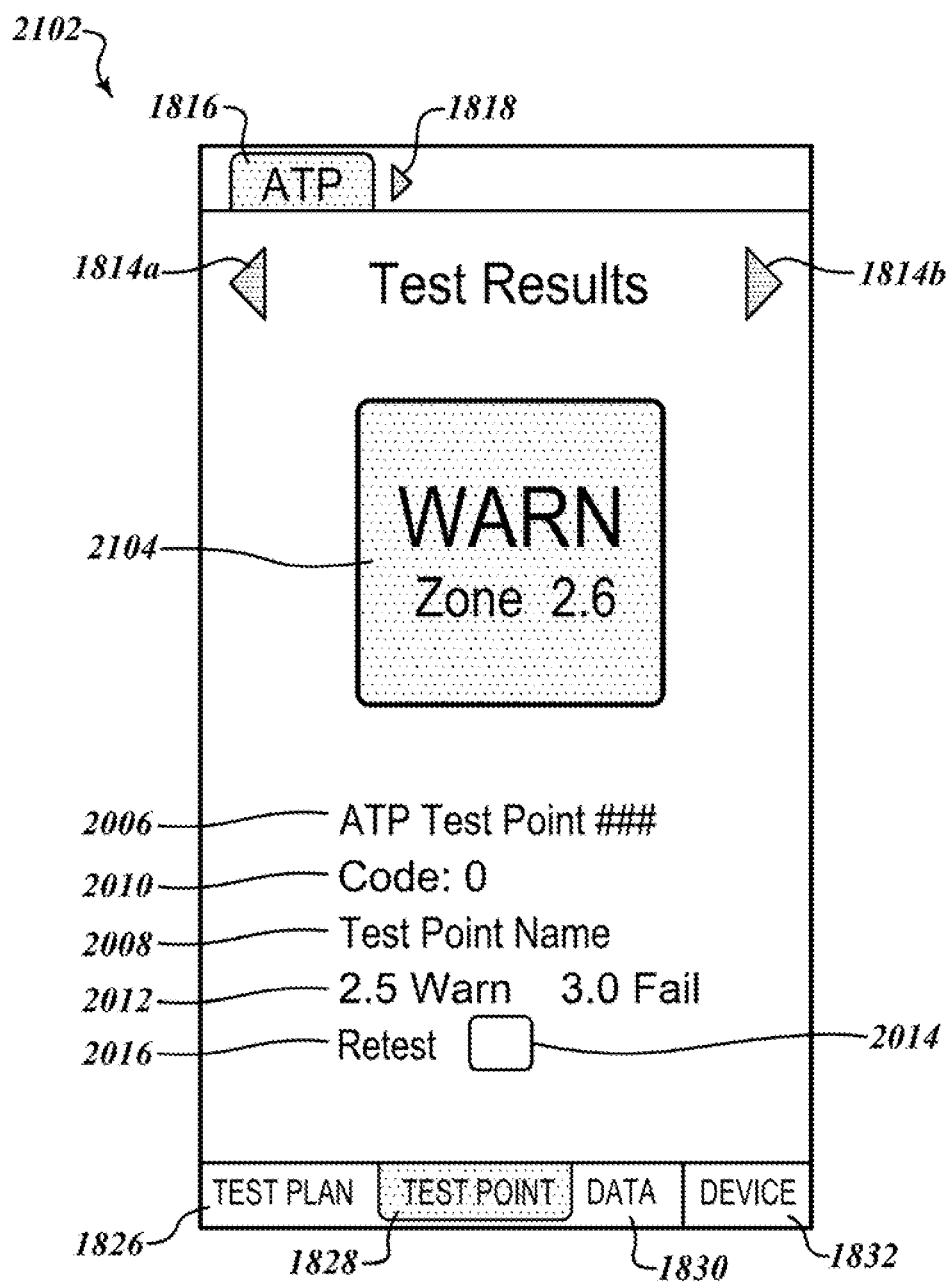
FIG. 21 is a screen print of a test results screen of a user interface displaying a warning result for a test zone according to one illustrated embodiment, which may be presented via a processor on a display, for instance a touch-sensitive or touch-responsive display, of a portable monitoring instrument such as those described above.

FIG. 21 shows a test results screen 2102 of a graphical user interface displaying a warning result for a test zone according to one illustrated embodiment, which may be presented via a processor on a display, for instance a touch screen display, of a portable monitoring instrument such as those described above. The test results screen 2102 has a number of constructs or elements (e.g., user selectable icons, menus, indicators, scroll bars and controls) that are identical or similar to those of the test results screen 2002. Similar or identical constructs or elements are identified using the same reference numbers as set out above, and discussion of those elements is not repeated in the interest of brevity. Only significant differences are discussed below.

The test results screen 2102 displays results for a test. The results include an easy to recognize visual indication 2102 of the results, in this case a large square with the description "WARN" and an identification of a zone with which the particular test point is associated. The results of the tests are further emphasized by color, for example using the color yellow to indicate a marginal result.

Figure 22:
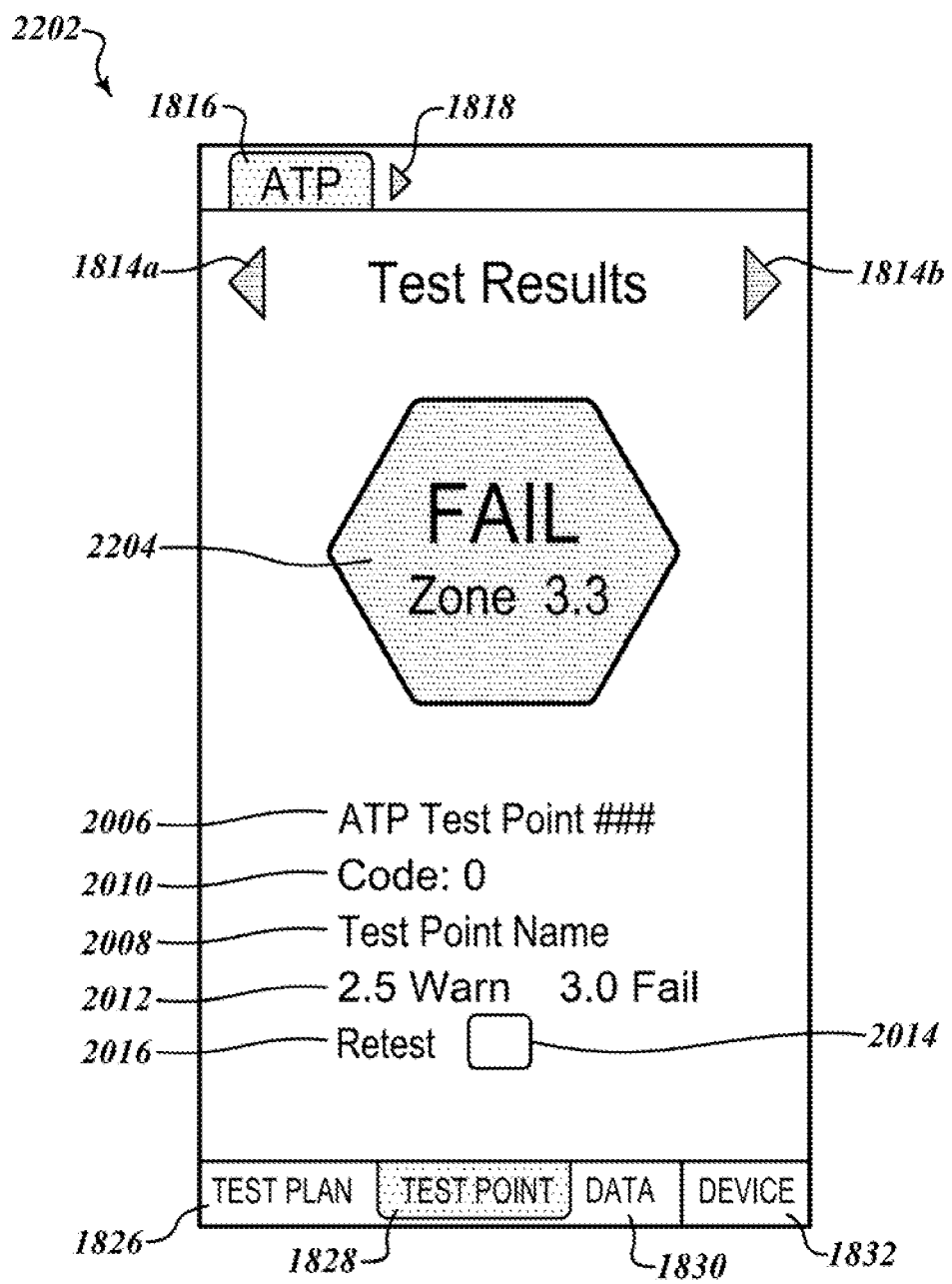
FIG. 22 is a screen print of a test results screen of a user interface displaying a failing result for a test zone according to one illustrated embodiment, which may be presented via a processor on a display, for instance a touch-sensitive or touch-responsive display, of a portable monitoring instrument such as those described above.

FIG. 22 shows a test results screen 2202 of a graphical user interface displaying a failing result for a test zone according to one illustrated embodiment, which may be presented via a processor on a display, for instance a touch screen display, of a portable monitoring instrument such as those described above. The test results screen 2202 has a number of constructs or elements (e.g., user selectable icons, menus, indicators, scroll bars and controls) that are identical or similar to those of the test results screen 2002. Similar or identical elements are identified using the same reference numbers as set out above, and discussion of those elements is not repeated in the interest of brevity. Only significant differences are discussed below.

The test results screen 2202 displays results for a test. The results include an easy to recognize visual indication 2204 of the results, in this case a large hexagon with the description "FAIL" and an identification of a zone with which the particular test point is associated. The results of the tests are further emphasized by color, for example using the color red to indicate a failing result.

Figure 23:
FIG. 23 is a screen print of a dashboard screen of a user interface according to one illustrated embodiment, which may be presented on a display via a processor of a computer system, communicatively coupled to a portable monitoring instrument such as those described above.

FIG. 23 shows a dashboard screen 2302 of a user interface according to one illustrated embodiment, which may be presented on a display via a processor of a computer system, communicatively coupled to a portable monitoring instrument such as those described above. The dashboard screen 2302 provides a convenient way for a user to reviewing testing and compliance, and to interact with the one or more pieces of portable monitoring equipment.

The dashboard screen 2302 includes a menu bar 2304 of user selectable icons. Selection of a file user selectable icon 2306 allows the user to save a file, select an existing file or create a new file. Selection of a view raw data user selectable icon 2308 causes presentation of raw data, and optionally a raw data user interface, to the user. Selection of an MVP device user selectable icon 2310 allows the user to select a particular portable monitoring instrument for reporting and/or for calibration. Selection of an options user selectable icon 2312 presents a list of user selectable options. Selection of a support user selectable icon 2314 obtains support for the user. Such may include accessing a user guide, a frequently asked questions list, and/or contacting user support personnel via electronic mail (e.g., email) or a voice line.

The dashboard screen 2302 also includes an indication 2316 of an identity of a currently communicatively coupled piece of portable monitoring equipment. User selection of a user selectable decoupling icon 2317 terminates the communicative coupling to the piece of portable monitoring equipment. The dashboard screen 2302 also includes an indication 2318 of an identity of a currently open file to which the information is saved.

A set of user selectable navigation icons allows the user to navigate between various modes and associated pages or windows. For example, selection of a test reports user selectable icon 2320 provides detailed test reports to the user, optionally with a test reports user interface to allow navigating between and within selected test reports, and/or editing test reports. Selection of an ATP usage reports user selectable icon 2322 provides detailed usage reports to the user, optionally with a usage reports user interface to allow navigating between and within selected ATP usage reports, and/or editing ATP usage reports. Selection of an HACCP compliance report user selectable icon 2324 provides detailed HACCP compliance reports to the user, optionally with an HACCP compliance reports user interface to allow navigating between and within selected HACCP compliance reports, and/or editing HACCP compliance reports. Selection of a test point set up user selectable icon 2326 causes presentation of a test point set up user interface to the user, allowing the user to set up new test points, modify existing test points and/or delete existing test points.

The dashboard screen 2302 includes a number of simplified information presentation boxes for presenting summaries of key information.

The information presentation boxes may include a tests run box 2328 which provides an indication 2328*a* of a total number of tests (e.g., ATP swabs) run for a current period (e.g., monthly), as well as an indication 2328*b* of a target total number of tests for the current period. A color may be used to signify or emphasize a status, for example green where within an acceptable threshold or value of tests have been run, red where outside an acceptable threshold or value of tests have been run, and yellow or magenta where marginal or bordering the acceptable threshold or value of number of tests have been run. Selection of a user selectable report icon 2328*c* causes presentation of a report detailing the tests run.

The information presentation boxes may include a warning results box 2330 which shows an indication 2330*a* of a percentage of tests (e.g., ATP swabs) that resulted in a defined condition or outcome (e.g., warning) for an identified period (e.g., January 1-June 1) 2330*b*. Again, a color may be used to signify a status, for example green where within an acceptable threshold or value of a percentage of tests resulting in a warning result, red where outside an acceptable threshold or value of a percentage of tests resulting in a warning result, and yellow or magenta where marginal or bordering the acceptable threshold or value of a percentage of tests resulting in a warning result. Selection of a user selectable report icon 2330*c* causes presentation of a report detailing warning results.

The information presentation boxes may include a failure results box 2332 which shows an indication 2332*a* of a percentage of tests (e.g., ATP swabs) that resulted in a defined condition or outcome (e.g., failure) for an identified period (e.g., January 1-June 1) 2332*b*. Again, a color may be used to signify a status, for example green where within an acceptable threshold or value of a percentage of tests resulting in a failing result, red where outside an acceptable threshold or value of a percentage of tests resulting in a failing result, and yellow or magenta where marginal or bordering the acceptable threshold or value of a percentage of tests resulting in a failing result. Selection of a user selectable report icon 2332*c* causes display of a report detailing failing results.

The information presentation boxes may include a calibration box 2334 which shows an indication 2334*a* of a date that a piece of portable monitoring equipment was last calibrated and an indication 2334*b* of a next date for calibrating the piece of portable monitoring equipment, for instance in the form of a number of days remaining until the next scheduled calibration. Again, a color may be used to signify a status, for example green where within an acceptable threshold or value of time from last calibration, red where outside an acceptable threshold or value of time from last calibration, and yellow or magenta where marginal or bordering the acceptable threshold or value of a time from last calibration. Selection of a user selectable report icon 2334*c* causes display of a report detailing calibration records.

The dashboard screen 2302 includes a number of simplified graphs or charts for presenting graphical summaries of key information.

The graphs or charts may include a graph or chart 2336 of cleaning effectiveness (%) by test point. Such may indicate effectiveness along one axis 2336*a*, with various tests point presented along another axis 2336*b*. Again, color may be advantageously employed to visually distinguish or emphasize between conditions, for instance green indicting very effective cleaning, yellow marginally effective cleaning and red indicating ineffective cleaning.

The graphs or charts may include a graph or chart 2338 of cleaning effectiveness (%) by sampling plan. Such may indicate effectiveness along one axis 2338*a*, with various items on a sampling plan presented along another axis 2338*b*. Again, color may be advantageously employed to visually distinguish or emphasize between conditions, for instance green indicting very effective cleaning, yellow marginally effective cleaning and red indicating ineffective cleaning Selection of a user selectable report icon 2338*c* may cause presentation of a cleaning effectiveness by sampling plan report.

The graphs or charts may include a graph or chart 2340 of retest effectiveness (%) by test point. Such may indicate effectiveness along one axis 2340*a* showing the percentage of passing, warning and failing results, with various tests point presented along another axis 2340*b*. Again, color may be advantageously employed to visually distinguish or emphasize between conditions, for instance green indicating a compliant value, yellow indicating a marginally compliant value that is close to non-compliance, and red indicating a non-compliant value.

A window scroll bar 2342 allows a user to scroll up and down in the window of the dashboard screen 2302.

Figure 24:
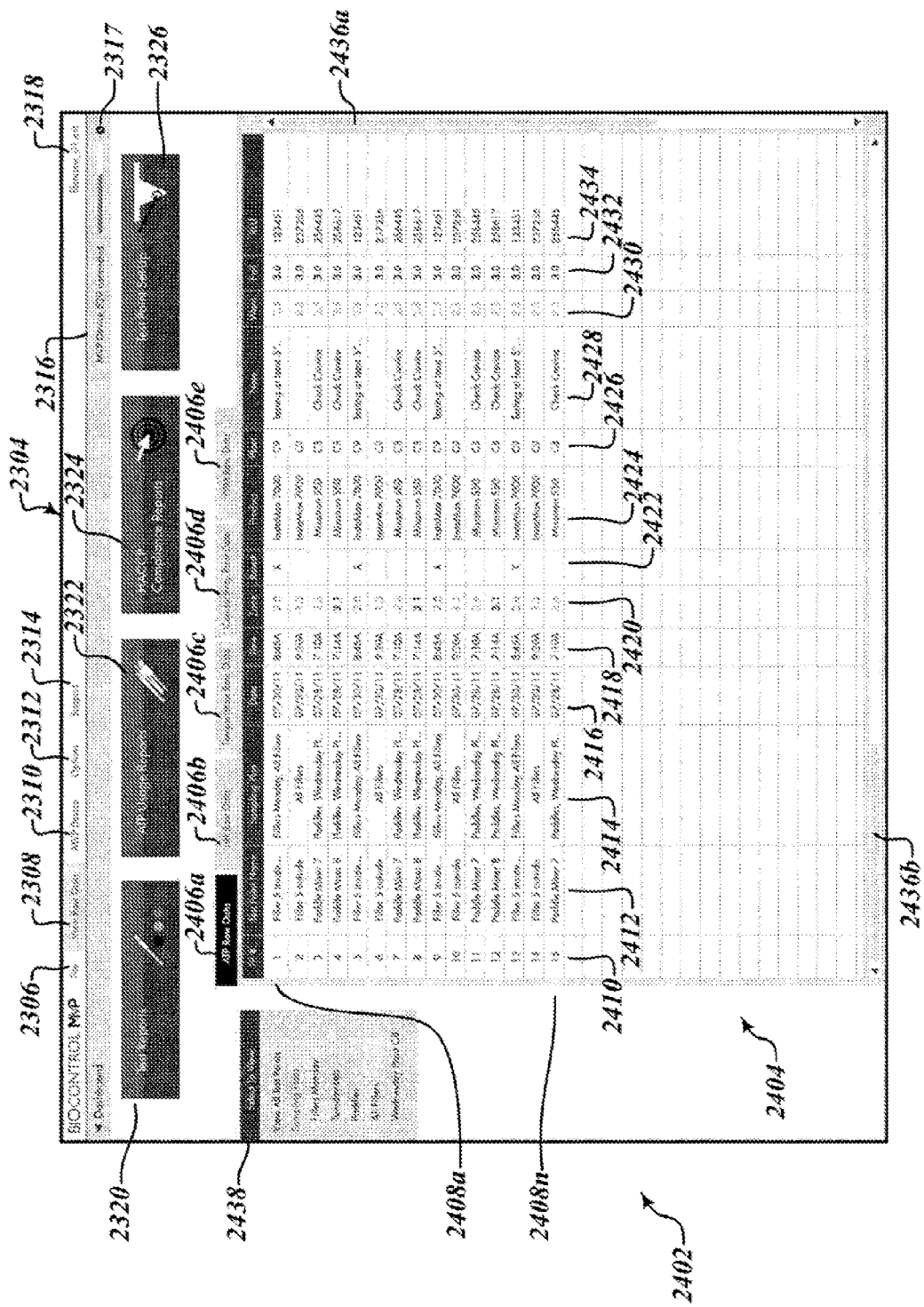
FIG. 24 is a screen print of a raw data screen of a user interface according to one illustrated embodiment, which may be presented on a display via a processor of a computer system, communicatively coupled to a portable monitoring instrument such as those described above.

FIG. 24 shows a raw data screen 2402 of a user interface according to one illustrated embodiment, which may be presented on a display via a processor of a computer system, communicatively coupled to a portable monitoring instrument such as those described above. The raw data screen 2402 has a number of constructs or elements (e.g., user selectable icons, menus, indicators, scroll bars and controls) that are identical or similar to those of the dashboard screen 2302 (FIG. 23). Similar or identical constructs or elements are identified using the same reference numbers as set out above, and discussion of those elements is not repeated in the interest of brevity. Only significant differences are discussed below.

The raw data screen 2402 includes a raw data chart or table 2404 for presenting raw data for various test points and associated information. The raw data screen 2402 also includes a number of user selectable raw data tabs 2406a-2406e (five shown, collectively 2406), which a user may select to determine what type of raw data is presented in the raw data chart or table 2404. For example, the raw data screen 2402 may include an ATP raw data tab 2406a, pH raw data tab 2406b, temperature raw data tab 2406c, conductivity raw data tab 2406d, PPM raw data tab 2406e. A currently selected raw data tab 2406a may be visually indicated or emphasized, for example via highlighting or a color change.

The raw data may, for example, be presented in rows and columns. For instance, FIG. 24 illustrates the presentation of ATP raw data, each row 2408a-2408n (only two called out) corresponding to a respective test point. The columns may include a test point number column 2410 which identifies the test point by the test point number. A point name column 2412 may identify the test point by test point name. A sampling plan column 2414 may identify a portion of a sampling plan to which the raw data relates. A date column 2416 and a time column 2418 may indicate a date and time at which the raw data was captured. A zone column 2420 which includes an indication of a zone with which the test point and related specific raw data is associated. A retest column 2422 may provide an indication of whether the raw data is from a retest of the test point. A product identification column 2424 may provide an identifier that identifies a piece of equipment or work surface with which the specific raw data is associated. A plant identification column 2426 may provide a plant identifier that identifies a plant or other manufacturing or production facility at which the test point is located. A note column 2428 includes notes related to the respective test point. A warn column 2430 includes an indication of a warning threshold at which a warning result occur. A fail column 2432 includes an indication of a failure threshold at which a failure or failing result occurs. A raw RIU column 2434 includes an indication of the raw RIU for the respective test point.

Other raw data may be reported based on user selection of the tabs 2406, for example pH raw data, temperature raw data, conductivity raw data, or parts per million (PPM) raw data.

Vertical and horizontal scroll bars 2436a, 2436b allow the user to scroll through the raw test data chart or table 2404.

The raw data screen 2402 may optionally include a filter menu 2438 that provides a number of user selectable options to filter the data presented in the raw data chart or table 2404. For example, the user may select to view all test points, as illustrated. Alternatively, the user may filter by sampling plans, for example by location, equipment, zone and/or date.

Figure 25:
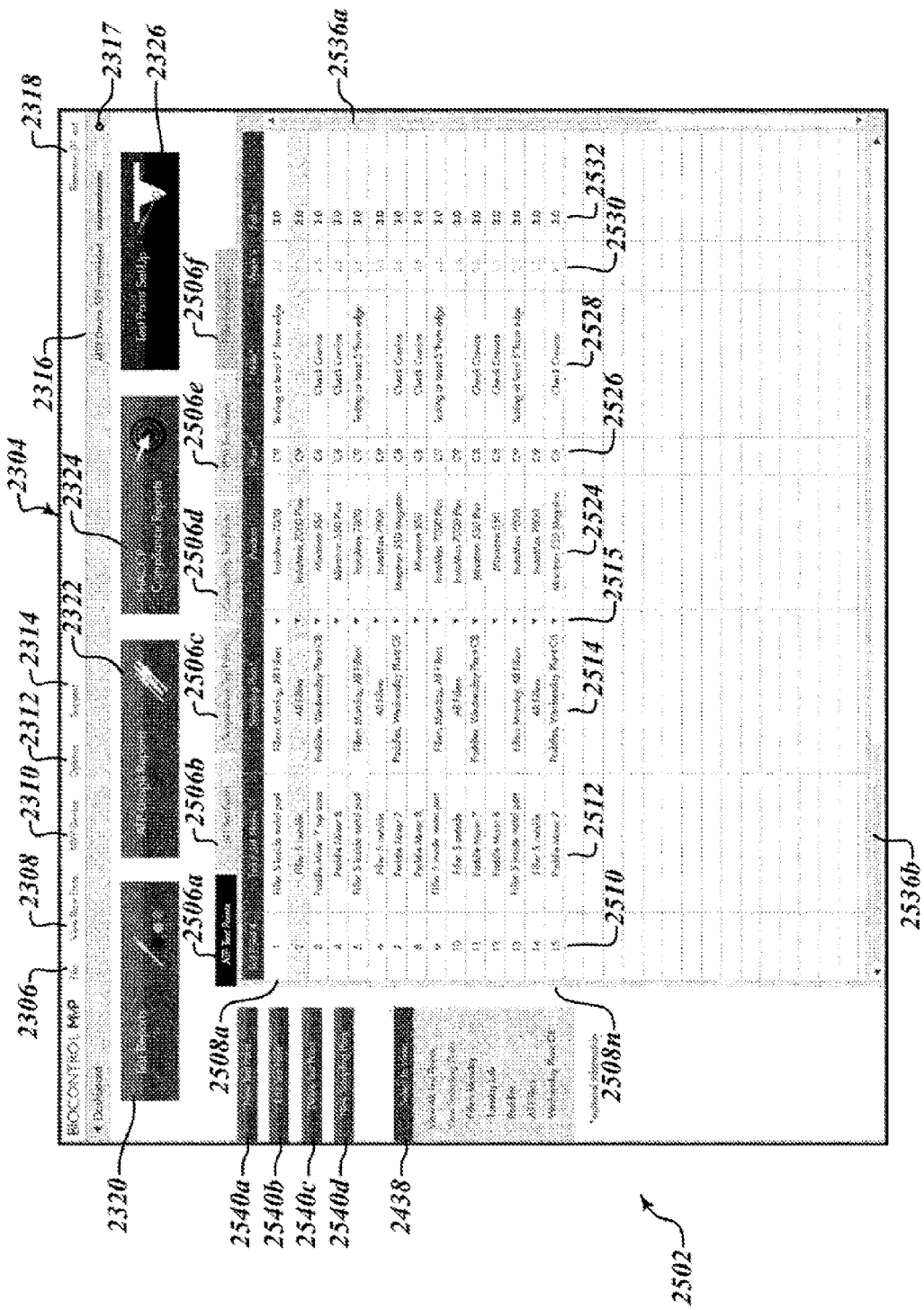
FIG. 25 is a screen print of a test point set up screen of a user interface according to one illustrated embodiment, which may be presented on a display via a processor of a computer system, communicatively coupled to a portable monitoring instrument such as those described above.

FIG. 25 shows a test point set up screen 2502 of a user interface according to one illustrated embodiment, which may be presented on a display via a processor of a computer system, communicatively coupled to a portable monitoring instrument such as those described above. The test point set up screen 2502 has a number of constructs or elements (e.g., user selectable icons, menus, indicators, scroll bars and controls) that are identical or similar to those of the dashboard screen 2302 (FIG. 23) or raw data screen 2402 (FIG. 24). Similar or identical constructs or elements are identified using the same reference numbers as set out above, and discussion of those elements is not repeated in the interest of brevity. Only significant differences are discussed below.

The test point set up screen 2502 includes a test point set up chart or table 2504 for presenting various test points and associated information, allowing the user to set up or establish test points. The test point set up screen 2502 also includes a number of user selectable test point set up tabs 2506a-2506f (six shown, collectively 2506), which a user may select to determine what type of test point is being set up and hence what type if test point related information is presented in the test point set up screen 2502. For example, the test point set up screen 2502 may include an ATP test point set up tab 2506a, pH test point set up tab 2506b, temperature test point set up tab 2506c, conductivity test point set up tab 2506d, PPM test point set up tab 2506e, and PPM standards test point set up 2506f. A currently selected test point set up tab 2406a (e.g., ATP test points) may be visually indicated or emphasized, for example via highlighting or a color change.

The test point set up chart or table 2504 may, for example, be presented in rows and columns. For instance, each row 2508a-2508n (only two called out) corresponds to a respective test point. The columns may include some of the columns described above in reference to FIG. 24. For example, a test point number column 2510 includes a test point number which identifies the test point. A test point name column 2512 may include a human recognizable test point name that identifies a respective test point. A sampling plan column 2514 may identify a portion of a sampling plan to which the respective test point is associated. Such may include a user selectable expansion/collapse icon 2515 (only one called out) selection of which toggles between expanding and collapsing the respective cell and sampling plan information contained therein. A product identification column 2524 includes a product identifier that identifies a piece of equipment or work surface with which the respective test point is associated. A plant identification column 2526 includes a plant identifier that identifies a plant or other manufacturing or production facility at which the respective test point is located. A note column 2428 includes notes related to the respective test point. A warn column 2530 includes an indication of a warning threshold at which a warning result occurs for the respective test point. A fail column 2532 includes an indication of a failure threshold at which a failure or failing result occurs for the respective test point.

Vertical and horizontal scroll bars 2536a, 2536b allow the user to scroll through the test point set up chart or table 2504.

In addition to a filter menu 2438, the test point set up screen 2502 may include a number of user selectable action icons 2540a-2540d (collectively 2540). For example, selection of a new test point icon 2540a creates a new test point entry in the test point set up chart or table 2504, and in any associated database or other data structure. Selection of an edit test point icon 2540b allows the user to edit information about a test point entry in the test point set up chart or table 2504, and in any associated database or other data structure. Selection of a delete test point icon 2540c deletes a test point entry from the test point set up chart or table 2504, and in any associated database or other data structure. Selection of a new sampling plan icon 2540d creates a sampling plan entry in the test point set up chart or table 2504, and in any associated database or other data structure.

Figure 26:
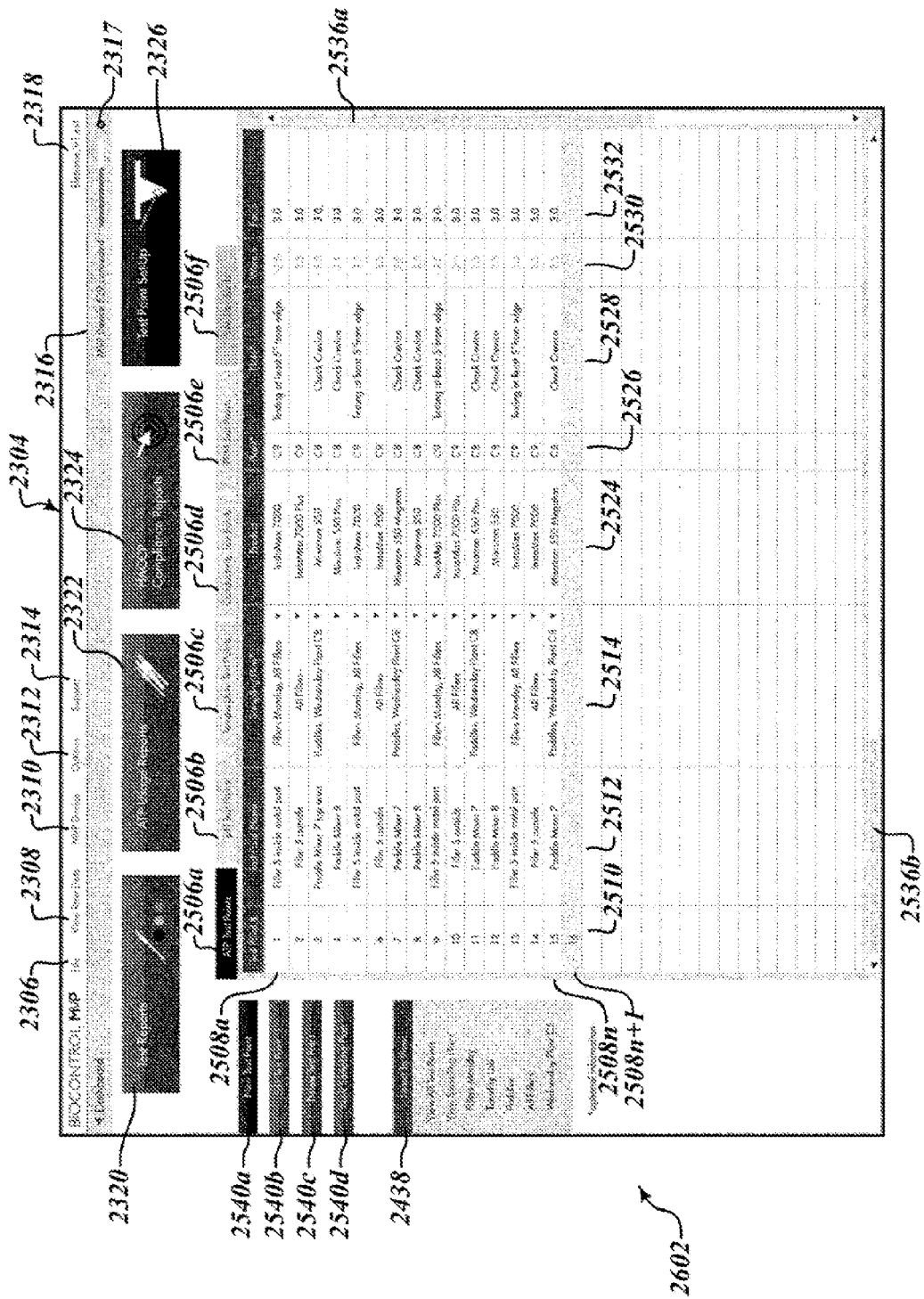
FIG. 26 is a screen print of a new test point set up screen of a user interface according to one illustrated embodiment, which may be presented on a display via a processor of a computer system, communicatively coupled to a portable monitoring instrument such as those described above.

FIG. 26 shows a new test point set up screen 2602 of a user interface according to one illustrated embodiment, which may be presented on a display via a processor of a computer system, communicatively coupled to a portable monitoring instrument such as those described above. The new test point set up screen 2602 has a number of constructs or elements (e.g., user selectable icons, menus, indicators, scroll bars and controls) that are identical or similar to those of the dashboard screen 2302 (FIG. 23) or test point set up screen 2502 (FIG. 25). Similar or identical constructs or elements are identified using the same reference numbers as set out above, and discussion of those elements is not repeated in the interest of brevity. Only significant differences are discussed below.

The new test point set up screen 2602 may be presented in response to selection of the new test point icon 2540*a* (FIG. 25). In response, a new row 2508*n*+1 is set up in the test point set up chart or table 2504, and in any associated database or other data structure. The user may then fill in the information in the various columns 2510, 2512, 2514, 2524, 2526, 2528, 2530, 2532 in the new row 2508*n*+1, which updates the information in any associated database or other data structure.

Figure 27:
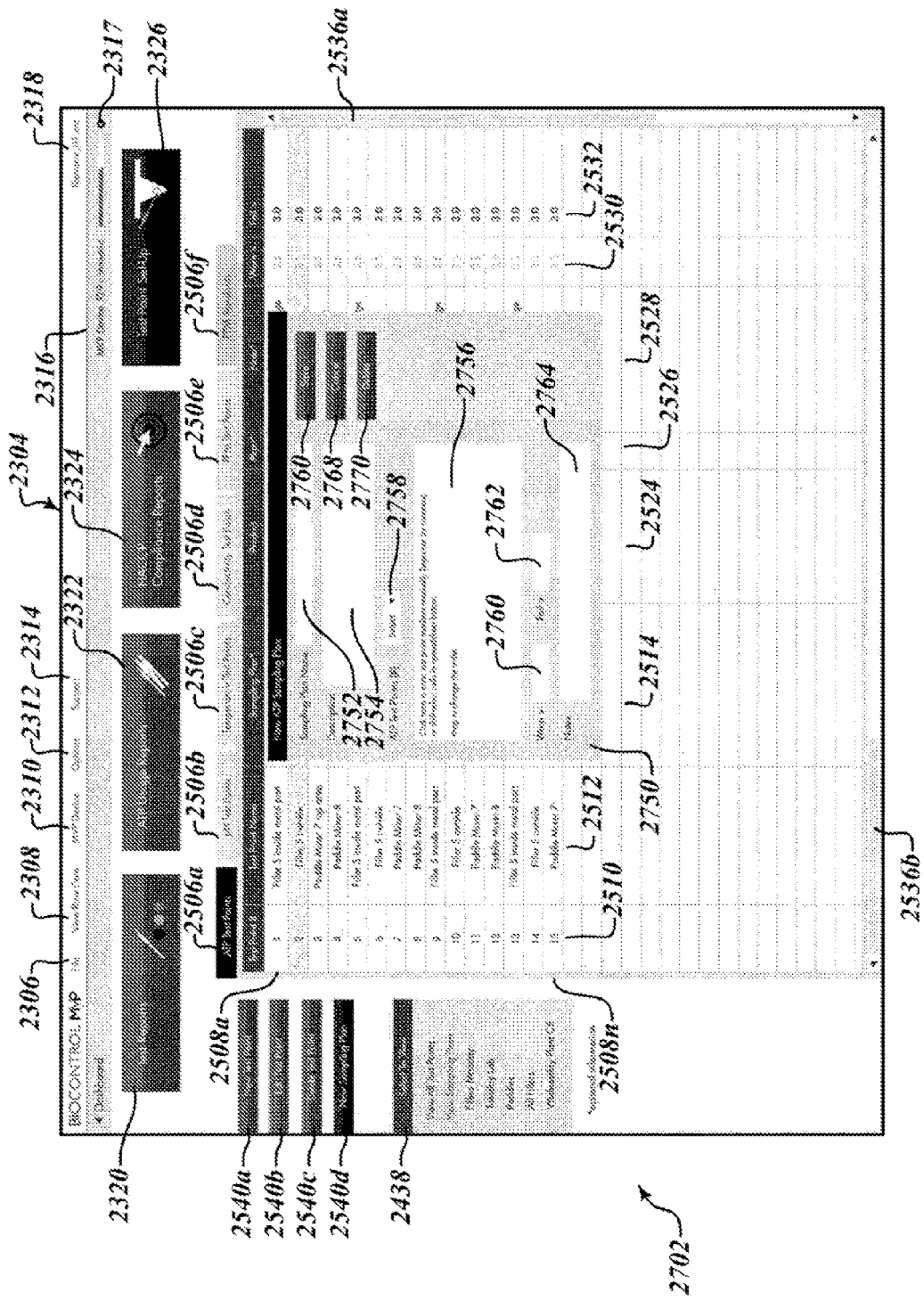
FIG. 27 is a screen print of a new sampling plan set up screen of a user interface according to one illustrated embodiment, which may be presented on a display via a processor of a computer system, communicatively coupled to a portable monitoring instrument such as those described above.

FIG. 27 shows a new sampling plan set up screen 2702 of a user interface according to one illustrated embodiment, which may be presented on a display via a processor of a computer system, communicatively coupled to a portable monitoring instrument such as those described above. The new sampling plan set up screen 2702 has a number of constructs or elements (e.g., user selectable icons, menus, indicators, scroll bars and controls) that are identical or similar to those of the dashboard screen 2302 (FIG. 23) or test point set up screen 2502 (FIG. 25). Similar or identical constructs or elements are identified using the same reference numbers as set out above, and discussion of those elements is not repeated in the interest of brevity. Only significant differences are discussed below.

In response to selection of the new sampling plan icon 2540*d*, a new sampling plan dialog box 2750 is presented, allowing the user to specify a new sampling plan. The new sampling plan dialog box 2750 includes a number of fields. For example, a sampling plan name field 2752 allows the user to enter a name for the new sampling plan. The sampling plan name may be text and/or numeric, and may be human recognizable. The sampling plan name may be entered via keys of a keyboard or keys of a virtual keyboard or keypad. The new sampling plan dialog box 2750 may include a description field 2754 that allows a user to enter a description of the new sampling plan. Again, the description may include alphanumeric characters and may be human understandable. The new sampling plan dialog box 2750 may have a test point entry field 2756 which allows the user to specify tests points for association with the sampling plan. Tests points may be identified by test point number and/or test point name. The test point number or names may be entered manually, via keying or typing, or may be dragged and dropped from a table or chart. The new sampling plan dialog box 2750 may include a selection field, icon or pull down menu 2758 to select the test points, for example allowing selection of all defined test points, or all test points identified in a table or chart. The new sampling plan dialog box 2750 includes warning threshold field 2760 and failing threshold field 2762, allowing the user to specify threshold values which produce warning and failure results, respectively. The new sampling plan dialog box 2750 may further include a notes field 2764, which allows the user to enter notes related to the sampling plan. Notes may be alphanumeric characters and should be human understandable.

The new sampling plan dialog box 2750 includes a number of user selectable action icons. For example, user selection of a save icon 2766 causes the new sampling plan to be saved along with the information specified in the various fields of the new sampling plan dialog box 2750. User selection of a cancel icon 2768 cancels the creation of the new sampling plan without saving changes to any database or other data structure. User selection of a delete icon 2770 deletes an existing sampling plan from a database or other data structure.

Figure 28A:
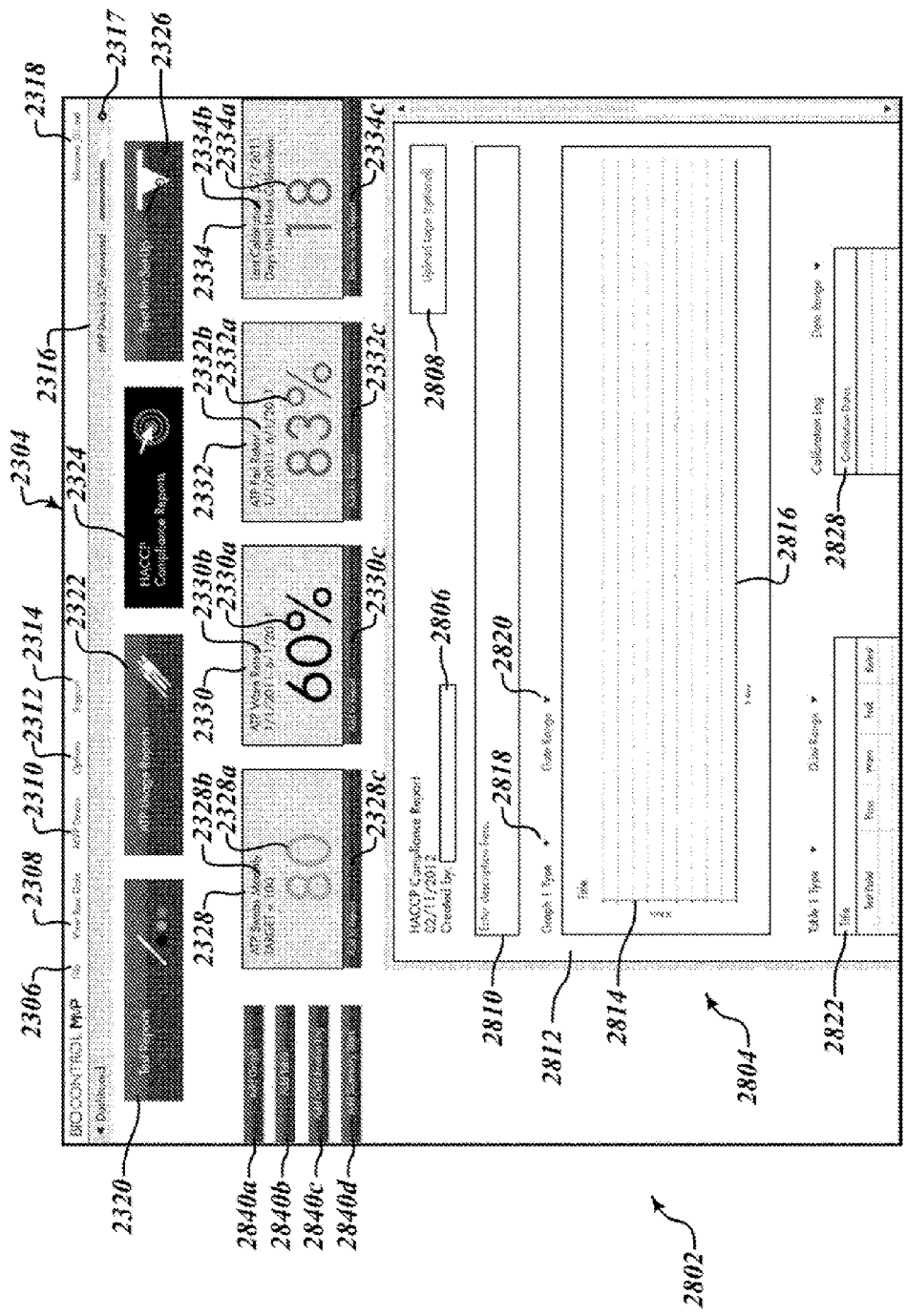
FIGS. 28A and 28B are screen prints of an upper and lower portion of an HACCP report screen of a user interface according to one illustrated embodiment, which may be presented on a display via a processor of a computer system, communicatively coupled to a portable monitoring instrument such as those described above.
Figure 28B:
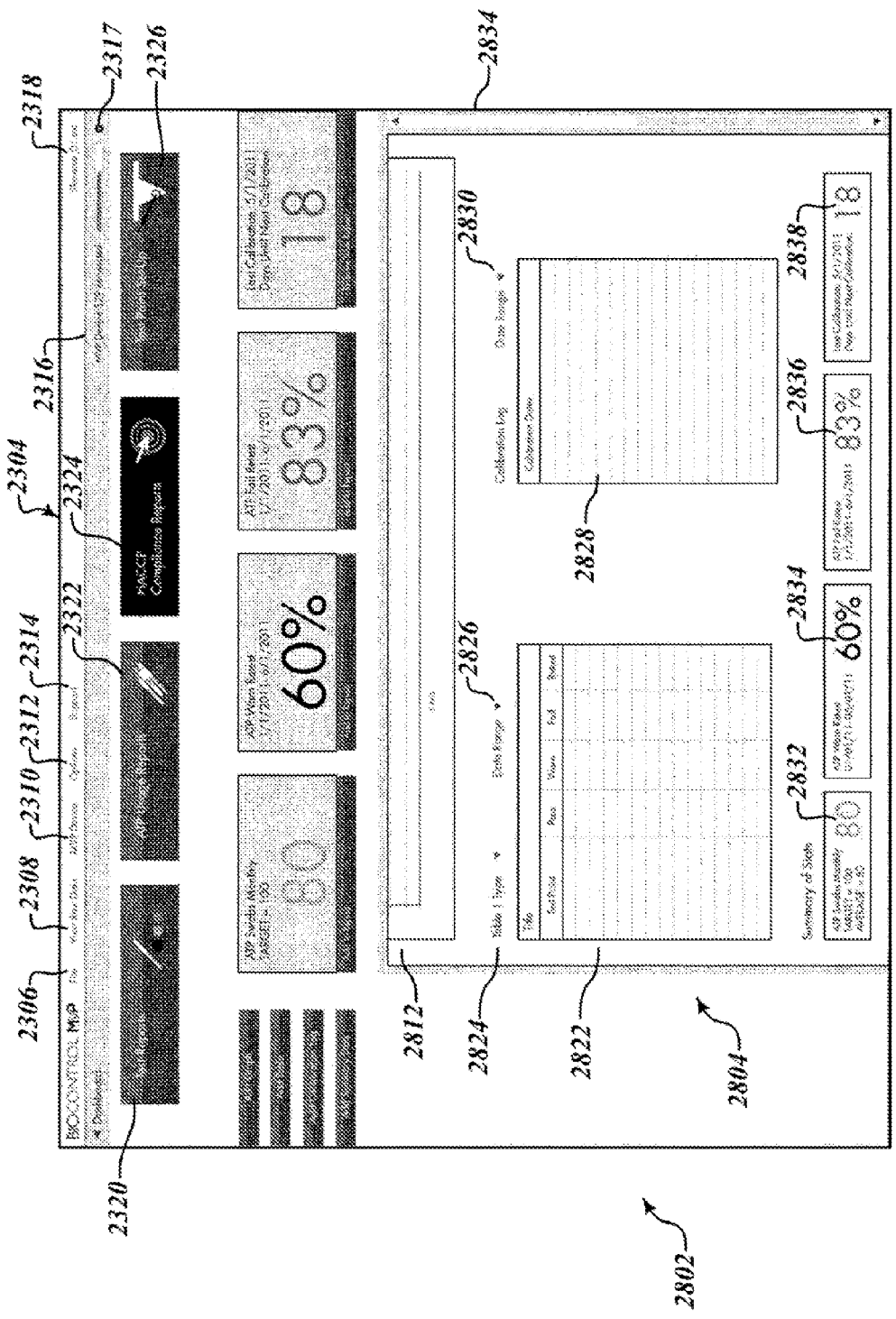

FIG. 28A shows an upper portion and FIG. 28B shows a lower portion of an HACCP report screen 2802 of a user interface according to one illustrated embodiment, which may be presented on a display via a processor of a computer system, communicatively coupled to a portable monitoring instrument such as those described above. The HACCP report screen 2802 has a number of constructs or elements (e.g., user selectable icons, menus, indicators, scroll bars and controls) that are identical or similar to those of the dashboard screen 2302 (FIG. 23). Similar or identical constructs or elements are identified using the same reference numbers as set out above, and discussion of those elements is not repeated in the interest of brevity. Only significant differences are discussed below.

In place of the various charts or tables of the dashboard screen 2302 (FIG. 23), the HACCP report screen 2802 includes an HACCP compliance report 2804. The HACCP compliance report 2804 may include some fixed portions, such as titles, headings, dates, lines, margins, etc., as well as some user-fillable portions and other portions that may be automatically populated with information, for example based on user selections.

For example, the HACCP compliance report 2804 may include a created by field 2806 that allows the user to enter an identifier that specifies the person or entity who creates the compliance report. Such may be a human recognizable name or an identity code. The identifier may be entered via a keyboard or virtual keyboard. A logo field 2808 may allow a user to upload a logo, for example a company logo, to customize the report.

A description field 2810 allows the user to enter a textual description. Such may allow free form text entry including alphanumeric characters. The description may be entered via a keyboard or virtual keyboard.

A graph field 2812 allows the user to include one or more graphs. The graphs may include axes (e.g., vertical axis 2814 and horizontal axis 2816). Selection of a graph type pull down menu icon 2818 expands a graph type pull down menu that allows the user to specify a type of graph from a number of defined graph types. Such determines the type of data to be graphed. Selection of a graph date range pull down menu icon 2820 expands a date range pull down menu that allows the user to specify a range of dates for data that will populate the graph. The graph may be automatically populated based on the user selected graph type and date range using previously collected data or information. In absence of user selection of a graph type, the graph may be omitted from the compliance report 2804.

A table field 2822 allows the user to include one or more tables. The tables may include one or more rows and one or more columns. A table type pull down menu 2824 allows the user to specify a type of table from a number of defined table types. Such determines the type of data to be included in the table. A table date range pull down menu 2826 allows the user to specify a range of dates for data that will populate the table. The table may be automatically populated based on the user selected table type and table date range using previously collected data or information. In absence of user selection of a table type, the table may be omitted from the compliance report 2804.

A calibration log field 2828 allows the user to include one or more calibration log tables. The calibration log tables may include one or more rows of calibration dates, that is, dates on which a portable monitoring instrument was calibrated. A date range pull down menu 2830 allows the user to specify a range of dates for data that will populate the calibration log table. The table may be automatically populated based on the user selected date range using previously collected data or information. In absence of user selection of a date range, the calibration log table may be omitted from the compliance report 2804.

The HACCP compliance report 2804 may include a summary of statistics, represented in the same or similar fashion to that of the dashboard screen 2302. Thus, the summary of statistics may include a tests run report section 2832, a warning results report section 2834, a failure results report section 2836, and a calibration report section 2838. A HACCP report scroll bar 2830 allows the user to scroll through the HACCP report 2804.

The HACCP report screen 2802 may further include user selectable action icons 2840a-2840d (four shown, collectively 2840). For example, selection of an add graph icon 2840a creates or generates a new graph or new graph field in the HACCP report 2804. Selection of an add table icon 2840b creates or generates a new table or new table field in the HACCP report 2804. Selection of an add calibration log icon 2840c creates or generates a new calibration log table or new calibration log table field in the HACCP report 2804. Selection of an add summary statistics icon 2840d creates or generates new summary statistic report sections in the HACCP report 2804.

Figure 28C:
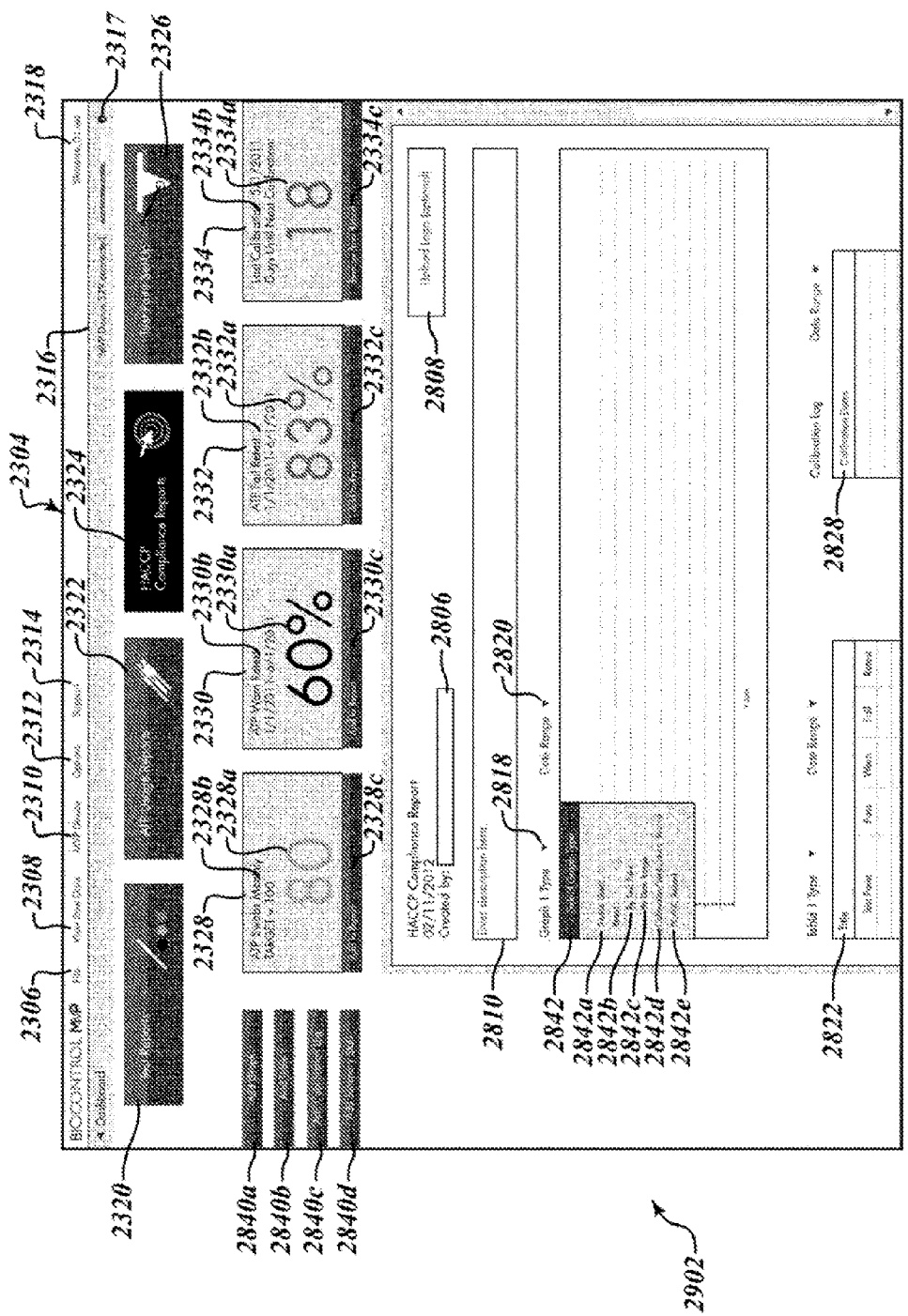
FIG. 28C is a screen print of the upper portion of the HACCP report screen of FIG. 28A with a graph selection element of a user interface according to one illustrated embodiment, which may be presented on a display via a processor of a computer system, communicatively coupled to a portable monitoring instrument such as those described above.

FIG. 28C shows the upper portion of the HACCP report screen 2802 with a graph type pull down menu 2842 expanded, according to one illustrated embodiment. The graph type pull down menu 2842 includes a number of user selectable icons, which identify specific graph types from which the user may select. Graph types icons may, for example, include number of swabs used 2842a, retests performed by test point 2842b, retests performed by date range 2842c, calibration/verification records 2842d, and compliance/partial compliance/non compliance (C/PC/NC) records 2842e. User selection of a graph type, and optionally a date range, may cause automated population of a graph with the appropriate data or information.

Figure 28D:
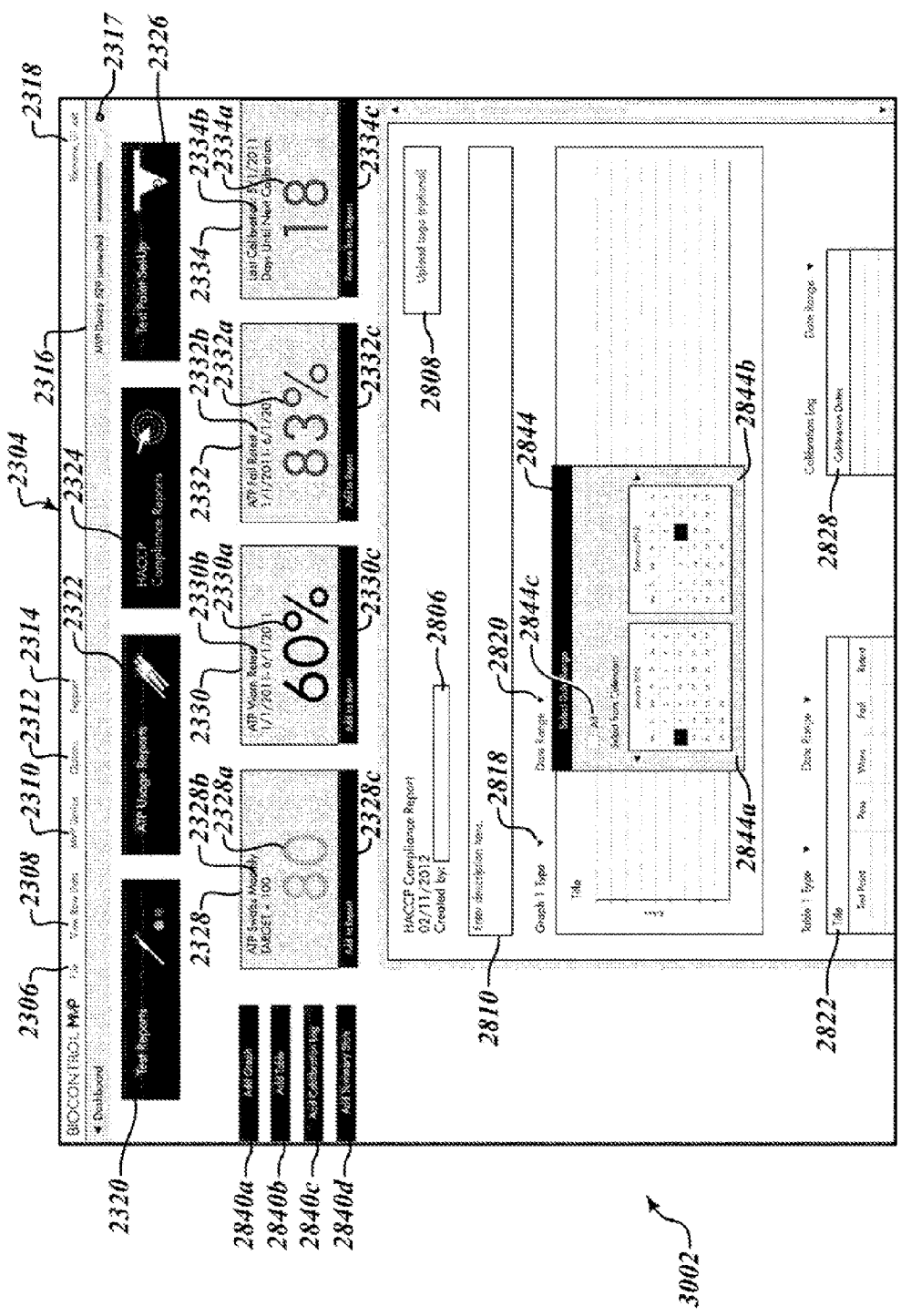
FIG. 28D is a screen print of the upper portion of the HACCP report screen of FIG. 28A with a date range selection element of a user interface according to one illustrated embodiment, which may be presented on a display via a processor of a computer system, communicatively coupled to a portable monitoring instrument such as those described above.

FIG. 28D shows the upper portion of the HACCP report screen 2802 with a date range selection element 2844 expanded, according to one illustrated embodiment. The date range pull down menu 2844 includes a start date calendar 2844a to select a start date and an end date calendar 2844b to select an end date for the range. The date range pull down menu 2844 may include an all dates checkbox 2844c, selection of which selects all available dates for the date range.

Figure 29:
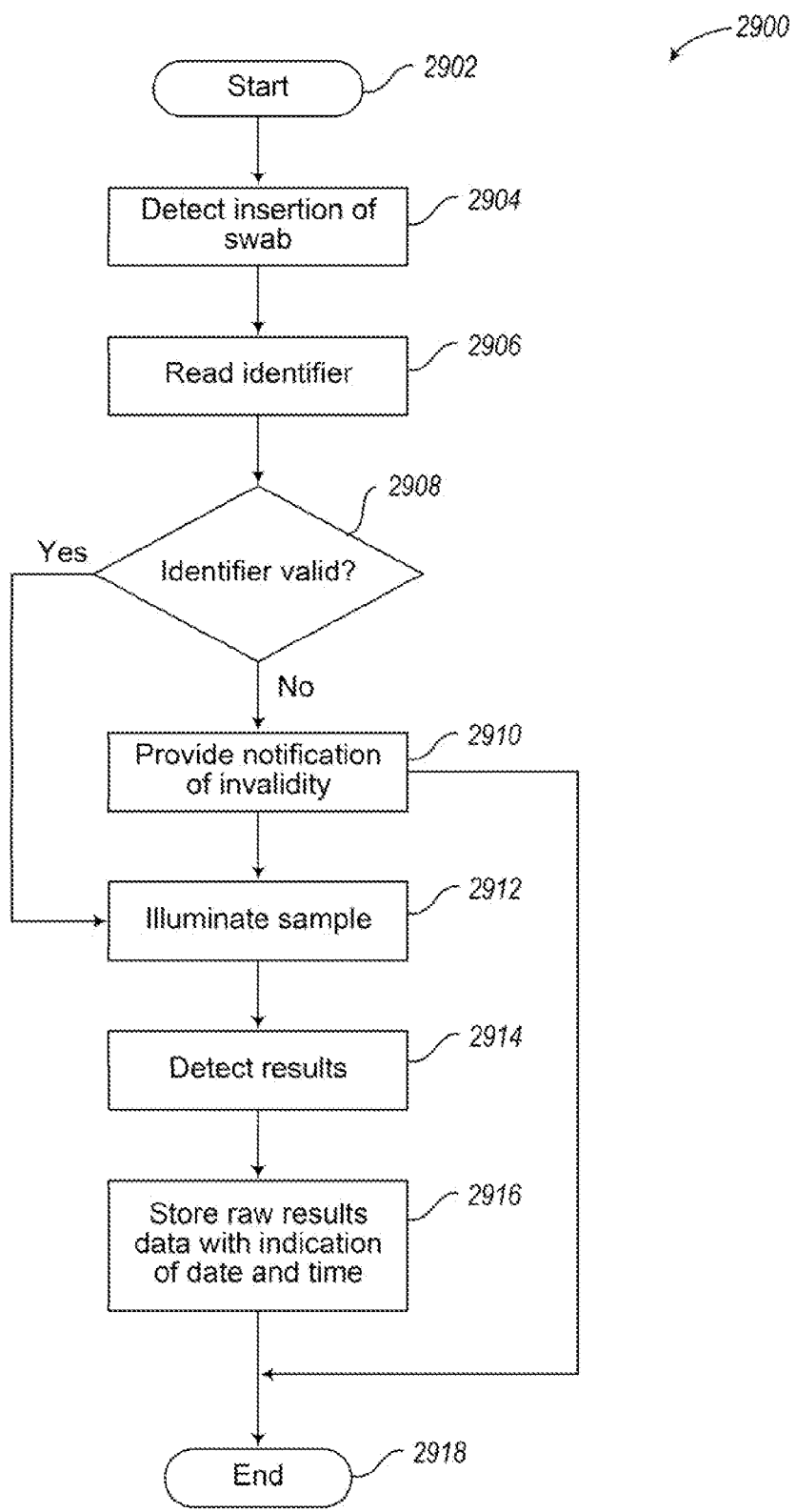
FIG. 29 is a flow diagram of a high level method of operating a portable monitoring instrument to collect data collected, for instance, via swabs, according to one illustrated embodiment.

FIG. 29 shows a high level method 2900 of operating a portable monitoring instrument to collect data collected, for instance, via swabs, according to one illustrated embodiment. At 2902, the method 2900 starts. Such may, for example, be in response to a turning ON or power up of the portable monitoring instrument. At 2904, a sensor detects an insertion of a swab in the portable monitoring instrument. The sensor may, for example, take the form of an optical transmitter/receiver pair, positioned to pass light across a swab receiving passage. Alternatively, the sensor may take the form of a contact switch, or any other device capable of detecting a swab or a position of a cover that selectively controls access to the swab receiving passage.

At 2906, a reader reads an identifier from the swab. The reader may take the form of an imager that captures an image of a portion of the swab. The reader may take the form of a scanner that scans a portion of the swab, for example as the swab moves past a sensor. The reader may take the form of an optical read, including at least one photodetector, for instance a photodiode or an array of charge coupled devices. Where an optical reader is employed, such may include a dedicated illumination source, for instance an incandescent light, florescent light or light emitting diode(s). The reader may, alternatively or additionally, take the form of a magnetic reader, for instance a magnetic stripe reader which may read information encoded in a magnetic stripe carried by the swab. Alternatively or additionally, the reader may take the form of a radio frequency identification (RFID) reader or interrogator, which wirelessly interrogates an RFID tag or transponder carried by the swab. Other forms of readers may be employed.

At 2908, a controller, for instance a microprocessor, determines if the identifier read from the swab is a valid identifier. The controller may compare the read identifier to a stored identifier. If the identifier is not valid, the controller provides notification of invalidity at 2910. Notification may be provided via a user interface of the portable monitoring instrument. At 2912, an illumination source illuminates a sample contained on a portion (e.g., tip) of the swab. At 2914, one or more sensors detect results of the illumination of the sample. For instance, one or more optical sensor may detect an optical response of the sample to the illumination. At 2916, a controller, for instance a microprocessor, stores raw results data with indication of date and time to a non-transitory computer- or processor-readable medium. Such may be stored in a database or other data structure (e.g., record) on the non-transitory computer- or processor-readable medium. At 2918, the method 2900 terminates. The method may terminate until instituted or called again. Alternatively, the method 2900 may continue running as a process in background, until a next swab is detected.

Figure 30:
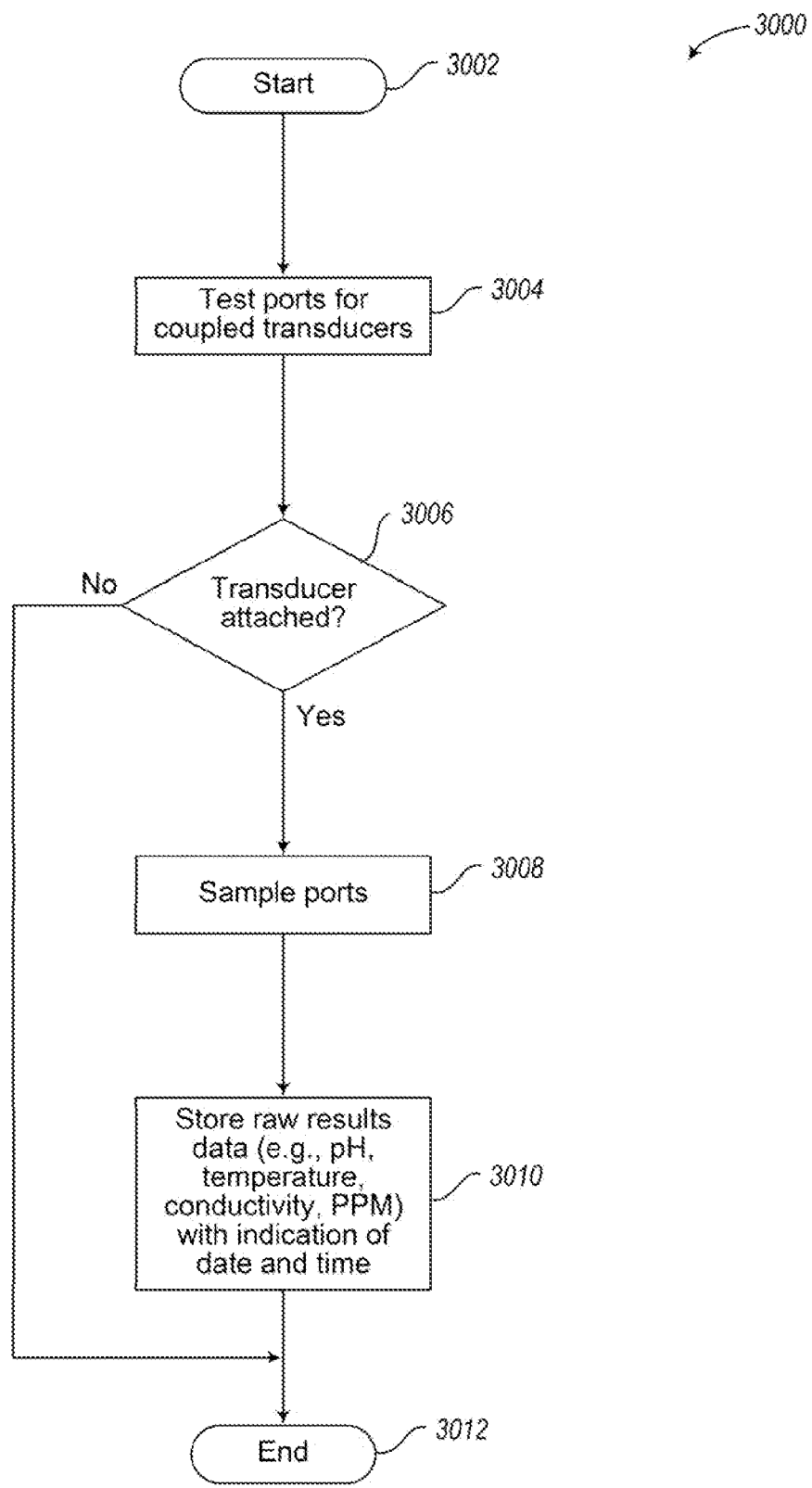
FIG. 30 is a flow diagram of a high level method of operating a portable monitoring instrument to collect data collected, for instance, via external transducers or probes, according to one illustrated embodiment.

FIG. 30 shows a high level method 3000 of operating a portable monitoring instrument to collect data collected, for instance, via external transducers or probes, according to one illustrated embodiment. At 3002, the method 3000 starts. Such may, for example, be in response to a turning ON or power up of the portable monitoring instrument. Such may alternatively be in response to selection of one or more user input elements (e.g., user selectable icons, keys, switches). At 3004, a controller, for instance a microprocessor, test one or more ports for coupled transducers. The controller may test a circuit that detects the presence of a coupled transducer. Presence may, for example, be determined by detecting physical presences, or may be determined by detecting an electrical characteristic such as impedance. Physical presence may be detected via an optical transmitter-receiver pair, physical contact switch or other element.

At 3006, the controller determines whether a transducer or probe is attached at any of the ports. At 3008, the controller samples ports at which a transducer is attached. The sampling collects raw results data measured or otherwise sensed by the respective transducers. The raw results data may be in digital form. Alternatively, a digital-to-analog converter may be employed to convert analog raw results data to a digital form. At 3010, the controller stores raw results data (e.g., pH, temperature, conductivity, ppm) with indication of date and time to a non-transitory computer- or processor-readable medium. Such may be stored in a database or other data structure (e.g., record) on the non-transitory computer- or processor-readable medium. At 3012, the method 3000 terminates. The method may terminate until instituted or called again. Alternatively, the method 3000 may continue running as a process in background.

Figure 31:
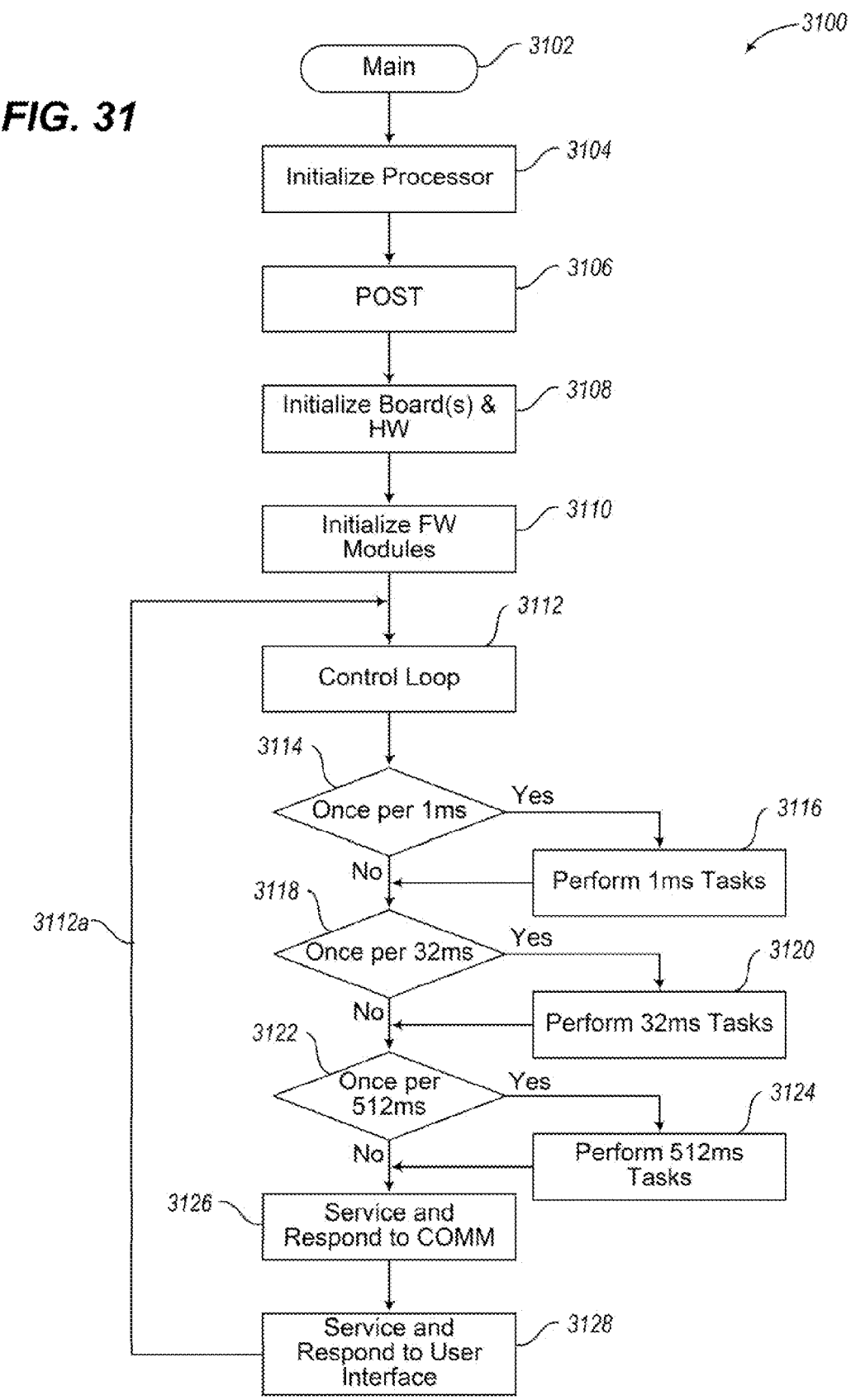
FIG. 31 is a flow diagram of a main method of operating a portable monitoring instrument to collect data collected, for instance, via swabs, according to one illustrated embodiment.

FIG. 31 shows a main method 3100 of operating a portable monitoring instrument to collect data collected, for instance, via swabs, according to one illustrated embodiment.

The main method 3100 starts at 3102. Such may, for example, be in response to a turning ON or power up of the portable monitoring instrument. Upon starting, the main method performs a series of initialization activities. For example, one or more processor(s) may be initialized at 3104. Also for example the processor(s) may execute a series of self tests at 3106. Problems or errors, if any, which are detected during the self tests may be logged and/or reported. Depending on a severity of any detected problem or error, the main method may either continue, or terminate shutting down operation of the portable monitoring instrument. Various components may be initialized at 3108. These components may, for example include various circuit boards, power supplies, analog-to-digital converters (ADCs) and other components. As a further example, various firmware modules may be initialized at 3110. Such may include initializing one or more databases and/or graphics.

After initialization, the main method 3100 enters a primary control loop, as indicated at 3112 and by return branch 3112*a*. The primary control loop is where the portable monitoring instrument performs its primary functions in collecting and analyzing data. The primary control loop includes a number of task subloops which includes the execution or performance of various tasks, each associated with a respective timing cycle at which the task subloop is triggered.

As illustrated, the primary control loop 3112, 3112*a* may include a first task subloop indicated at 3114 and 3116, a second task subloop indicated at 3118 and 3120, and a third task subloop indicated at 3122 and 3124. The first, second and third task subloops may, for instance having timing cycles which repeat every 1 ms, 32 ms and 512 ms, respectively.

During the first task subloop, the processor(s) and/or other components perform a first set of tasks. For example, the processor(s) and/or other components may perform tasks related to taking measurements or capturing data and/or pre-processing or processing the data. Such may include controlling illumination and/or controlling capture of electromagnetic energy returned from a sample or specimen. Such may also include preprocessing or processing measured or captured data, for example normalizing or correlating such, and/or formatting the same. Also for example, the processor(s) and/or other components may perform tasks related to calibration. Such may, for instance, include determining whether one or more sensors are within a sensor calibrated tolerance, determining, whether one or more illuminations sources are within a source calibrated tolerance, and calibrating with respect to the one or more sensors or illumination sources. As a further example, the processor(s) and/or other components may perform tasks related to charging. Charging tasks may include monitoring or determining an external source or type of external source providing power, if any at the given time. For example, electrical power may be supplied via a USB port (e.g., 5V) or via a port for an input from an external power supply. The external power supply may for example be an adapter (e.g., wall adapter) that receives common household current (e.g., AC 120 V, 60 Hz) and steps down the voltage and rectifiers the current (e.g., 12 VDC). Charging tasks may additionally, or alternatively include monitoring or determining a characteristic (e.g., charge level, voltage, number of recharge cycles, age) of an onboard power source. Charging tasks may include ensuring that an onboard power source is being properly charged via a charging circuit (e.g., switch mode power converter and rectifier). Some exemplary tasks suitable for performance as part of the first task subloop are illustrated and discussed below with reference to FIG. 32.

During the second task subloop, the processor(s) or other components may perform probe detection task. Such may, for example, include checking a state or condition of a one or more sensors. Such may additionally or alternatively include verifying an authenticity of a sample or specimen probe, for instance by checking sensed data indicative of a presence of a security indicia or security chip, e.g. radio frequency identification (RFID) or electronic article surveillance (EAS) transponder, carried by authenticate sample or specimen probe. As described herein, the sample or specimen probes may have unique traits or characteristics which improve accuracy or reliability of the measurements. Thus, confirmation assures that results will be reliable.

During the third task subloop, the processor(s) or other components maintain a real time clock. For example, the processor(s) or other components may determine a real world time based on a number of oscillator or system clock cycles that have occurred since a previous time. Such does not require an especially high degree of accuracy so may be performed at the relatively slow rate of once every 512 ms.

Figure 32:
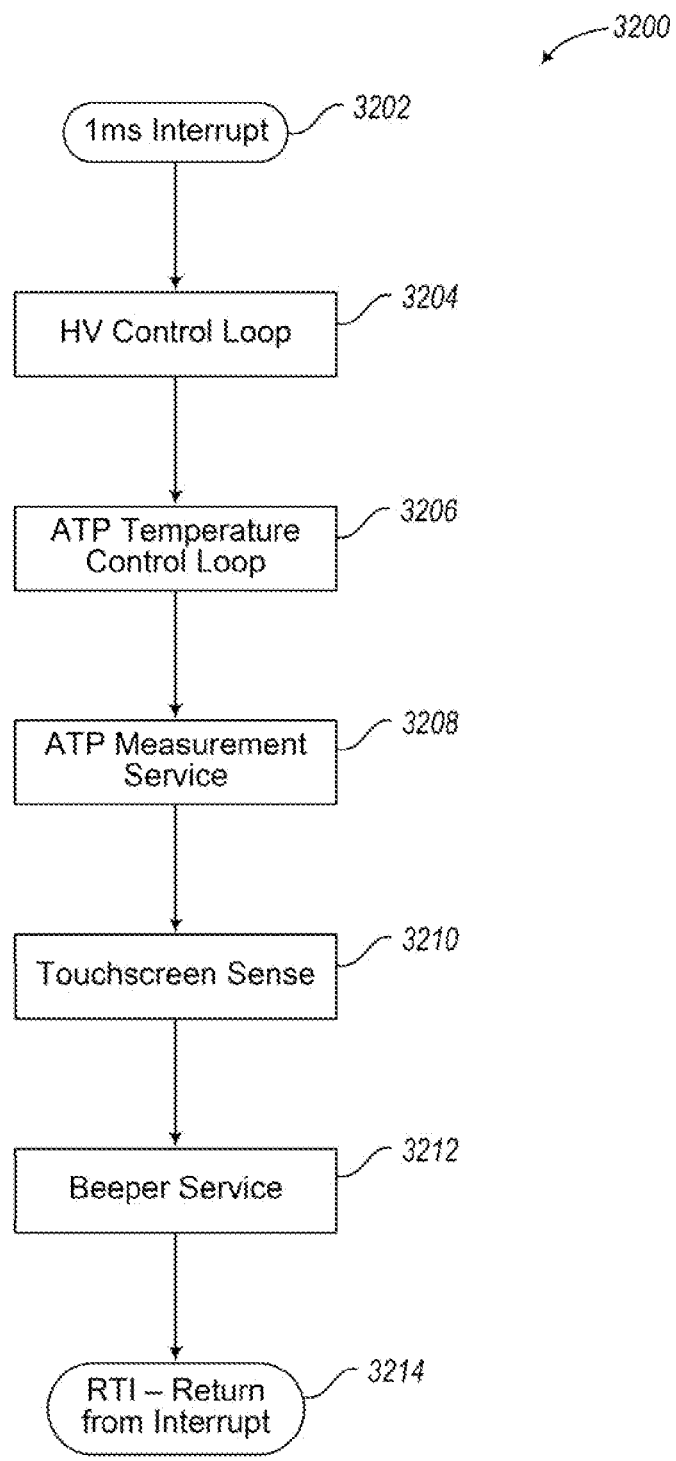
FIG. 32 is flow diagram showing a first task subloop method of operating a portable monitoring instrument to collect data collected, for instance, via swabs, according to one illustrated embodiment.

Many of the tasks of the subloops are further described herein, for example with the methods illustrated in FIG. 32—and described in reference thereto.

Also, as part of execution of the primary control loop 3112, 3112*a*, the processor(s) or other components may perform various tasks related to communications. For example, the processor(s) or other components may receive and/or transmit information, data and/or instructions via one or more communications ports. Such may include wired and/or wireless communications. Communications may employ any communications protocols or standards, for instance Universal Serial Bus® (USB), FireWire®, Thunderbolt®, Ethernet®, IEEE 802.11 protocols and infrastructure.

Also, as part of execution of the primary control loop 3112, 3112*a*, the processor(s) or other components may perform various user interface tasks. For example, the processor(s) or other components may receive user input and/or provide user output via various user interface devices (e.g., touch-sensitive display, trackpad, joystick, thumbstick, keys speakers, LEDs, LCDs, displays, microphones, In particular, the processor(s) or other components may present information to the end user, for instance data, prompts, instructions, user selectable input controls, etc. The processor(s) or other components may poll various user input devices for receipt of user selections, instructions and/or other information.

FIG. 32 shows a first task subloop method 3200 of operating a portable monitoring instrument to collect data collected, for instance, via swabs, according to one illustrated embodiment. As noted above, the first task subloop 3200 may be executed at a relative high frequency or rate (e.g., 1 ms). Thus, the tasks performed as part of the first task subloop 3200 have low latency and low jitter.

The first task subloop method 3200 starts at 3202. Such may, for example, start in response to an interrupt (e.g., a high priority interrupt) or in response to some other call, for instance a call from the main method 3100 (FIG. 31).

At 3204, the processor(s) or other components perform a high voltage control loop method to provide high voltage to other components, for example providing a high voltage to a multi-pixel photon counter (MPPC) within defined voltage range.

At 3206, the processor(s) or other components perform an ATP temperature control loop method. Such may, for example, include adjusting a temperature at least proximate the sample or specimen using active cooling structures.

At 3208, the processor(s) or other components perform an ATP measurement service method. Such may, for example, include illuminating a sample or specimen carried by a swab or probe, and detecting or measuring illumination returned from the sample or specimen.

At 3210, the processor(s) or other components perform a touch screen sense method. Such may, for example, include polling various touch sensitive (e.g., capacitive, resistive, inductive, infrared) sensors that are part of a touch sensitive display device. Such may also include identifying an input or command associated with the activated sensors.

At 3212, the processor(s) or other components perform a beeper service routine. For example, the processor or other components attend to producing any tones, beeps, or other sounds which are indicated by the conditions. For example, the processor(s) or other components may cause a speaker or buzzer to produce an alert.

At 3214, the processor(s) or other components return from the interrupt which triggered the execution of the first task subloop method 3200.

Figure 33:
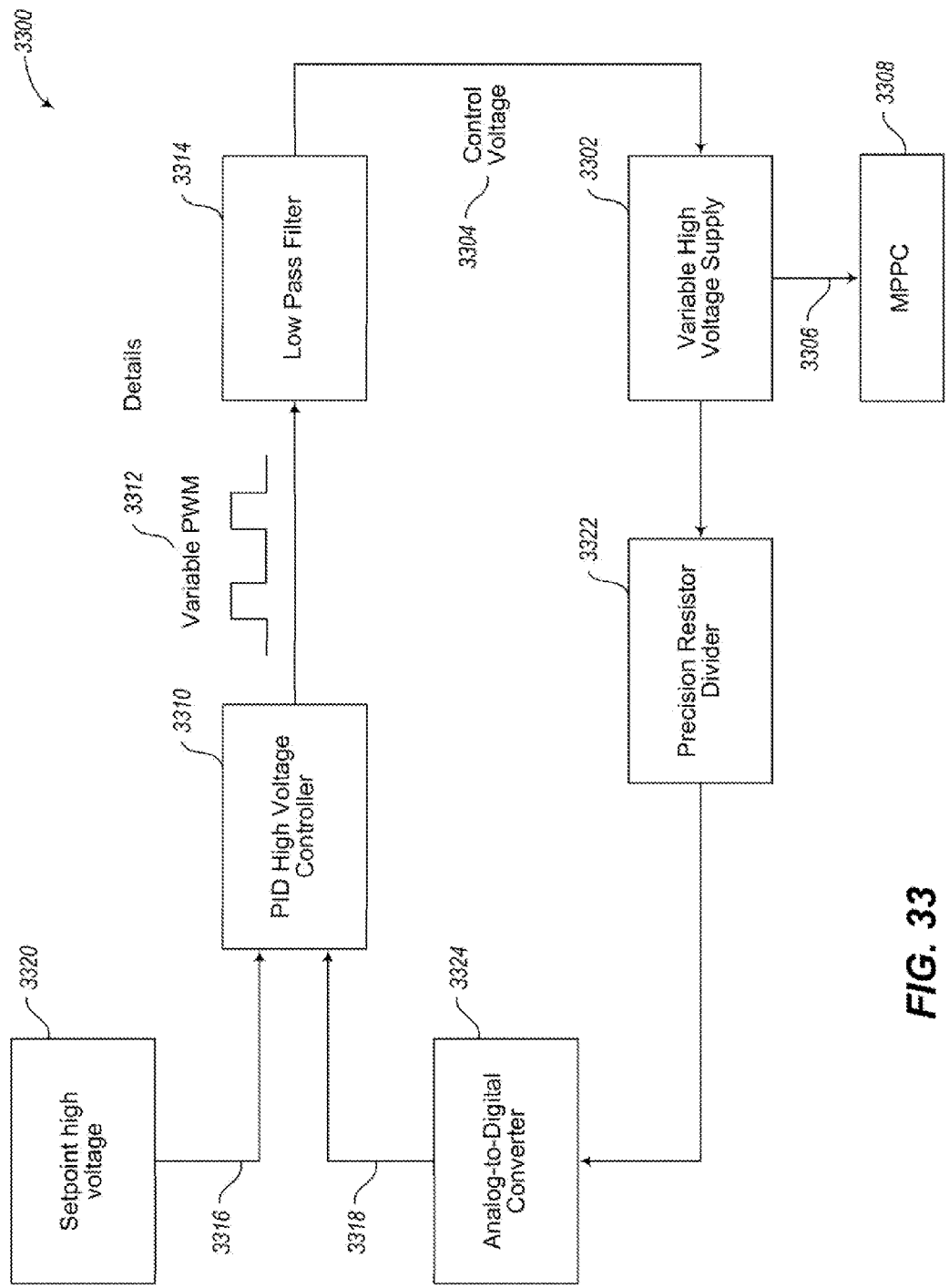
FIG. 33 is a block diagram showing a high voltage controller for controlling a supply of high voltage to components of a portable monitoring instrument, according to one illustrated embodiment.

FIG. 33 shows a high voltage controller 3300 for controlling a supply of high voltage to components of a portable monitoring instrument, according to one illustrated embodiment. The high voltage controller 3300 may execute in response to an interrupt or call from the first task subloop method 3200 (FIG. 32) or may execute in background.

The high voltage controller 3300 includes a variable high voltage supply 3402, which is responsive to a control voltage 3304 to supply high voltage 3306 to one or more components, for instance an MPPC 3308. The control voltage 3304 is generated by a high voltage proportional-integral-derivative (PID) controller 3310, as a variable pulse width modulated (PWM) drive signal 3312, which may be filtered by a low pass filter 3314. The high voltage PID controller 3310 receives two inputs 3316, 3318. A first input 3316 is indicative of a high voltage set point 3320 provided via a voltage source. The second input 3318 is indicative of a value of the high voltage being supplied by the variable high voltage supply 3402. Notably, the second input 33118 does not itself need to be a high voltage, but rather simply represent the magnitude of the high voltage 3306. In particular, the value may be sensed or generated via a precision resistor divider network 3322, and provided to the high voltage PID controller 3310 via an analog-to-digital converter 3324.

Figure 34:
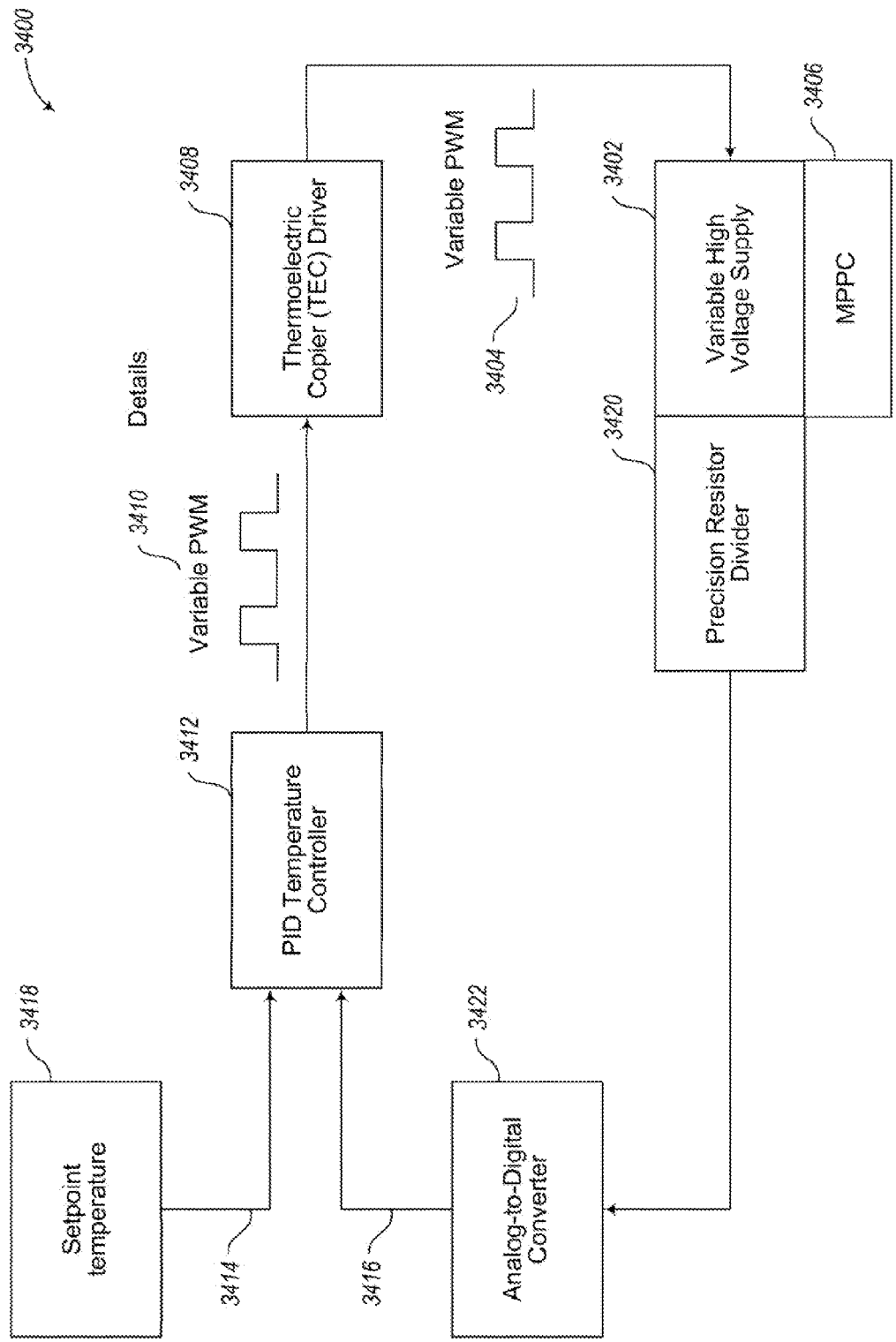
FIG. 34 is a block diagram showing a temperature controller for controlling a temperature of a sensor, for instance a multi-pixel photon counter of a portable monitoring instrument, according to one illustrated embodiment.

FIG. 34 shows a temperature controller 3400 for controlling a temperature of a sensor, for instance an MPPC of a portable monitoring instrument, according to one illustrated embodiment. The temperature controller 3400 may execute in response to an interrupt or call from the first task subloop method 3200 (FIG. 32) or may execute in background.

The temperature controller 3400 includes a thermoelectric cooler 3402 (e.g., Peltier effect cooler), which is responsive to a control signal 3404, for example a PWM control signal, to adjust a temperature (e.g., remove heat) of a sensor, such as an MPPC 3406. The control signal 3304 is generated by thermoelectric cooler driver 3408. The thermoelectric cooler driver 3408 is responsive to a variable PWM signal 3410 generated by a high voltage PID controller 3412. The high voltage PID controller 3412 receives two inputs 3414, 3416. A first input 3414 is indicative of a temperature set point 3418. The second input 3318 is indicative of a temperature of, or a temperature at least proximate, the MPPC 3406 as measured, detected or otherwise sensed by a temperature sensor 3420. Value indicative of temperature may be provided to the temperature PID controller 3412 via an analog-to-digital converter 3422.

Figure 35:
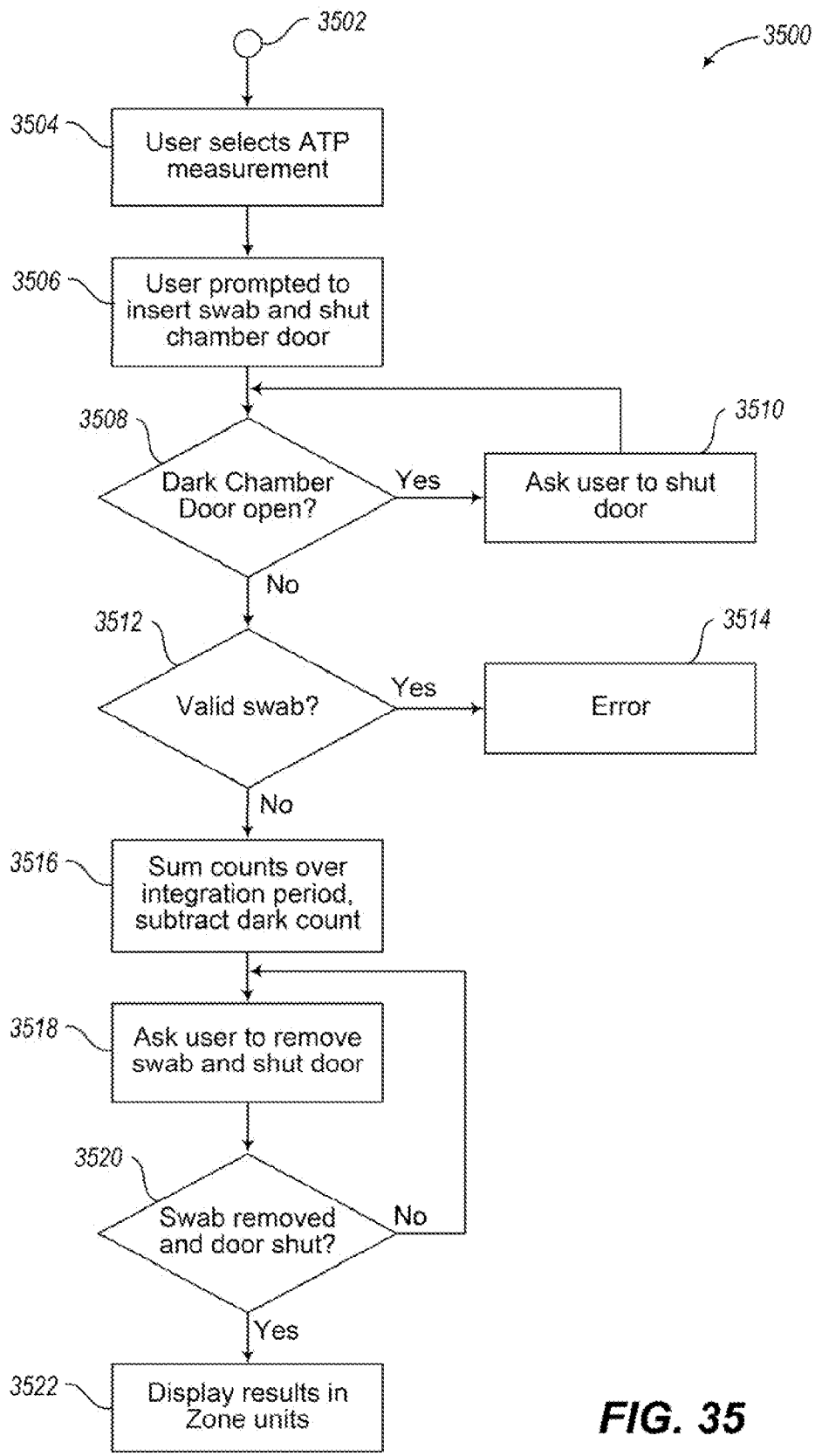
FIG. 35 is a flow diagram showing an ATP measurement method for use in operation of a portable monitoring instrument to collect data from samples, for example carried by swabs, according to one illustrated embodiment.

FIG. 35 shows an ATP measurement method 3500 for use in operation of a portable monitoring instrument to collect data from samples, for example carried by swabs, according to one illustrated embodiment.

The ATP measurement method 3500 starts at 3502. Such may, for example, start in response to an interrupt or call, for example a call from the first task subloop method 3200 (FIG. 32).

At 3504, a processor(s) or other component of the instrument detects a user input indicative of a selection to perform ATP measurements. The processor(s) or other component may, for example, detect a user selection of a measure ATP user selectable icon displayed as part of a GUI. Alternatively, the processor(s) or other component may detect user selection of one or more keys, buttons or switches, or a spoken command.

At 3506, the processor(s) or other component prompts the user to insert a swab and close a door that provides access to a dark chamber of the instrument. The processor(s) or other component may cause a prompt to be displayed via a GUI, for example by displaying an appropriate message or dialog box. Additionally, or alternatively, the processor(s) or other component may cause the prompt to be provided as an audible message via a speaker of the instrument.

At 3508, the processor(s) or other component determines whether the door to the dark chamber door is open. The door not only selective provides access to an interior of the dark chamber, but also is used to prevent or limit the ingress of light into the interior of the dark chamber from exterior sources. Such facilitates accurate readings.

If the processor(s) or other component determines that the door is sensed or detected as being in an open condition or state, the processor(s) or other component prompts the user to close the door at 3510, and returns control to 3508. The processor(s) or other component may cause the prompt to be displayed via a GUI, for example by displaying an appropriate message or dialog box. Additionally, or alternatively, the processor(s) or other component may cause the prompt to be provided as an audible message via a speaker of the instrument. This may essentially institute a lock-out mechanism, the loop preventing the instrument from performing ATP measurements until the condition is satisfied, hence ensuring the reliability of sensed and/or recorded or reported data. Conversely, if the processor(s) or other component determines that the door is sensed or detected as being in a closed condition or state, control passes to 3512 without providing the prompt at 3510.

At 3512, the processor(s) or other component attempts to validate a swab that was inserted. The processor(s) or other component determines whether the swab that was inserted is valid or authenticate. Such may include reading one or more security indicia carried by the swab.

The security indicia may take a variety of forms. For example, the security indicia may be one or more optically readable machine-readable symbols printed on, etched in, embossed, debossed or otherwise inscribed or applied to a portion of the swab. The optically readable machine-readable symbols may be encoded or constitute part of one or more human-readable symbols. For instance, a flat portion of a probe may carry a trademark or trade name, which is human-readable. A portion of the trademark or trade name encode or constitute the machine-readable, which may not be human-readable. Thus, leading and/or trailing edges of letters or other elements of the trade name or trademark as viewed with respect to a straight scanning line passing there across, may constitute a type of machine-readable symbol (e.g., linear barcode) Alternatively, a two dimensional area or matrix code symbol may be employed. In some embodiments, the machine-readable symbol may not be visible to humans, for example being optically detectable only in the ultraviolet or infrared portions of the electromagnetic spectrum.

The security indicia may take an non-optical form. For example, the security indicia may additionally or alternatively include one or more wireless transponders carried by the swab. The wireless transponders may take a variety of forms, for example radio frequency identification (RFID) transponders which store or otherwise encode a unique identifier. If employed, the RFID transponders will likely take the form of passive RFID transponders, not having a discrete power source (e.g., chemical battery cells). Detection of RFID transponders typically include the reading of the unique identifier from an RFID transponder in an interrogation field produced by a radio or interrogator, which may from part of the instrument. The unique identifier may be wirelessly transmitted or returned to the radio or interrogator in an encrypted form to further enhance security.

Alternatively or additionally, the wireless transponder may take the form of an electronic surveillance article (EAS) transponder. EAS transponders typically do not store or encode unique identifiers. Detection of EAS transponders typically is a simple detection of a presence or absence of an EAS transponder in an interrogation field produced by a radio or interrogator.

If the processor(s) or other component cannot validate or authenticate the swab, processor(s) or other component perform an error routine at 3514. If the swab is validated, control passes directly to 3516, without performing the error routine 3514. Performance of the error routine may include performing one or more actions. For example, the processor(s) or other component may log the attempt to use an invalid or authenticated swab in a log maintained on nontransitory computer- or processor-readable media. Also for example, the processor(s) or other component may generate an alert. Generation of the alert may include providing the alert to an end user via the UI of the instrument. For example, an appropriate visual alert message or dialog box may presented via a display of the instrument, an indicator (e.g., red LED) may be illuminated, and/or an appropriate provided an appropriate audible alert message may be presented via a speaker of the instrument. Additionally or alternatively, generation of the alert may include causing the alert to be provided to remote individuals or systems remotely located from the instrument. For example, the processor(s) or other component may cause an appropriate alert message to be wirelessly and/or wiredly transmitted from the instrument via a transmitter, port, or radio.

At 3516, the processor(s) or other component performs the ATP measurement. For example, the processor(s) or other component may sample the sensor, summing counts over an integration period, and subtracting dark counts from the sum(s).

At 3518, the processor(s) or other component prompts the end user to remove the swab and close the door to the dark chamber. The processor(s) or other component may cause the prompt to be displayed via a GUI, for example by displaying an appropriate message or dialog box. Additionally, or alternatively, the processor(s) or other component may cause the prompt to be provided as an audible message via a speaker of the instrument. At 3520, the processor(s) or other component determines whether the swab has been removed and door closed. The processor(s) or other component may query one or more sensors that detect: 1) whether a swab is present, and 2) a position or condition of a door. If either the swab has not been removed or if the door is not closed, control returns to 3518, where the processor(s) or other component again prompts the end user to remove the swab and/or close the door.

Once the swab has been removed and the door closed, the processor(s) or other component provides results. The processor(s) or other component may provide the results to an end user via the UI devices or elements. For example, the processor(s) or other component may cause results to be displayed via a display of the instruments. Additionally, or alternative, the processor(s) or other component may cause results to be presented aurally, via a speaker of the instrument. Additionally or alternatively, the processor(s) or other component may provide the results to remote individuals or systems remotely located from the instrument. For example, the processor(s) or other component may cause an appropriate results message to be wirelessly and/or wiredly transmitted from the instrument via a transmitter, port, or radio. Results may be presented in any of a variety of formats, for example in zone units.

Figure 36:
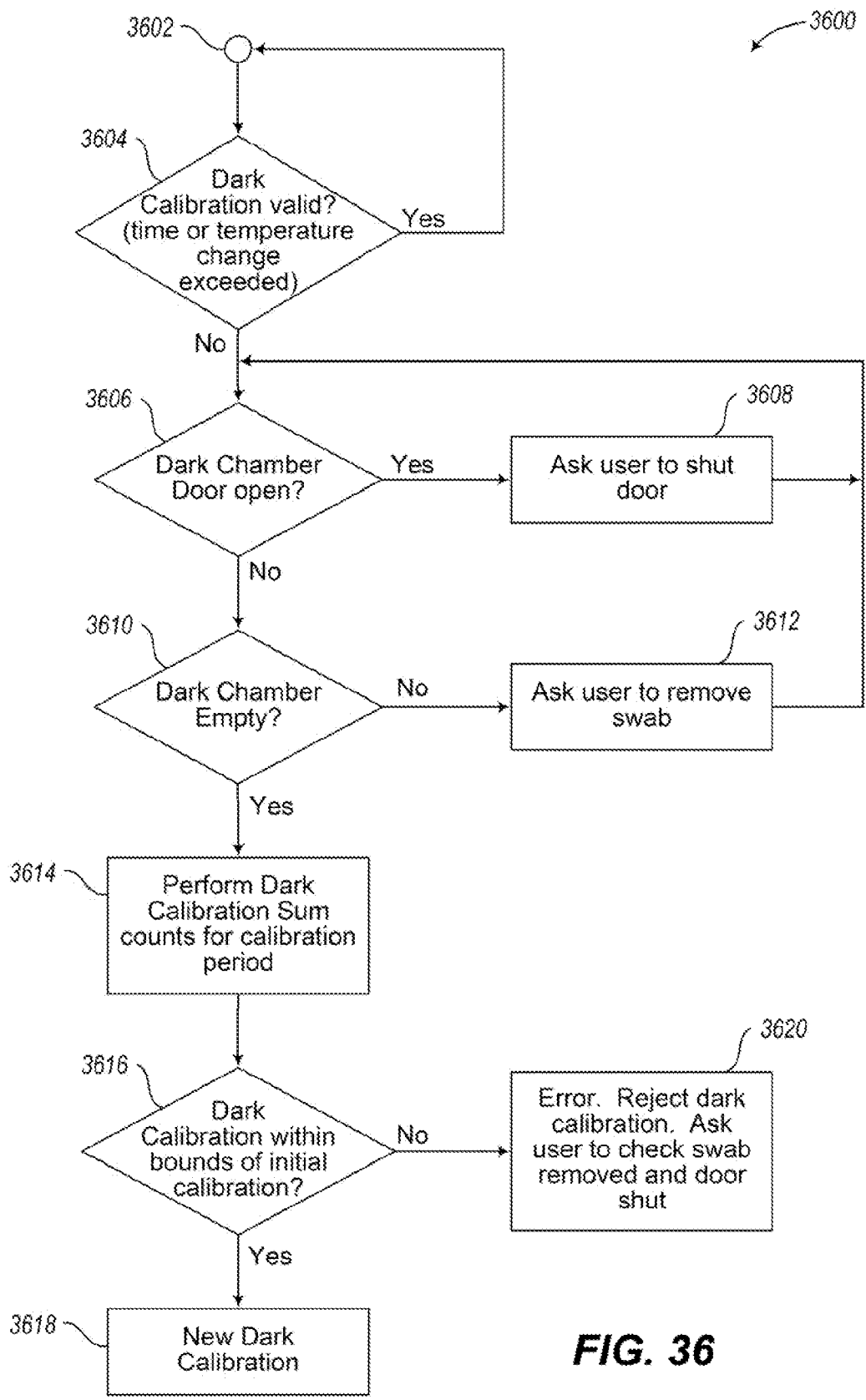
FIG. 36 is a flow diagram showing a dark count calibration method for use in operation of a portable monitoring instrument to collect data from samples, for example carried by swabs, according to one illustrated embodiment.

FIG. 36 shows a dark count calibration method 3600 for use in operation of a portable monitoring instrument to collect data from samples, for example carried by swabs, according to one illustrated embodiment. Many sensors, for instance MPPC sensors produce thermally-generated background counts, which occur even in the dark. These may be denominated as "dark counts." Calibrating for such dark counts improves the accuracy of results when later testing or analyzing a sample or specimen.

The dark count calibration method 3600 starts at 3602. Such may, for example, start in response to an interrupt or call, for example a call from the first task subloop method 3200 (FIG. 32).

At 3604, the processor(s) or other component of the instrument determines whether a current dark count calibration is valid. For example, the processor(s) or other component may determine whether a period of time has been exceeded. For instance, the processor(s) or other component may determine whether a period of time since a most recent calibration has exceeded a defined time threshold. The defined time threshold may be empirically set based on observations of how long it typically takes an instrument to fall out of calibration. The defined time threshold may be set to include a suitable margin of error, for example based on statistical evaluation of the empirical results. Additionally or alternatively the processor(s) or other component may determine whether a temperature of the instrument, a portion of the instrument and/or in an ambient environment at least proximate the instrument is outside a defined temperature threshold range. The defined temperature threshold range may be empirically set based on observations of the affect of temperature variation of the instrument or portions thereof (e.g., MCCP, illumination sources such as LEDs which are temperature sensitive). The defined temperature threshold range may be set to include a suitable margin of error, for example based on statistical evaluation of the empirical results.

If the processor(s) or other component determines that the current dark count calibration is valid, control returns to 3604, implementing a wait loop. If the processor(s) or other component determines that the current dark count calibration is not valid, control passes to 3606.

At 3604, the processor(s) or other component of the instrument determines whether the door to the dark chamber door is open. The door not only selective provides access to an interior of the dark chamber, but also is used to prevent or limit the ingress of light into the interior of the dark chamber from exterior sources. Such facilitates accurate readings. The processor(s) or other component may check a state or condition of a sensor positioned or otherwise responsive to a position, condition or state of the door.

If the processor(s) or other component determines that the door is sensed or detected as being in an open condition or state, the processor(s) or other component prompts the user to close the door at 3608, and returns control to 3606. The processor(s) or other component may cause the prompt to be displayed via a GUI, for example by displaying an appropriate message or dialog box. Additionally, or alternatively, the processor(s) or other component may cause the prompt to be provided as an audible message via a speaker of the instrument. This may essentially institute a lock-out mechanism, the loop preventing the instrument from performing the dark count validation until the condition is satisfied, hence ensuring the reliability of sensed and/or recorded or reported data. Conversely, if the processor(s) or other component determines that the door is sensed or detected as being in a closed condition or state, control passes to 3610 without providing the prompt at 3608.

At 3614 the processor(s) or other component of the instrument determines whether the dark chamber is empty. The presence of a swab and/or probe will adversely affect the ability to perform accurate calibration. The processor(s) or other component may check a state or condition of a sensor positioned or otherwise responsive to a presence or absence of a swab or probe.

If the processor(s) or other component determines that the dark chamber is not empty, the processor(s) or other component prompts the user to empty the dark chamber at 3612, and returns control to 3606. The processor(s) or other component may cause the prompt to be displayed via a GUI, for example by displaying an appropriate message or dialog box. Additionally, or alternatively, the processor(s) or other component may cause the prompt to be provided as an audible message via a speaker of the instrument. This may essentially institute a lock-out mechanism, the loop preventing the instrument from performing the dark count calibration until the condition is satisfied, hence ensuring the reliability of sensed and/or recorded or reported data. Conversely, if the processor(s) or other component determines at 3610 that the dark chamber is empty, control passes to 3614 without providing the prompt at 3612.

At 3614, the processor(s) or other component samples the sensor and determines a dark chamber calibration value, summing counts over a calibration period. Since the dark chamber is empty, the counts represent measurements of background illumination in the dark chamber, unrelated to any samples or specimens.

At 3616, the processor(s) or other component determines whether the determined dark chamber calibration value is within defined bounds or threshold of an initial dark chamber calibration value. If the dark chamber calibration value is within defined bounds or threshold of the initial dark chamber calibration value, at 3618 the processor(s) or other component accepts (i.e., sets) the new dark chamber calibration value as the value for dark chamber calibration in performing ATP measurements. Conversely, if the determined dark chamber calibration value is not within defined bounds or threshold of the initial, the processor(s) or other component executes an error routine at 3620.

The error routine 3620 may include one or more acts. For example, the processor(s) or other component may reject (i.e., not set or employ) the new dark chamber calibration value. Additionally, the processor(s) or other component may prompt the end user to at least one of check that the dark chamber is empty (e.g., swab and/or probe removed) or that the door to the dark chamber is closed. The processor(s) or other component may cause the prompt to be displayed via a GUI, for example by displaying an appropriate message or dialog box. Additionally, or alternatively, the processor(s) or other component may cause the prompt to be provided as an audible message via a speaker of the instrument.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet, including but not limited to U.S. patent application Ser. No. 12/135,934; filed Jun. 9, 2008; U.S. patent application Ser. No. 11/354,413, filed Feb. 14, 2006; U.S. patent application Ser. No. 10/313,941, filed Dec. 5, 2002; and U.S. patent application Ser. No. 60/338,844, filed Dec. 6, 2001 are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A portable monitoring system, comprising:
    a housing sized to be manually held by a human, the housing having a passage sized to removably receive at least one sample holder, the passage including at least one opening at least proximate a portion of the passage that provides access into the passage from an exterior of the housing;
    a dark chamber having an inner surface that at least partially encloses an interior of the dark chamber, at least a portion of the inner surface optically reflective and spherical with an associated focal point, the dark chamber located at a distal portion of the passage with respect to the at least one opening, the passage oriented relative to the dark chamber to position a distal portion of the sample holder to pass through the focal point of the optically reflective and spherical portion of the inner surface when the sample holder is removably received in the passage;

at least one photo-responsive sensor exposed to the interior of the dark chamber;

at least one processor communicatively coupled to the at least one photo-responsive sensor; and at least one display communicatively coupled to the at least one processor.

2. The portable monitoring system of claim 1, further comprising the at least one sample holder, wherein the distal portion the sample holder is transparent to at least some wavelengths of light and in use holds a liquid, and the passage positions the distal portion of the sample holder with a portion of the liquid coincident with the focal point of the optically reflective and spherical portion of the inner surface when the sample holder is removably received in the passage, and the transparent distal portion and the liquid form a cylindrical lens that has a foci coincident with the at least one photo-responsive sensor.

3. The portable monitoring system of claim 2 wherein the transparent distal portion of the sample holder is spaced from the at least one photo-responsive sensor by a distance that at least approximately matches a focal length of the cylindrical lens formed by the transparent distal portion and the liquid retained therein.

4. The portable monitoring system of claim 2 wherein the liquid includes reagent and sample leached from a test swab received by the sample holder.

5. The portable monitoring system of claim 1 wherein the at least one photo-responsive sensor is a multi-pixel photon counter in the form of an array of avalanche photodiodes.

6. The portable monitoring system of claim 1 wherein over half of the inner surface of the dark chamber is reflective and spherical.

7. The portable monitoring system of claim 1 wherein the dark chamber comprises a first unitary portion and a second unitary portion, the second unitary portion physically coupled to the first unitary portion.

8. The portable monitoring system of claim 1 wherein the inner surface of the dark chamber carries a reflective layer.

9. The portable monitoring system of claim 1 wherein the reflective layer is a metallic coating.

10. The portable monitoring system of claim 9 wherein the inner surface of the dark chamber carries protective oxide layer that overlies and is spaced inwardly of the metallic layer.

11. The portable monitoring system of claim 1 wherein the chamber includes first opening at which the passage is coupled to the chamber, and a second opening proximate which the at least one photo detector is optically coupled to the interior of the chamber.

12. The portable monitoring system of claim 11 wherein the second opening is substantially perpendicular to the first opening.

13. The portable monitoring system of claim 1, further comprising:

a mechanical security mechanism that includes an irregular surface that has a non-circular inner profile that is complementary to a non-circular outer profile of a portion of the sample holder to be received in the passage.

14. The portable monitoring system of claim 13 wherein the mechanical security mechanism is part of the passage or at least proximate the opening of the passage.

15. The portable monitoring system of claim 13 wherein the inner non-circular profile is a D-shaped profile.

16. The portable monitoring system of claim 1 wherein each sample holder has an elongated stem having a flat portion, and wherein the portable monitoring system further comprises:

a machine-readable symbol reader positioned to read at least a portion of a machine-readable symbol on the flat portion of the elongated stem of the test swab when the sample holder is received at least partially in the passage, the machine-readable symbol reader communicatively coupled to the at least one processor.

17. The portable monitoring system of claim 16 wherein the machine-readable symbol is embossed on the elongated stem of the test swab and the machine-readable symbol reader includes at least one of an imager machine-readable symbol engine or a scanner machine-readable symbol engine.

18. The portable monitoring system of claim 16 wherein the at least one processor determines whether the machine-readable symbol reader reads at least one machine-readable symbol encoding valid authentication information, wherein the at least one processor obtains test results via the at least one photo-responsive sensor, and wherein the at least one processor provides test results only for sample holders that include a respective machine-readable symbol encoding valid authentication information.

19. The portable monitoring system of claim 1 wherein the at least one display is operable to present output indicative of a level of biological contamination present on a test swab inserted into the sample holder.

20. The portable monitoring system of claim 19 further comprising a keypad communicatively coupled to the at least one processor.

21. The portable monitoring system of claim 19 wherein the at least one processor determines the level of biological contamination responsive to at least one output of the at least one photo-responsive sensor, wherein the at least one processor compares the level of biological contamination to at least one of a first value or a second value, and wherein at least a portion of the display displays a first color responsive to at least one indication by the at least one processor that the level of biological contamination is less than the first value;

wherein at least a portion of the display displays a second color responsive to at least one indication by the at least one processor that the level of biological contamination is greater than the second value; and wherein at least a portion of the display displays a third color responsive to at least one indication by the at least one processor that the level of biological contamination is greater than or equal to the first value and less than or equal to the second value.

22. The portable monitoring system of claim 1, further comprising the sample holder in the form of a probe assembly sized for insertion into the passage and the dark chamber, and which includes a fluid conduit passing through at least a first cylindrical portion and terminating in an optically transparent chamber at the distal portion at a distal end of the first cylindrical portion, a portion of the fluid conduit sized to accept the passage of a test swab which includes at least a shaft member and a swab tip.

23. The portable monitoring system of claim 22 wherein the probe assembly carries at least one authentication element detectable by the at least one scanning device, and wherein the portable monitoring system further comprises:

at least one scanning device including at least one of: an electronic scanning device, an optical scanning device, and an infrared scanning device, wherein at least one component of the portable monitoring system authenticates the probe assembly based at least in part on the detection of the at least one authentication element.

24. The portable monitoring system of claim 23 wherein at least a portion of an exterior of the first cylindrical section includes a D-shaped portion comprising a flat portion and a radiused portion, the at least one authentication element on the flat portion of the exterior of the first cylindrical section, the at least one authentication element selected from the group consisting of: a wireless transponder, a machine readable symbol, a debossed trademark, a debossed trade name, a printed trademark and a printed trade name.

25. The portable monitoring system of claim 1, further comprising at least one communications port communicably coupled to the at least one processor, the communications port to accept the communicable coupling of at least one external sensor.

26. The portable monitoring system of claim 25 wherein the at least one external sensor includes at least one of: a pH sensor, a dissolved oxygen sensor, a conductivity sensor, and a temperature sensor.

27. A portable monitoring system, comprising:
an elongated probe assembly having a proximate end and a distal end and a conduit that extends between an opening at least proximate the proximate end and a substantially transparent chamber portion at least proximate the distal end, the conduit sized and dimensioned to receive a swab therein via the opening; and
an instrument including a housing, a dark chamber assembly, a multi-pixel photon counter, and at least one processor, the dark chamber assembly, the multi-pixel photon counter sensor and the at least one processor housed by the housing, the dark chamber assembly having a passage sized to removably receive the elongated probe assembly therein via an entrance that provides access into the passage from an exterior of the housing and which terminates in a dark chamber having an inner surface that at least partially encloses an interior of the dark chamber, at least a portion of the inner surface optically reflective and spherical with an associated focal point, the passage having a longitudinal axis that intersects the focal point of the optically reflective and spherical portion of the inner surface of the dark chamber, the multi-pixel photon counter sensor exposed to the interior of the dark chamber and shielded thereby from any ambient light, the at least one processor communicatively coupled to the multi-pixel photon counter sensor.

28. The portable monitoring system of claim 27 wherein in use the chamber portion of the probe assembly holds a liquid and a substantially transparent wall of the probe assembly and the liquid focus bioluminescence from a sample in the probe assembly on the multi-pixel photon counter sensor.

29. The portable monitoring system of claim 27 wherein the probe assembly includes at least one reagent reservoir and a membrane that retains a reagent in the reagent reservoir until breached.

30. The portable monitoring system of claim 27 wherein the instrument includes at least one spring that bias the probe assembly in a first direction toward the entrance of the passage, and the instrument includes a cover selectively moveable between an open position that provides access to the passage via the entrance from the exterior of the housing and a closed position which denies access to the passage from the exterior of the housing, and wherein in the closed position the cover causes the probe assembly to be urged away from the entrance of the passage toward the dark chamber.

31. The portable monitoring system of claim 27 wherein the instrument further includes a heat exchanger conductively coupled to transfer heat away from the multi-pixel photon counter sensor.

32. The portable monitoring system of claim 27 wherein at least a portion of the probe assembly has a defined non-circular profile and a defined length, and at least a portion of the dark chamber assembly has a complementary non-circular profile sized and dimensioned to receive the portion of the probe assembly.

33. The portable monitoring system of claim 27 wherein at least a portion of the probe assembly has an authentication value and the instrument includes at least one transducer positioned to read the authentication value when the probe assembly is at least partially inserted into the passage through the entrance.

34. The portable monitoring system of claim 27 wherein a proximate portion of the probe assembly is opaque.

* * * * *